(12) United States Patent
Nadel et al.

(10) Patent No.: US 7,700,547 B2
(45) Date of Patent: *Apr. 20, 2010

(54) PREVENTING AIRWAY MUCUS PRODUCTION BY ADMINISTRATION OF EGF-R ANTAGONISTS

(75) Inventors: Jay A. Nadel, San Francisco, CA (US); Kiyoshi Takeyama, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/013,013

(22) Filed: Jan. 11, 2008

(65) Prior Publication Data

US 2008/0199462 A1 Aug. 21, 2008

Related U.S. Application Data

(63) Continuation of application No. 10/816,159, filed on Mar. 31, 2004, now Pat. No. 7,354,894, which is a continuation of application No. 09/616,223, filed on Jul. 14, 2000, now Pat. No. 6,846,799, which is a continuation-in-part of application No. 09/375,597, filed on Aug. 17, 1999, now Pat. No. 6,270,747.

(60) Provisional application No. 60/097,023, filed on Aug. 18, 1998.

(51) Int. Cl.
*A01N 37/15* (2006.01)
*A01N 61/00* (2006.01)
*C07K 16/00* (2006.01)

(52) U.S. Cl. .................. 514/2; 514/1; 530/387.1; 530/388.1; 530/388.15; 530/388.22

(58) Field of Classification Search ............... 435/6, 435/375; 424/9.1, 9.2; 514/1, 2, 44; 530/300, 530/350, 387.1, 388.1, 388.24, 388.5, 387.3, 530/388.15, 388.22
See application file for complete search history.

(56) References Cited

U.S. PATENT DOCUMENTS

| | | | |
|---|---|---|---|
| 3,634,582 A | 1/1972 | Hartley, et al. | |
| 5,089,516 A | 2/1992 | Shiraishi et al. | |
| 5,116,616 A | 5/1992 | Gonenne | |
| 5,525,625 A | 6/1996 | Bridges et al. | |
| 5,559,111 A | 9/1996 | Göschke | |
| 5,760,041 A | 6/1998 | Wissner et al. | |
| 6,037,361 A | 3/2000 | Roth et al. | |
| 6,306,674 B1 | 10/2001 | Zory | |
| 6,306,874 B1 | 10/2001 | Fraley et al. | |
| 6,551,989 B2 | 4/2003 | Nadel et al. | |
| 6,627,634 B2 | 9/2003 | Himmelsbach et al. | |
| 7,354,894 B2 * | 4/2008 | Nadel et al. | 514/1 |

FOREIGN PATENT DOCUMENTS

| | | |
|---|---|---|
| AU | 760766 B2 | 3/2000 |
| DE | 1792207 | 11/1971 |
| DE | 4117078 A1 | 11/1992 |
| DE | 4310051 A1 | 10/1993 |
| WO | WO90/03374 A1 | 4/1990 |
| WO | WO92/18481 A1 | 10/1992 |
| WO | WO 9508114 A1 | 3/1995 |
| WO | WO96/09294 A1 | 3/1996 |
| WO | WO97/19065 A1 | 5/1997 |
| WO | WO97/45412 A1 | 12/1997 |
| WO | WO 9804133 A1 | 2/1998 |
| WO | WO9816228 A1 | 4/1998 |
| WO | WO98/37881 A1 | 9/1998 |
| WO | WO99/01421 A1 | 1/1999 |
| WO | WO99/01426 A1 | 1/1999 |
| WO | WO99/32121 | 7/1999 |
| WO | WO9945009 A1 | 10/1999 |
| WO | WO00/06560 A1 | 2/2000 |
| WO | WO00/06561 A1 | 2/2000 |
| WO | WO00/09485 A1 | 2/2000 |
| WO | WO00/10588 A2 | 3/2000 |
| WO | WO00/17162 A1 | 3/2000 |
| WO | WO0177104 A1 | 10/2001 |

OTHER PUBLICATIONS

Stayton, P. et al., J. Controlled Release, vol. 65, pp. 203-220 (2000).*
Loboto, M.N. et al., Trends in Molecular Med., vol. 9, No. 9, pp. 390-396 (2003).*
Amishma et al., "Expression of epidermal growth factor and epidermal growth factor receptor immunoraeactivity in the asthmatic human airway,": American Journal of Respiratory and Critical Care Medicine, 1998, 157(6):1907-1912.
Branch, "A good antisense molecule is hard to find," Trends Biochem. Sci., 1998, 23(2):45-50.
Brown, "Clinical Studies with matrix metallproteinase inhibitors," APMIS, 1999, 107:174-180.
Buchdunger et al., "4,5-Dianilinophthalimide: a protein-tyrosine kinase inhibitor with selectivity for the epidermal growth factor receptor signal transduction pathway and potent in vivo antitumor activity," Proc. Natl. Acad. Sci. USA, 1994, 91 (6):2334-2338.

(Continued)

Primary Examiner—Jane Zara
(74) Attorney, Agent, or Firm—Paula A. Borden; Pamela J. Sherwood; Bozicevic, Field & Francis LLP

(57) ABSTRACT

Hypersecretion of mucus in the lungs is inhibited by the administration of an epidermal growth factor receptor (EGF-R) antagonist. The EGF-R antagonist may be in the form of a small organic molecule, an antibody, or portion of an antibody that binds to and blocks the EGF receptor. The EGF-R antagonist is preferably administered by injection in an amount sufficient to inhibit formation of goblet cells in pulmonary airways. The degranulation of goblet cells that results in airway mucus production is thereby inhibited. Assays for screening candidate agents that inhibit goblet cell proliferation are also provided.

13 Claims, 15 Drawing Sheets

OTHER PUBLICATIONS

Burgel et al., "Relation of epidermal growth factor receptor expression to goblet cell hyperplasia in nasal polyps," Journal of Allergy and Clinical Immunology, 2000, 106(4):705-712.

Crooke, Stanley T., Antisense Research and Application, 1998, Chapter 1, pp. 1-50.

Desseyn et al., "Human Mucin Gene MUC5B, the 10.7-kb Large Central Exon Encodes Various Alternate Subdomains Resulting in a Super-repeat," The Journal of Biological Chemistry, 1997, 272(6): 3168-3178.

Donato et al, "Tumor Necrosis Factor Modulates Epidermal Growth Factor Receptor Phosphorylation and Kinase Activity in Human Tumor Cells," The Journal of Biological Chemistry, 1989, 264(34):20474-20481.

Goldstein et al., "Biological Efficacy of a Chimeric Antibody to the Epidermal Growth Factor Receptor in a Human Tumor Xenograft Model," Clinical Cancer Research, 1995, 1:1311-1318.

Grandis et al., "Inhibition of epidermal growth factor receptor gene expression and function decreases proliferation of head and neck squamous carcinoma but not norml mucosal epithelial cells," Oncogene, 1997, 15(4):409-416.

Guzman et al., "Epidermal growth factor regulates expression of the mucous phenotype of rat tracheal epithelial cells," Biochem. Biophys. Res. Com., 1995, 217(2): 412-418.

Kawamoto et al., "Growth stimulation of A431 cells by epidermal growth factor: Identification of high-affinity receptors fo epidermal growth factor by an anti-receptor monoclonal antibody," Proc. Natl. Acad. Sci. USA, 1983, 80:1337-1341.

Khetarpal et al., "Dispositional characteristics of a tyrosine kinase inhibitor (RG 14620) in rats and rabbits following intravenous administration or dermal application," Drug Metabolism and Disposition, 1994, 22(2):216-223.

Kim et al., "Levels of Intracellular Protein and Messenger RNA of Mucin and Lysozyme in Normal Human Nasal and Polyp Epithelium," The Laryngoscope, 2000, 110(2 pt. 1):276-280.

Kondapaka et al., "Tyrosine kinase inhibitor as a novel signal transduction and antiproliferative agent: prostate cancer," Molecular and Cellular Endocrinology, 1996, 117:53-58.

Kumar et al., "Cooperative interaction of autocrine and paracrine mitogens for airway epithelial cells," Cell Biology and Toxicology, 1998, 14:293-299.

Kumar et al., "Cooperative interaction of autocrine and paracrine mitogens for airway epithelial cells," Cell Biology and Toxicology, 1998, 14(4):293-299.

Lee et al., "Epidermal growth factor receptor signaling mediates regranulation of rat nasal goblet cells," Journal of Allergy and Clinical Immunology, 2001, 107(6):1046-1050.

Lee et al., "Leukotriene Receptor Antagonists and Synthesis Inhibitors Reverse Survival in Eosinophils of Asthmatic Individuals," American Journal of Respiratory and Critical Care Medicine, 2000, 161(6):1881-1886.

Levitski, "Signal-transduction therapy, a novel approach to disease management", Eur. J. Biochem., 1994, 226(1):1-13.

Lorimer, et al., "Immunotoxins that Target an Oncogenic Mutant Epidermal Growth Factor Receptor Expressed in Human Tumors," Clinical Cancer Research, 1995, 1:859-864.

Masui et al., "Growth inhibition of human tumor cells in athymic mice by anti-epidermal growth factor receptor monoclonal antibodies," Cancer Res., 1984, 44(3):1002-1007.

Nadel et al., "The role of epidermal growth factor in mucus production," Current Opinion in Pharmacology, 2001, 1 (3):254-258.

Nadel, "Role of epidermal growth factor receptor activation in regulating mucin synthesis," Respiratory Research, 2001, 2(2):85-89.

Palú et al., In pursuit of new developments for gene therapy of human diseases, Journal of Biotechnology, 1999, 68 (1):1-13.

Petit et al., "Neutralizing Antibodies against Epidermal Growth Factor and ErbB-2/neu Receptor Tyrosine Kinases Down-Regulate Vascular Endothelial Growth Factor Production by Tumor Cells in Vitro and in Vivo," American Journal of Pathology, 1997, 151(6)1523-1530.

Pihl-Carey, "Isis to Cronh's Disease Drug Fails in Phase III," Bioworld Today, 1999, 10(239):1-2.

Powis, "Signaling pathways as targets for anticancer drug development," Pharmac. Ther., 1994, 62:57-95.

Prenzel et al., "EGF receptor transactivation by G-protein-coupled receptors requires metalloproteinase cleavage of proHB-EGF," Nature, 1999, 402:884-888.

Schmidt et al., "Targeted inhibition of tumor cell growth by a bispecific single-chain toxin containing an antibody domain and TGF.alpha.," British Journal of Cancer, 1996, 74: 853-862.

Takeyama et al., "Epidermal growth factor system regulates mucin production in airways." Proceedings of the national Academy of Sciences USA, 1999, 96(6):3081-3086.

Takeyama et al., "Neutrophil-dependent goblet cell degranulation: role of membrane-bound elastase and adhesion molecules," Am. J. Physiol., 1998, 275:294-302.

Takeyama et al., "Oxidative stress causes mucin synthesis via transactivation of epdiermal growth factor receptor: role of neutorphils," Journal of Immunology, 2000, 164(3):1546-1552.

Temann et al., "A Novel Role of Murine IL-4 In Vivo: Induction of MUC5AC Gene Expression and Mucin Hypersecretion," Am J. Respir. Cell. Biol., 1997, 16:471-478.

Ullrich et al., "Human epidermal growth factor receptor cDNA sequence and aberrant expression of the amplified gene in A431 epidermoid carcinoma cells," Nature, 1984, 309(5967):418-425.

Van Herwaarden et al., "The role of N-acetylcpteine in the treatment of chronic obstmctive pulmonary disease," Netherlands Journal of Medicine, 1995, 47:45-48.

Wojtowicz-Praga et al., "Matrix metalloproteinase inhibitors," Investigational New Drugs, 1997, 15:61-75.

Yoneda et al., "The antiproliferative effects of tyrosine kinase inhibitors tyrphostins on a human squamous cell carcinoma in vitro and in nude mice," Cancer Res., 1991, 51(16):4430-4435.

Lund, V.J. Diagnosis and treatment of nasal polyps. British Medical Journal. 1995, vol. 311, No. 7017, pp. 1411-1414.

Baselga. Why the epidermal growth factor receptor? The rationale for cancer therapy. Oncologist. 2002;7 Suppl 4:2-8.

Ciardiello and Tortora. A novel approach in the treatment of cancer: targeting the epidermal growth factor receptor. Clin Cancer Res. Oct. 2001;7(10):2958-70.

Kawamoto, et al. Growth stimulation of A431 cells by epidermal growth factor: identification of high-affinity receptors for epidermal growth factor by an anti-receptor monoclonal antibody. Proc Natl Acad Sci U S A. Mar. 1983;80 (5):1337-41.

Petit, et al. Neutralizing antibodies against epidermal growth factor and ErbB-2/neu receptor tyrosine kinases down-regulate vascular endothelial growth factor production by tumor cells in vitro and in vivo: angiogenic implications for signal transduction therapy of solid tumors. Am J Pathol. Dec. 1997;151(6):1523-30.

Schnurch, et al. Growth inhibition of xenotransplanted human carcinomas by a monoclonal antibody directed against the epidermal growth factor receptor. Eur J Cancer. 1994;30A(4):491-6.

* cited by examiner

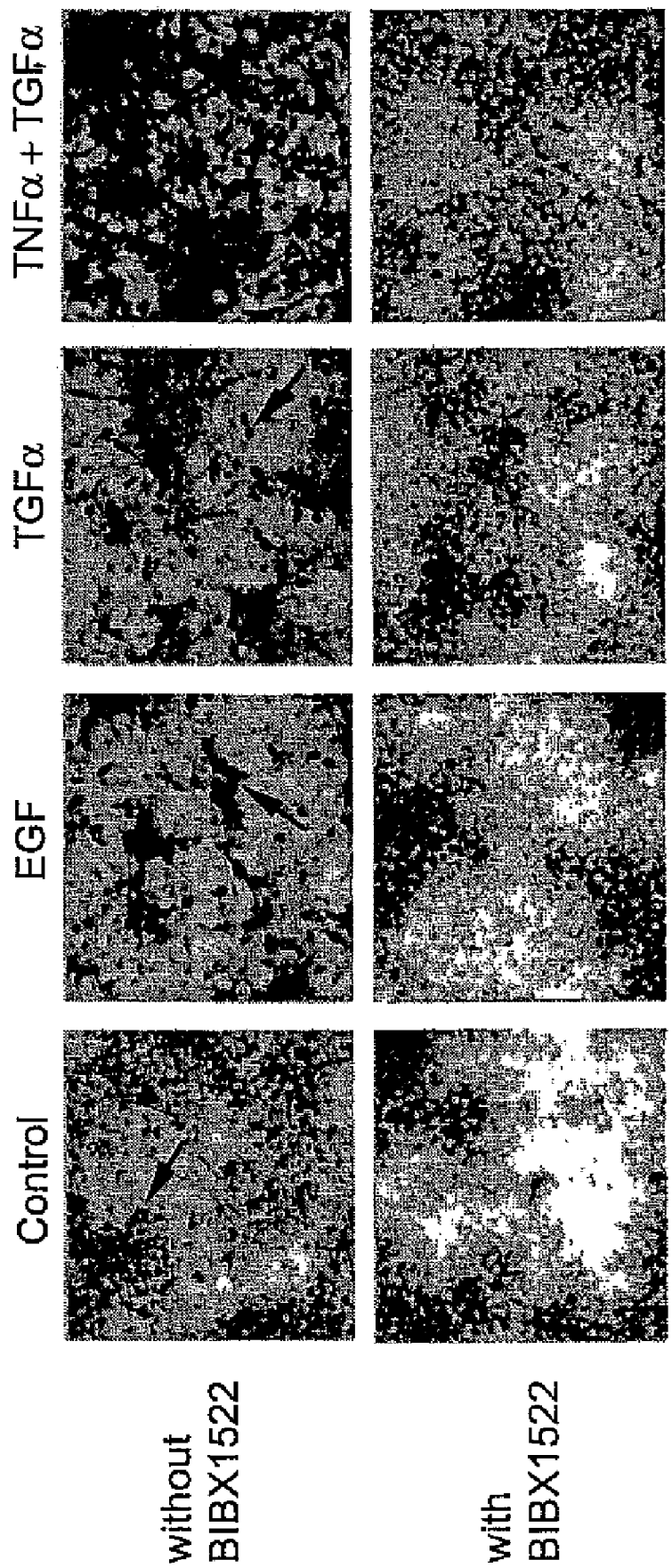

FIG. 3
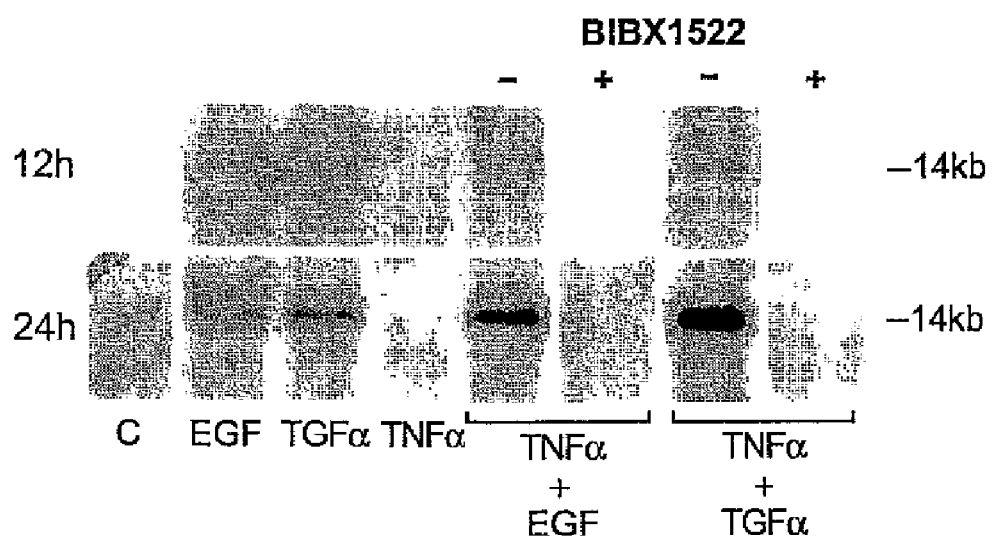
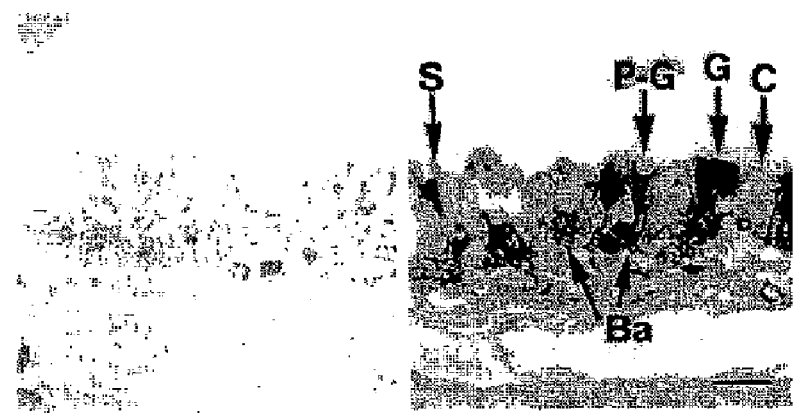
FIG. 4A
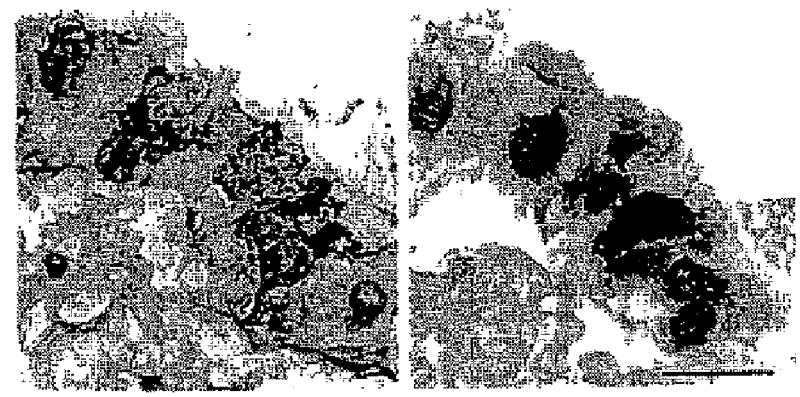
FIG. 4B

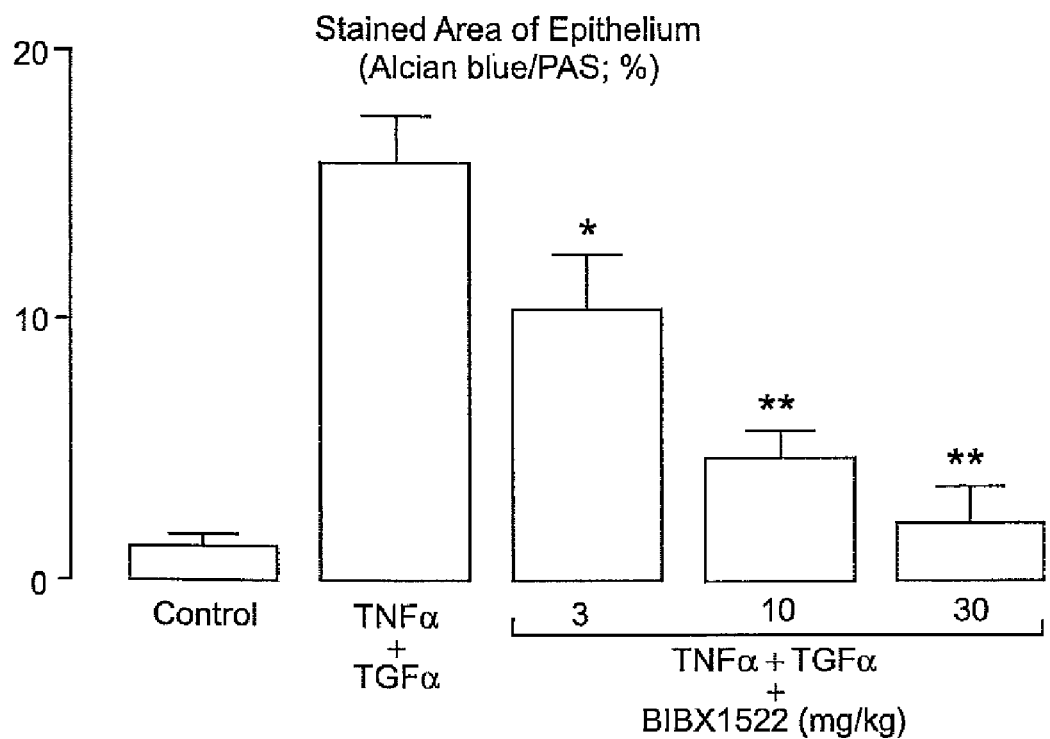
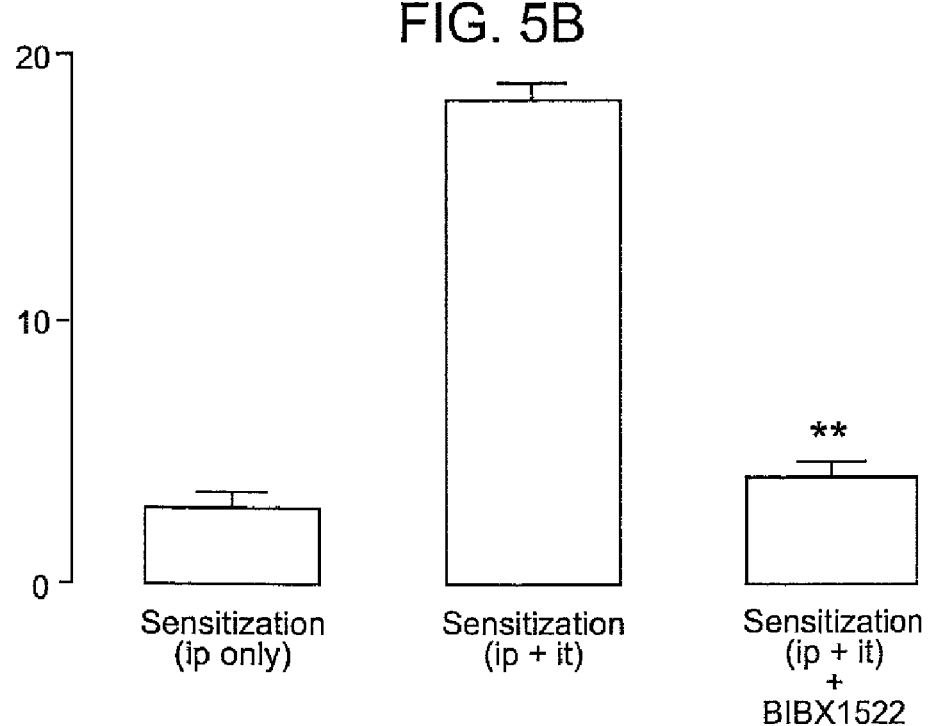

FIG. 8
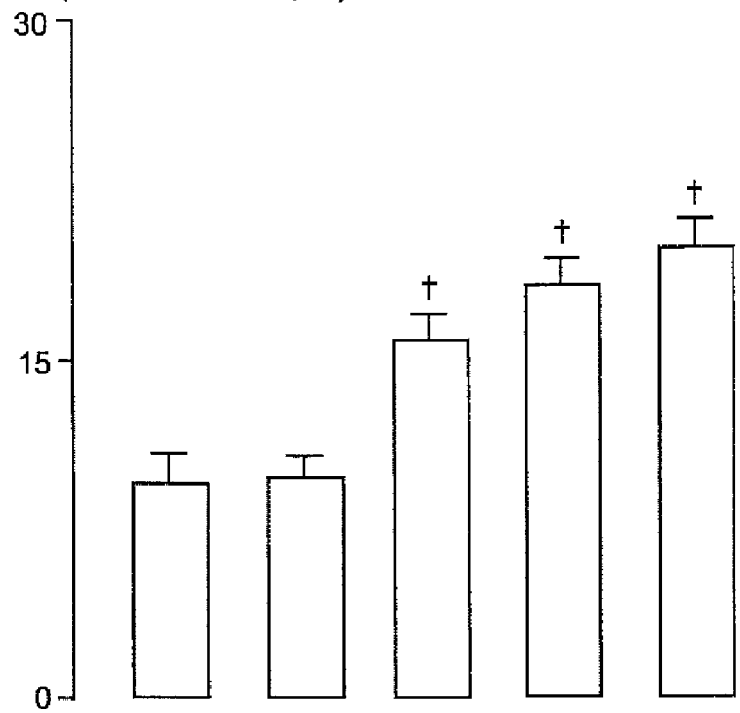
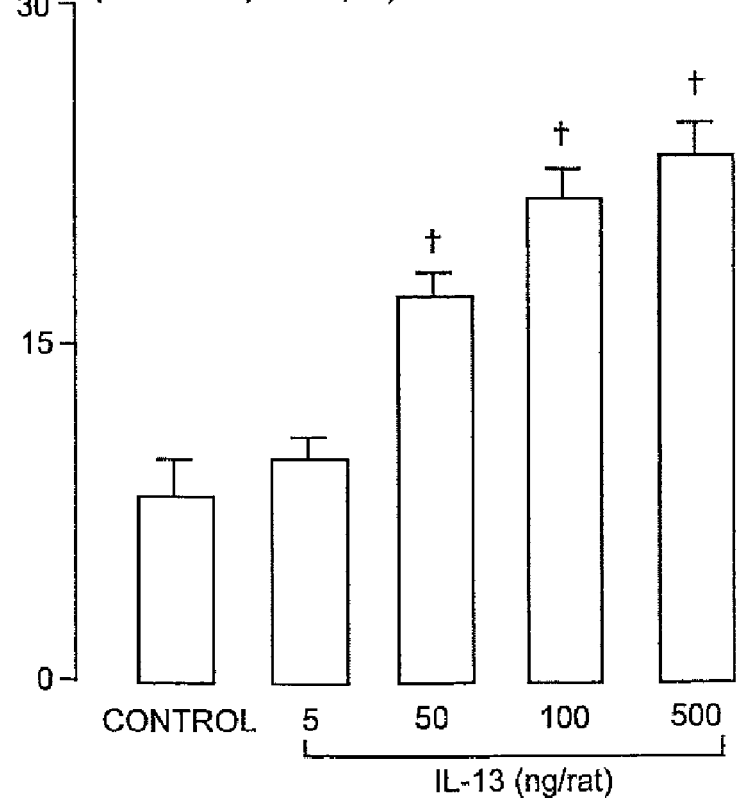

FIG. 10
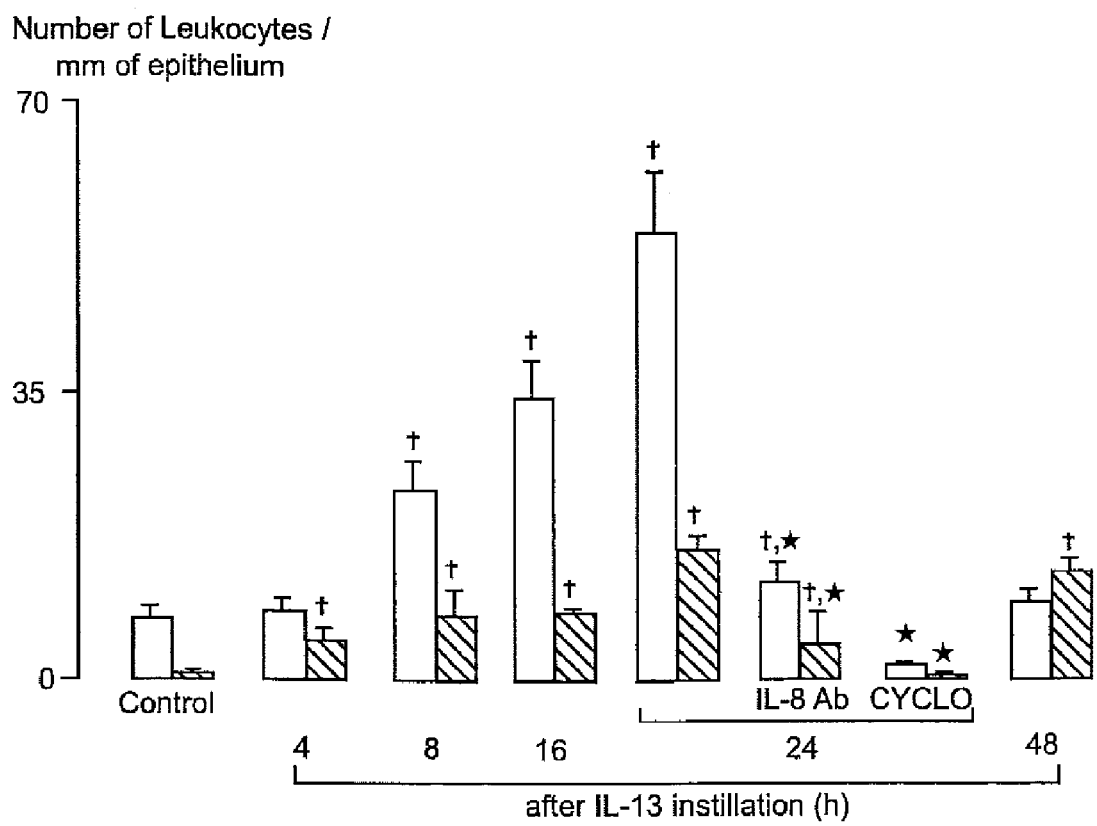
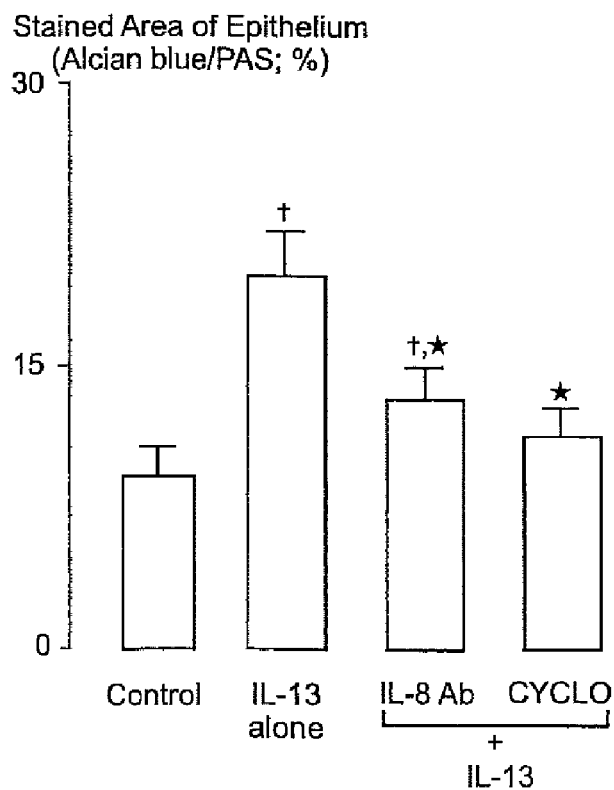

FIG. 11

FIG. 17
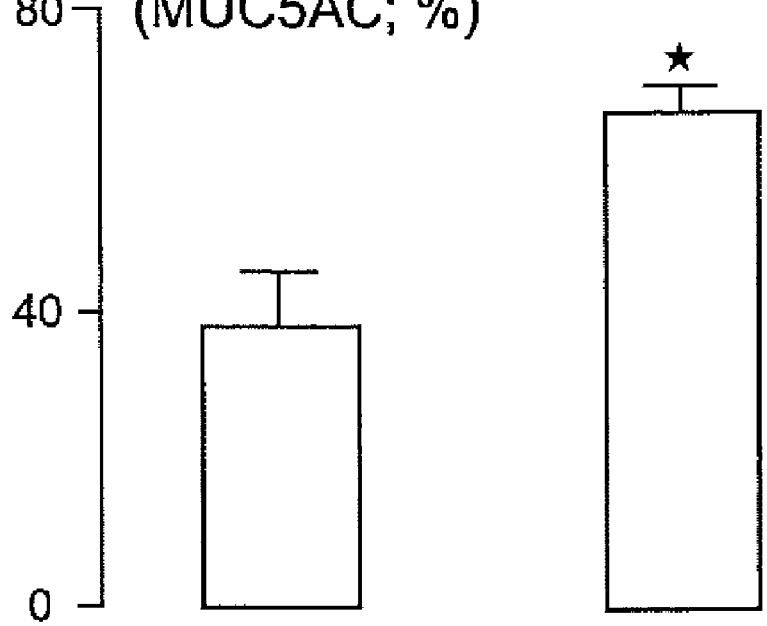
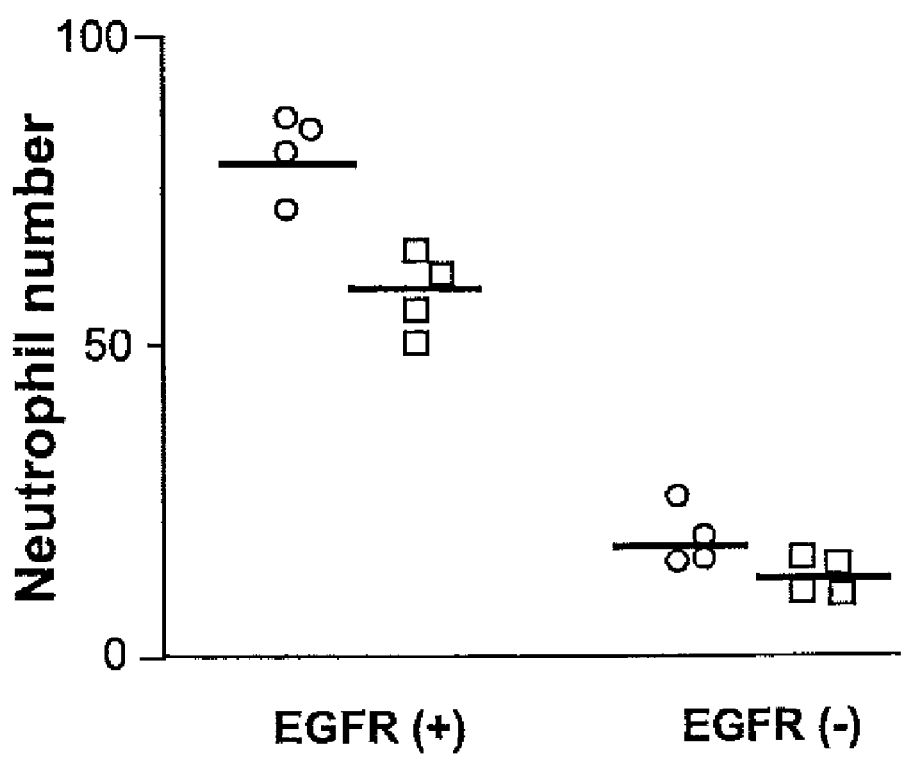

US 7,700,547 B2

PREVENTING AIRWAY MUCUS PRODUCTION BY ADMINISTRATION OF EGF-R ANTAGONISTS

GOVERNMENT RIGHTS

The United States Government has certain rights in this application pursuant to Grant HL-24136 awarded by the National Institutes of Health Program.

FIELD OF THE INVENTION

This invention relates generally to the field of pulmonary treatment. More particularly, the invention relates to inhibiting hypersecretion of mucus in lungs and airways by the administration of an EGF-R antagonist. In addition, this invention also relates to methods for the development or assessment of candidate agents capable of inhibiting hypersecretion of mucus in the lungs.

BACKGROUND OF THE INVENTION

In the conducting airways of the respiratory system, the mucociliary system serves as the primary defense mechanism to move inhaled particles or infectious agents out of the airways in the lungs. In addition, substances present in airway fluids serve to limit the toxicity of the particles and to inactivate infective agents. The physical mechanism of coughing serves to expel the mucus from the airway passages (see e.g., "Foundations of Respiratory Care," Pierson and Kacmarek, eds. (1992) Churchill Livingstone Inc. New York, N.Y.; "Harrison's Principles of Internal Medicine", Fauci et al., eds. (1997) 14th Edition, McGraw Hill, New York, N.Y.).

The mucociliary system consists of ciliated epithelial cells, epithelial goblet cells, and serous and mucous cells located in submucosal glands. The cilia are surrounded by an aqueous layer (periciliary fluid) secreted into the lumen of the airway passage by the active transport of chloride and the passive movement of water across the epithelium. The cilia make contact with the mucus floating on this aqueous layer, and via a unidirectional propelling motion provide for movement of mucus toward the glottis (see Pierson and Kacmarek, supra and Fauci, et al., supra). Mucus is produced by the epithelial goblet cells and submucosal gland cells and is secreted into the lumen of the airway after degranulation.

While mucus generally facilitates the clearance of inhaled particles or infectious agents, hypersecretion of mucus in the airways may cause progressive airway obstruction. In peripheral airways, cough is ineffective for clearing secretions. Furthermore, because of their small dimensions, small airways containing many goblet cells are especially vulnerable to airway plugging by mucus. Airway hypersecretion affects a substantial number of individuals; it is seen in a variety of pulmonary diseases, such as chronic bronchitis, acute asthma, cystic fibrosis, and bronchiectasis.

Hypersecretion of mucus is the major symptom in patients with chronic obstructive pulmonary disease (COPD) and defines the condition (i.e. chronic cough and sputum production). This condition alone affects 14 million Americans and can cause progressive disability and death. It has been estimated that asthma affects at least 4% of the U.S. population and accounts for at least 2000 deaths annually (Pierson and Kucmarek, supra). During an acute asthmatic event, the bronchial walls swell, mucus volume increases and bronchial smooth muscle contracts, resulting in airway narrowing. As a result of hypersecretion in acute asthma, extensive mucus plugging can be a major cause of morbidity and mortality.

Hypersecretion has also been implicated in cystic fibrosis, which is one of the most common, fatal, genetic diseases in the world. Cystic fibrosis is an autosomal recessive disease that causes the airway mucosal cell to become unresponsive to cyclic-AMP-dependent protein kinase activation of the membrane chloride ion channels (Pierson and Kacmarek, supra and Fauci, et al., supra). The subsequent electrolyte imbalance reduces the level of hydration of the airway mucus, thus resulting in highly viscous mucus in the lungs of an individual afflicted with cystic fibrosis. Hypersecretion obstructs the air passages of individuals with cystic fibrosis, further compromising lung function.

Other disease involving hypersecretion include chronic obstructive lung disorder (COPD). Oxidant stress plays an important role in the pathogenesis of COPD. Cigarette smoke, which generates oxygen free radicals, is strongly implicated in the pathogenesis. Neutrophils are often seen at site of inflammation in COPD, and interestingly, oxygen free radicals are known to be released by neutrophils during activation.

Mechanical intubation is often necessary in order to provide assisted ventilation to patients with various pulmonary diseases. A tube is introduced via the oropharanx and placed in the trachea. To prevent leaking of air around the endotracheal tube, a balloon is inflated around the tube in the lower trachea, which may abrade the epithelium and cause goblet cell metaplasia. Wounding of epithelium leads to repair processes, which can result in abundant mucus secretion. Such prolonged tracheal intubation in patients can lead to deleterious effects due to hypersecretion.

As a result of the high levels of mucus in the lungs of patients with hypersecretory pulmonary diseases, mucosal clearance is reduced. Pathological agents such as bacteria, e.g. *Pseudomonas aeruginosa*, often establish colonies within the mucus, resulting in frequent lung infection.

Classical modalities of treating individuals afflicted with airway hypersecretion include antibiotic therapy, bronchodilators (e.g., methylxanthines, sympathomimetics with strong β2 adrenergic stimulating properties, anticholinergics), use of systemic or inhaled corticosteroids, primarily in asthma, liquefaction of the mucus by oral administration of expectorants, e.g. guaifenesin, and aerosol delivery of "mucolytic" agents, e.g. water, hypertonic saline solution (see Harrison's, supra). A newer therapy for cystic fibrosis is the administration of DNAse to target the DNA-rich mucus or sputum (Shak, et al. (1990) *Proc. Natl. Acad.* (USA) 87:9188-9192; Hubbard, R. C. et al. (1991) *N. Engl. J. Med.* 326:812). In addition, chest physical therapy consisting of percussion, vibration and drainage are also used to facilitate clearance of viscous mucus. Lung transplantation may be a final option for those with severe pulmonary impairment. Therefore, more efficacious or alternative therapy to target the mucosal secretions is needed. Specifically, there is a need for a specific modality that will reduce the formation of mucus secretions in the airways.

Relevant Literature

The use of EGF inhibitors to block the growth of cancer cells is reviewed by Levitski (1994) *Eur. J. Biochem.* 226(1): 1-13; Powis (1994) *Pharmac. Ther.* 62:57-95; Kondapaka and Reddy (1996) *Mol. Cell. Endocrin.* 117:53-58.

SUMMARY OF THE INVENTION

Hypersecretion of mucus in airways is an adverse symptom of a number of different pulmonary diseases. The secretion results from the degranulation of goblet cells, the proliferation of which is promoted by stimulation of epidermal growth factor receptors (EGF-R). The present invention treats pulmonary hypersecretion by administering therapeutic amounts of EGF antagonists, preferably kinase inhibitors. The antagonists may be in the form of small molecules, antibodies, or portions of antibodies that bind to either EGF or its receptor. In another aspect of the invention, in vitro and in vivo methods predictive of the therapeutic potential of candidate agents to inhibit hypersecretion of mucus are provided.

A primary object of the invention is to provide a method of treating diseases involving hypersecretion of mucus in lungs.

Another object of the invention is to provide formulations useful in the treatment of diseases that result in hypersecretion of mucus.

Yet another object of the invention is to provide an in vitro assay for the screening of candidate agents that inhibit hypersecretion of mucus, where the method involves the steps of (i) contacting an in vitro model of goblet cell proliferation with EGF or the functional equivalent thereof; (ii) subsequently contacting the in vitro model with a candidate agent; and (iii) assessing goblet cell proliferation, wherein inhibition of goblet cell proliferation is indicative of the candidate agent's therapeutic potential.

Another object of the invention is to provide an in vivo assay for the screening of candidate agents that inhibit hypersecretion of mucus, where the method involves (i) creating an animal model of hypersecretory pulmonary disease by inducing EGF-R, e.g. with tumor necrosis factor-alpha (TNF-α); (ii) stimulating the induced EGF-R with its ligand, e.g. transforming growth factor alpha (TGF-α) or EGF, to produce mucin producing goblet cells; (iii) treating with a candidate agent; and (iv) assessing goblet cell proliferation or mucus secretion, wherein an inhibition of goblet cell proliferation or mucus secretion is indicative of the candidate agent's therapeutic potential.

A further object of the invention is to provide in vitro and in vivo assays for the screening of EGF-R antagonists that inhibit hypersecretion of mucus.

An advantage of the invention is that it provides a means for preventing excessive formation of mucus in pulmonary airways.

A feature of the invention is that a range of different types of antagonists can be used to block the effects of EGF and/or TGF-α and their interaction with EGF-R.

An aspect of the invention is formulations of EGF antagonists for reducing formation of mucus secretion in the airways of a mammalian patient, preferably a human patient.

Another object of the invention is a method of pulmonary delivery of EGF antagonists for reducing mucus secretions in the airways of a mammalian patient, preferably a human patient.

Another object of the invention is to provide a method for treating a range of different diseases which have as a symptom the excess formulation of mucus secretions in the airways. These diseases include, without limitation, chronic bronchitis, acute asthma, cystic fibrosis, bronchiectasis, chronic obstructive lung disease, hypersecretion resulting from epithelial damage such as allergic stimuli or mechanical abrasions, and nasal hypersecretion.

These and other objects, advantages, and features of the invention will become apparent to those persons skilled in the art upon reading the details of the treatment methods, and in vitro and in vivo assay methods, as more fully described below.

BRIEF DESCRIPTION OF THE DRAWINGS

FIG. 2. Alcian blue/PAS staining of NCI-H292 cells for identification of mucin glycoproteins.

FIG. 3. Northern analysis for MUC5 gene expression in NCI-H292 cells.

FIGS. 4A and 4B. Immunohistochemical analysis of EGF-R with an anti-EGF-R antibody in pathogen-free rats. FIG. 4A, TNFα-treated rats. FIG. 4B, ovalbumin-sensitized rats.

FIG. 5 is a graph depicting the effect of EGF-R tyrosine kinase inhibitor (BIBX1522) on production of goblet cells (expressed as % of stained area of airway epithelium occupied by Alcian blue/PAS-positive stained cells).

FIG. 8 is a graph depicting the dose-dependent effect of IL-13 instillation on percent area of Alcian blue (AB)/PAS staining (FIG. 8A) and MUC5AC protein expression (FIG. 8B) in rat airways.

FIG. 10 is a graph depicting the effect of IL-13 instillation on leukocyte recruitment (FIG. 10A) and Alcian blue (AB)/PAS staining (FIG. 10B) in rat airway epithelium.

FIG. 11 is an autoradiograph depicting tyrosine phosphorylation of EGFR induced by cigarette smoke and by TGFα. Results are representative of three different experiments. Bar=170 kD.

FIG. 17 is a graph depicting goblet cell degranulation in EGFR-positive and EGFR-negative polyps.

DETAILED DESCRIPTION OF THE PREFERRED EMBODIMENTS

Figure 1A:
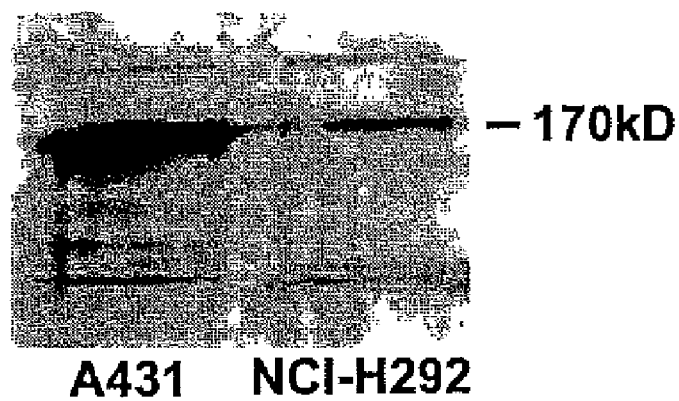
FIG. 1A is a western blot of EGF-R in NCI-H292 and in A431 cells.

Compositions and methods are provided for the treatment of airway mucus hypersecretion by administering therapeutic amounts of EGF antagonists, preferably kinase inhibitors. The antagonists may be in the form of small molecules, antibodies, or portions of antibodies that bind to either EGF or its receptor. In airway hypersecretory diseases, e.g. chronic bronchitis, bronchiectasis, cystic fibrosis, acute asthma, COPD, etc., mucin synthesis in airways is increased and mucus hypersecretion occurs. The secreted mucus results in airway obstruction, an effect that causes death in these diseases.

Several causes of airway damage and inflammation are shown herein to induce the expression of the epidermal growth factor receptor in airway epithelial cells. After induction of EGF-R, subsequent stimulation of EGF-R by both ligand-dependent and -independent mechanisms results in mucin production at both gene expression and protein levels. Selective inhibitors of EGF-R tyrosine kinase are demonstrated to block this mucin gene and protein expression.

Without limiting the invention, it is suggested that an evolutionary sequence of goblet cell production may be based on the expression of EGF-R. Stimulation with TNFα induces intense EGF-R staining of non-granulated secretory cells; their subsequent activation by EGF-R ligands causes progressive staining for mucous glycoconjugates in the cytoplasm, and the cells become "pre-goblet" and then "goblet" cells. The data suggest that EGF-R activation promotes selective cell differentiation, but not proliferation. Goblet cells are apparently derived from non-granulated secretory cells that express EGF-R and are stimulated by EGF-R ligands to produce mucins.

In addition to stimulation by cytokines, the EGF-R may be stimulated by other signaling mediators. For example, prolonged cigarette smoking is associated with progressive pathologic changes in peripheral airways, including goblet cell hyperplasia. Proinflammatory cytokine-activated neutrophils and cigarette smoke are shown to cause mucin synthesis in human bronchial epithelial cells via ligand-independent activation of EGF-R, implicating recruited neutrophils and cigarette smoke as regulators of epithelial cell differentiation that result in abnormal induction of mucin-producing cells in airways. Neutrophils activated by a variety of stimuli, including IL-8, N-formyl-methionyl-leucyl-phenylalanine, TNF-α, cigarette smoke or $H_2O_2$ upregulate mucin expression in epithelial cells, which synthesis is inhibited by EGF-R inhibitors. Neutrophils are also capable of producing the EGF-R ligands, EGF and TGFα. In addition, epithelial cells are sources of EGF-R ligands.

Mechanical injury to airway epithelium can also cause hypersecretion, and be responsible for mucous plugging. Inhibitors of EGF-R tyrosine kinase serve to prevent mucous hypersecretion after tracheal intubation.

Epithelial damage is a common finding in studies of patients even with mild asthma, and the damage is increasingly related to worsening of clinical symptoms. Epithelial damage produced by the allergic response induces EGF-R activation, which results in abnormal goblet cell production. EGF-R is implicated in epithelial damage, for example the "airway remodeling" that occurs in asthma, repair and wound closure. Mechanical epithelial damage and epithelial injury in asthma may involve a similar EGF-R cascade, resulting in abnormal growth of epithelial secretory cells.

Hypersecretion is also an important manifestation of inflammatory diseases of the nose. When nasal goblet cells are "challenged" by inducing goblet cell degranulation utilizing a neutrophil-dependent mechanism, expression of EGF-R and mucins are strongly upregulated. These events were associated with regranulation of the goblet cells. When inflammation, such as stimulation of neutrophil infiltration, causes goblet cell degranulation and mucin secretion, up-regulation and activation of EGF-R re-supplies the airway epithelium with mucins.

Before the present methods of treatment and formulations are described, it is to be understood that this invention is not limited to particular methods and formulations described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

By "epidermal growth factor" or "EGF" is meant a protein or portion thereof having biological activity characterized by mitogenic activity on epithelial cells (e.g., Cohen (1986) *Biosciences Reports* 6(12): 1017; Aaronson, S. A., "Growth Factors and Cancer," *Science* (1991) 254:1146-1153). Exemplary is the human epidermal growth factor, for example as described by Urdea et al. (1983) *Proc. Nat. Acad. Sci.* 80:7461-7465.

Of particular interest for the purposes of this invention is the mitogenic activity of EGF on goblet cells. Also intended to be encompassed by this definition are proteins of portions thereof which are the functional equivalent of EGF in terms of the biological response elicited by EGF.

By "epidermal growth factor receptor" or "EGF-R" is meant a protein a portion thereof capable of binding EGF protein or a portion thereof. Exemplary is the human epidermal growth factor receptor (see Ullrich et al. (1984) *Nature* 309:418-425; Genbank accession number NM_005228). Preferably, the binding of the EGF ligand activates the EGF-R (e.g. resulting in activation of intracellular mitogenic signaling, autophosphorylation of EGF-R). One of skill in the art will appreciate that other ligands, in addition to EGF, may bind to EGF-R and activate the EGF-R. Examples of such ligands include, but are not limited to, TGF-α, betacellulin, amphiregulin, heparin-binding EGF (HB-EGF) and neuregulin (also known as hergulin) (Strawn and Shawver (1998) *Exp.-Opin. Invest. Drugs* 7(4)553-573, and "The Protein Kinase Facts Book: Protein Tyrosine Kinases" (1995) Hardie, et al. (eds.), Academic Press, NY, N.Y.).

By "EGF-R antagonist" is meant any agent capable of directly or indirectly inhibiting the effect of EGF-R, particularly the effect of EGF-R on goblet cell proliferation or hypersecretion of mucus by goblet cells. EGF-R can be activated through ligand-dependent and ligand-independent mechanisms, resulting in either autophosphorylation or trans-phosphorylation, respectively. EGF-R antagonists of interest may inhibit either or both of these mechanisms. For example, binding of TNF-α to the EGF-R results in a ligand-dependent phosphorylation, which may be blocked by an antibody that binds EGF-R, thereby preventing the interaction of EGF with a ligand that would activate the EGF receptor. Examples of such antibodies are described by Goldstein et al. (1995) *Clin. Cancer Res.* 1:1311-1318; Lorimer et al. (1995) *Clin. Cancer Res.* 1:859-864; Schmidt and Wels (1996) *Br. J. Cancer* 74:853-862. Small molecule tyrosine kinase inhibitors are also effective as EGF-R antagonists.

Alternatively, it is shown that compounds such as oxygen free radicals stimulate a trans-phosphorylation of the EGF-R, resulting in ligand-independent activation of the receptor. Other means of activating EGF-R by transphosphorylation include ultraviolet and osmotic stress, stimulation of G-protein coupled-receptor by endothelin-1, lysophosphatidic acid and thrombin, m1 muscarinic acetylcholine receptor, and human growth hormone. Antagonists of this ligand-independent mechanism include anti-oxidants, such as super oxide dismutase, N-acetyl-L-cysteine, DMSO, DMTU, ascorbic acid, and the like. Ligand-independent activation of EGFR via oxidative stress results in activation of mitogen-activated protein kinase kinase (MEK) p44/42 mitogen-activated protein kinase (p44/42$^{mapk}$), resulting in mucin synthesis. This MEK activation is inhibited by the selective MEK inhibitor PD98059, as well as by antioxidants. Thus, encompassed by the term "EGFR antagonist" are MEK inhibitors and antioxidants.

Furthermore, EGFR-dependent signalling pathways may be activated upon stimulation of G-protein-coupled receptors (GPCR). Ligand activation of heterotrimeric G proteins by interaction with a GPCR results in an intracellular signal that induces the extracellular activity of a transmembrane metalloproteinase. This leads to extracellular processing of a transmembrane growth factor precursor and release of the mature factor which, directly or through the proteoglycan matrix, interacts with the ectodomain of EGFR and activates and intracellular signal. Prenzel et al. (1999) *Nature* 402:884-888. Thus, EGFR may be activated upon release of a membrane-bound EGFR ligand by action of the transmembrane metalloproteinase (MP). Accordingly, the term "EGFR antagonist" further encompasses inhibitors of this process, including, but not limited to, specific metalloproteinase inhibitors.

An EGF-R antagonist may be an antibody that binds to a factor that stimulates EGF production or EGF-R production, thereby inhibiting promotion of goblet cell proliferation by EGF (i.e. an inhibitor of the phosphorylation cascade that phosphorylates EGF-R). For example, a fusion protein of TGFa-*Pseudomonas* exotoxin 40 is described by Arteaga et al. (1995) *Cancer Res.* 54:4703-4709.

In a preferred embodiment, the EGF-R antagonist is an inhibitor of the tyrosine kinase activity of EGF-R, particularly small molecule inhibitors having selective action on EGF-R as compared to other tyrosine kinases—preferred small molecules block the natural EGF receptor in a mammal, preferably a human and have a molecular weight of less than 1 kD.

Inhibitors of EGF and EGF-R include, but are not limited to, tyrosine kinase inhibitors such as quinazolines, such as PD 153035, 4-(3-chloroanilino)quinazoline, or CP-358,774, pyridopyrimidines, pyrimidopyrimidines, pyrrolopyrimidines, such as CGP 59326, CGP 60261 and CGP 62706, and pyrazolopyrimidines (Shawn and Shawver, supra.), 4-(phenylamino)-7H-pyrrolo[2,3-d]pyrimidines (Traxier et al., (1996) *J. Med. Chem.* 39:2285-2292), curcumin (diferuloyl methane) (Laxmin arayana, et al., (1995), *Carcinogen* 16:1741-1745), 4,5-bis(4-fluoroanilino)phthalimide (Buchdunger et al. (1995) *Clin. Cancer Res.* 1:813-821; Dinney et al. (1997) *Clin. Cancer Res.* 3:161-168); tyrphostins containing nitrothiophene moieties (Brunton et al. (1996) *Anti Cancer Drug Design* 11:265-295); the protein kinase inhibitor ZD-1839 (AstraZeneca); CP-358774 (Pfizer, inc.); PD-0183805 (Warner-Lambert); or as described in International patent application WO99/09016 (American Cyanamid); WO98/43960 (American Cyanamid); WO97/38983 (Warener Labert); WO99/06378 (Warner Lambert); WO99/06396 (Warner Lambert); WO96/30347 (Pfizer, Inc.); WO96133978 (Zeneca); WO96/33977 (Zeneca); and WO96/33980) Zeneca; all herein incorporated by reference; or antisense molecules.

A "therapeutically effective amount" of an EGFR antagonist, as used herein in the context of treatment methods, is an amount of antagonist that is effective in inhibiting a parameter associated with EGFR activation.

By "inhibiting a parameter associated with EGFR activation" is meant reducing, decreasing, neutralizing, attenuating or preventing mucus cell hyperplasia; the proliferation of goblet cells; differentiation of epithelial airway cells into goblet cells; degranulation of goblet cells; or hypersecretion of mucus by goblet cells.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, particularly a human, and includes:

(a) preventing the disease or symptom from occurring in a subject who may be predisposed to the disease or symptom but has not yet been diagnosed as having it;

(b) inhibiting the disease or symptom, i.e., arresting its development; or (c) relieving the disease or symptom, i.e., causing regression of the disease or symptom. The invention is directed toward treating patients with pulmonary or airway disease and is particularly directed toward treating patients' hypersecretion of mucus, i.e. preventing, inhibiting or relieving hypersecretion of mucus. In terms of treating symptoms, the invention is directed toward decreasing mucus or sputum in the airways, inhibiting infection by pathological organisms, alleviating cough, and preventing hypoxia due to airway plugging.

More specifically "treatment" is intended to mean providing a therapeutically detectable and beneficial effect on a patient suffering from a pulmonary disease involving hypersecretion of mucus.

Still more specifically "treatment" shall mean preventing, alleviating, and/or inhibiting hypersecretion of mucus with a compound selected from the group consisting of EGF and/or EGF-R antagonists such as antibodies, protein tyrosine kinase inhibitors and antisense molecules; anti-oxidants; inhibitors of any factor in the EGFR cascade, including, but not limited to, inhibitors of MEK; metalloproteinase inhibitors; G protein-coupled receptor inhibitors; and the like. An alternative treatment may comprise prevention of EGF-R expression in airway, thereby blocking the pathway at an earlier stage. For example, reagents that block binding of TNFα to its receptor may prevent upregulation of EGF-R.

Treatment includes preventing or inhibiting infections by pathological agents caused by and/or related to hypersecretion of mucus.

By "antibody" is meant an immunoglobulin protein that is capable of binding an antigen. Antibody as used herein is meant to include antibody fragments, e.g. F(ab')2, Fab', Fab, capable of binding the antigen or antigenic fragment of interest. Preferably, the binding of the antibody to the antigen inhibits the activity of EGF or EGF-R.

The term "humanized antibody" is used herein to describe complete antibody molecules, i.e. composed of two complete light chains and two complete heavy chains, as well as antibodies consisting only of antibody fragments, e.g. Fab, Fab', F (ab)$_2$, and Fv, wherein the CDRs are derived from a non-human source and the remaining portion of the Ig molecule or fragment thereof is derived from a human antibody, preferably produced from a nucleic acid sequence encoding a human antibody.

The terms "human antibody" and "humanized antibody" are used herein to describe an antibody of which all portions of the antibody molecule are derived from a nucleic acid sequence encoding a human antibody. Such human antibodies are most desirable for use in antibody therapies, as such antibodies would elicit little or no immune response in the human patient.

The term "chimeric antibody" is used herein to describe an antibody molecule as well as antibody fragments, as described above in the definition of the term "humanized antibody." The term "chimeric antibody" encompasses humanized antibodies. Chimeric antibodies have at least one portion of a heavy or light chain amino acid sequence derived from a first mammalian species and another portion of the heavy or light chain amino acid sequence derived from a second, different mammalian species. Preferably, the variable region is derived from a non-human mammalian species and the constant region is derived from a human species. Specifically, the chimeric antibody is preferably produced from a nucleotide sequence from a non-human mammal encoding a variable region and a nucleotide sequence from a human encoding a constant region of an antibody.

By "binds specifically" is meant high avidity and/or high affinity binding of an antibody to a specific polypeptide. Antibody binding to its epitope on a specific polypeptide is stronger than binding of the same antibody to any other epitope, particularly those which may be present in molecules in association with, or in the same sample, as the specific polypeptide of interest. Antibodies that bind specifically to a polypeptide of interest may be capable of binding other polypeptides at a weak, yet detectable, level, e.g. 10% or less of the binding shown to the polypeptide of interest. Such weak binding, or background binding, is readily discernible from the specific antibody binding to the compound or polypeptide of interest, e.g. by use of appropriate controls.

By "detectably labeled antibody", "detectably labeled anti-EGF" or "detectably labeled anti-EGF fragment" is meant an antibody (or antibody fragment that retains binding specificity), having an attached detectable label. The detectable label is normally attached by chemical conjugation, but where the label is a polypeptide, it could alternatively be attached by genetic engineering techniques. Methods for production of detectably labeled proteins are well known in the art. Detectable labels may be selected from a variety of such labels known in the art, but normally are radioisotopes, fluorophores, enzymes, e.g. horseradish peroxidase, or other moieties or compounds that either emit a detectable signal (e.g. radioactivity, fluorescence, color) or emit a detectable signal after exposure of the label to its substrate. Various detectable label/substrate pairs (e.g. horseradish peroxidase/diaminobenzidine, avidin/streptavidin, luciferase/luciferin), methods for labeling antibodies, and methods for using labeled antibodies to detect an antigen are well known in the art (for example, see Harlow and Lane, eds. (*Antibodies*: A Laboratory Manual (1988) Cold Spring Harbor Laboratory Press, Cold Spring Harbor, N.Y.).

Therapeutic Methods

The present invention provides a method of treating pulmonary hypersecretion by administering therapeutic amounts of EGF-R antagonists. In general, the methods comprise administering a therapeutically effective amount of an EGFR antagonist to an individual suffering from airway hypersecretion of mucus. In some embodiments, the invention provides methods of treating hypersecretion of mucus in an airway of an individual by mucus-producing goblet cells. In other embodiments, the invention provides methods for reducing goblet cell hyperplasia in an airway of an individual. Any disease and particularly any pulmonary disease characterized by hypersecretion of mucus or accumulation of pathological levels of mucus may be treated by the methods described herein. Examples of pulmonary hypersecretory diseases that may be treated by this method include, but are not limited to, chronic obstructive lung diseases, such as chronic bronchitis, inflammatory diseases such as asthma, bronchiectasis, pulmonary fibrosis, COPD, diseases of nasal hypersecretion, e.g. nasal allergies, nasal polyps; and other hypersecretory diseases. Genetic diseases such as cystic fibrosis, Kartagener syndrome, alpha-1-antitrypsin deficiency, familial non-cystic fibrosis mucus inspissation of respiratory tract, are intended to be included as well.

Antagonists that directly target EGF or EGF-R are preferred. However, one of skill in the art will appreciate that any factor or cell involved in the biological cascade that results in EGF-R promoting goblet cell proliferation may be targeted for inhibition, e.g. TGF-α antagonists; inhibitors of mitogen-activated protein kinase kinase (MEK) p44/42 mitogen-activated protein kinase (p44/42$^{mapk}$); antioxidants; metalloproteinase inhibitors; inhibitors of MAP kinases; inhibitors of metalloproteinases that mediate release of membrane-bound EGFR ligand; inhibitors of G-protein-coupled receptors; and the like. Without being bound by theory, a cascade begins during an inflammatory response when cells such as mast cells or neutrophils release TNF-α, which then promotes EGF-R expression. Stimulation of EGF-R, e.g. by its ligand EGF, in turn triggers goblet cell proliferation. Thus, any cells or factors involved in the cascade, such as in the TNF-α pathway, may be targeted for antagonist activity.

The EGF-R antagonist administered in the therapeutic method may be in any form. By way of example, the EGF-R antagonist may be in the form of a small molecule (i.e., antisense oligonucleotide, tyrosine kinase inhibitor, etc.), antibodies or portion of antibodies that bind to EGF, TGFα or EGF-R. Preferred EGFR antagonists are selective, i.e. they inhibit their target factor to a greater degree than other factors of the same type. Selectivity may be enhanced by the methods of formulation and drug delivery, e.g. where the inhibitor is preferentially delivered to inflamed airways, etc.

Small Molecule EGF-R Antagonists

Tyrosine Kinase Inhibitors

Tyrosine kinase inhibitors that act on the EGF receptor, and that are selective for the EGF-R, are known in the art, and may be used in the subject methods. Examples are described above, and of such may include BIBX1522 (Boehringer Ingelheim, Inc., Ingelheim, Germany); CGP59326B (Novartis Corporation, Basel, Switzerland); tyrphostin AG1478 (Daub et al. (1997) *EMBO J.* 167032-7044; 4-aminoquinazoline EGF-R inhibitors (described in U.S. Pat. No. 5,760,041); substituted styrene compounds which can also be a naphthalene, an indane or a benzoxazine; including nitrile and molononitrile compounds (described in U.S. Pat. No. 5,217, 999); the inhibitors disclosed in U.S. Pat. No. 5,773,476; potato carboxypeptidase inhibitor (PCI), a 39-amino acid protease inhibitor with three disulfide bridges, (Blanco-Aparicio et al. (1998) *J Biol Chem* 273(20): 12370-12377); bombesin antagonist RC-3095 (Szepeshazi et al. (1997) *Proc Natl Acad Sci U S A* 94:10913-10918) etc. Other tyrosine kinase inhibitors include quinazolines, such as PD 153035, 4-(3-chloroanilino)quinazoline, or CP-358,774, pyridopyrimidines, pyrimidopyrimidines, pyrrolopyrimidines, such as CGP 59326, CGP 60261 and CGP 62706, and pyrazolopyrimidines (Shawn and Shawver, supra.), 4-(phenylamino)-7H-pyrrolo[2,3-d]pyrimidines (Traxler et al. (1996) *J. Med. Chem.* 39:2285-2292), curcumin (Korutla et al. (1994) *Biochim Biophys Acta* 1224:597-600); (Laxmin arayana (1995), *Carcinogen* 16:1741-1745); etc.

Preferred tyrosine kinase inhibitors are selective for EGF receptor, i.e. the EGF-R is inhibited to a greater degree than other cell surface receptors having tyrosine kinase activity. Selectivity is enhanced by the methods of formulation and drug delivery, e.g. where the inhibitor is preferentially delivered to inflamed airways, etc.

Inhibitors of Ligand-Independent EGFR Activation

Antagonists of ligand-independent mechanisms include anti-oxidants, such as super oxide dismutase, N-acetyl-L-cysteine, DMSO, DMTU, ascorbic acid, and the like. Ligand-independent activation of EGFR via oxidative stress results in activation of mitogen-activated protein kinase kinase (MEK) p44/42 mitogen-activated protein kinase (p44/42$^{mapk}$), resulting in mucin synthesis. Takeyama et al. (2000) *J. Immunol.* 164:1546-1552. This MEK activation is inhibited by the selective MEK inhibitor PD98059, as well as by antioxidants. Thus, MEK inhibitors and anti-oxidants may be used in therapeutic methods of the invention. MEK inhibitors which may be used in the therapeutic methods of the invention include any MEK inhibitor known in the art, including, but not limited to, PD98059; U0126; and MEK inhibitors described in WO 99/01421; WO 99/01426; WO 98/37881; WO 97/45412; and U.S. Pat. No. 5,525,625. Other inhibitors of the EGFR cascade which may be used in the methods of the invention include inhibitors of p38 MAP kinase, including, but not limited to, SB203580.

Metalloproteinase Inhibitors

Metalloproteinase inhibitors may be used in the therapeutic methods of the invention, particularly inhibitors of metalloproteinases that are involved in extracellular processing of a transmembrane EGFR ligand precursor, including, but not limited to, batimastat (BB-94) (Wojtowicz-Praga et al. (1997) *Invest. New Drugs* 15:61-75) and any of a wide variety of known metalloproteinase inhibitors, including, but not limited to, those described in Wojtowicz-Praga et al. (1997); Brown (1999) *APMIS* 107:174-180; as well as those described in, e.g., WO 200017162; U.S. Pat. No. 6,037,361; WO 200009485; WO 200006561; and WO 200006560. Whether an inhibitor is effective in inhibiting activation of EGFR by inhibiting a metalloproteinase that releases a transmembrane EGFR ligand precursor can be readily determined by those skilled in the art. As one non-limiting example, cells may be contacted with a stimulator of G-protein-coupled receptor (GPCR), including, but not limited to, LPA (lysophosphatidic acid), carbachol, thrombin, bombesin, and endothelin; EGF; phorbol ester (e.g., tetradecanoyl-phorbol-13-acetate, TPA); or ionomycin, in the presence or absence of a metalloproteinase inhibitor, and transactivation of EGFR measured as described in Prenzel et al. (1999, supra) or in the Examples section. Alternatively, an enzymatic assay of a metalloproteinase, particularly a batimastat-sensitive metalloproteinase, may be conducted. Those skilled in the art will readily appreciate that, in addition to specific or selective inhibitors of metalloproteinases, inhibition of any factor in this cascade may be used in the therapeutic methods of the invention, including, but not limited to, inhibitors (e.g., antagonists) of GPCR, particularly antagonists that induce goblet cell production.

Dosage

Typical dosages for systemic administration range from 0.1 µg to 100 milligrams per kg weight of subject per administration. Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound, for example with the in vitro and in vivo tests described herein.

Antibodies as EGF-R Antagonists

Antibodies as EGF-R antagonists are of particular interest (e.g. Viloria, et al., *American Journal of Pathology* 151:1523). Antibodies to EGF or EGF-R are produced by immunizing a xenogeneic immunocompetent mammalian host, including murine, rodentia, lagomorpha, ovine, porcine, bovine, etc. with EGF or EGF-R or portions thereof. Preferably human EGF or EGF-R or portions thereof are used as the immunogen. The choice of a particular host is primarily one of convenience. Immunizations are performed in accordance with conventional techniques, where the immunogen may be injected subcutaneously, intramuscularly, intraperitoneally, intravascularly, etc. into the host animal. Normally, from about 1.0 mg/kg to about 10 mg/kg of EGF or EGF-R intraperitoneally every other day will be used as an immunogen. The injections may be with or without adjuvant, e.g. complete or incomplete Freund's adjuvant, specol, alum, etc. After completion of the immunization schedule, the antiserum may be harvested in accordance with conventional ways to provide polyclonal antisera specific for EGF or the EGF-R.

Either monoclonal or polyclonal antibodies, preferably monoclonal antibodies, are produced from the immunized animal. Polyclonal antisera may be harvested from serum by conventional methods from the animals after completion of the immunization schedule. For production of monoclonal antibodies, lymphocytes are harvested from the appropriate lymphoid tissue, e.g. spleen, draining lymph node, etc., and fused with an appropriate fusion partner, usually a myeloma line, producing a hybridoma secreting a specific monoclonal antibody. Screening clones of hybridomas for the antigenic specificity of interest is performed in accordance with conventional methods.

Of particular interest are antibodies, preferably monoclonal antibodies, that bind to EGF-R or EGF so as to inhibit binding of EGF to EGF-R, e.g. an antibody that specifically binds to the extracellular domain of EGF-R thereby preventing binding of EGF. Such antibodies may be made by conventional methodology described above, or are commercially available. Examples of antibodies that would function as an EGF antagonist include, but are not limited to, the neutralizing anti-EGF-R monoclonal antibody C225 (KawamotoetaL. (1983) *Proc. Nat'l. Acad. Sci.* (*USA*) 80:1337-1341; Petit et al. (1997) *J. Path.* 151:1523-153, produced by ImClone Systems New York, N.Y.) and the anti-EGF-R monoclonal antibody EMD55900 (also called Mab 425), (Merck, Darmstadt, Germany).

The subject antibodies may be produced as a single chain, instead of the normal multimeric structure. Single chain antibodies are described in Jost et al. (1994) *J.B.C.* 269:26267-73, and others. DNA sequences encoding the variable region of the heavy chain and the variable region of the light chain are ligated to a spacer encoding at least about 4 amino acids of small neutral amino acids, including glycine and/or serine. The protein encoded by this fusion allows assembly of a functional variable region that retains the specificity and affinity of the original antibody.

Methods of humanizing antibodies are known in the art. The humanized antibody may be the product of an animal having transgenic human immunoglobulin constant region genes (see for example, International Patent Applications WO 90/10077 and WO 90/04036). Alternatively, the antibody of interest may be engineered by recombinant DNA techniques to substitute the CH1, CH2, CH3, hinge domains, and/or the framework residues with the corresponding human sequence (see WO 92/02190).

The use of Ig cDNA for construction of chimeric immunoglobulin genes is also known in the art (Liu et al. (1987) *P.N.A.S.* 84:3439 and (1987) *J. Immunol.* 139:3521). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) *Sequences of Proteins of Immunological Interest*, N.I.H. publication no. 91-3242. Human C region genes are readily available from known clones. The chimeric, humanized antibody is then expressed by conventional methods.

Antibody fragments, such as Fv, $F(ab)_2$ and Fab may be prepared by cleavage of the intact protein, e.g. by protease or chemical cleavage. Alternatively, a truncated gene is designed. For example, a chimeric gene encoding a portion of the $F(ab)_2$ fragment would include DNA sequences encoding the CH1 domain and hinge region of the H chain, followed by a translational stop codon to yield the truncated molecule.

An individual having a hypersecretory mucus disease may initially be administered amounts of EGF-R antagonist in the range of about 20 milligrams (mg) to about 400 mg per kilogram weight of patient twice daily, e.g. by inhalation.

Antisense Molecules as EGF-R Antagonists

In another embodiment, the subject therapeutic agents are antisense molecules specific for human sequences coding for EGF or EGF-R. The administered therapeutic agent may be antisense oligonucleotides, particularly synthetic oligonucleotides having chemical modifications from native nucleic acids, or nucleic acid constructs that express such anti-sense molecules as RNA. The antisense sequence is complementary to the mRNA of the targeted EGF or EGF-R genes, and inhibits expression of the targeted gene products (see e.g. Nyce et al. (1997) *Nature* 385:720). Antisense molecules inhibit gene expression by reducing the amount of mRNA available for translation, through activation of RNAse H or steric hindrance. One or a combination of antisense molecules may be administered, where a combination may comprise multiple different sequences from a single targeted gene, or sequences that complement several different genes.

A preferred target gene is EGF-R or EGF. The gene sequence may be accessed through public databases (human epidermal growth factor, Genbank accession no. K01166; human mRNA for precursor of epidermal growth factor receptor, Genbank accession no. X00588). Generally, the antisense sequence will have the same species of origin as the animal host.

Antisense molecules may be produced by expression of all or a part of the target gene sequence in an appropriate vector, where the vector is introduced and expressed in the targeted cells. The transcriptional initiation will be oriented such that the antisense strand is produced as an RNA molecule. The anti-sense RNA hybridizes with the endogenous sense strand mRNA, thereby blocking expression of the targeted gene. The native transcriptional initiation region, or an exogenous transcriptional initiation region may be employed. The promoter may be introduced by recombinant methods in vitro, or as the result of homologous integration of the sequence into a chromosome. Many strong promoters that are active in muscle cells are known in the art, including the β-actin promoter, SV40 early and late promoters, human cytomegalovirus promoter, retroviral LTRs, etc.

Transcription vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in cells, usually for a period of at least about one day, more usually for a period of at least about several days.

Alternatively, in a preferred embodiment, the antisense molecule is a synthetic oligonucleotide. Antisense oligonucleotides will generally be from about 7 to 500, usually from about 12 to 50 nucleotides, more usually from about 20 to 35 nucleotides, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996) *Nature Biotechnology* 14:840-844).

A specific region or regions of the endogenous sense strand mRNA sequence is chosen to be complemented by the antisense sequence. It has been shown that the 5' region of mRNA is particularly susceptible to antisense inhibition. However, recent evidence indicates analysis of mRNA secondary structure may be important in accessibility of sites to inhibition. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides may be chemically synthesized by methods known in the art (see Wagner et al. (1993) supra. and Milligan et al., supra.) Preferred oligonucleotides are chemically modified from the native phosphodiester structure, in order to increase their intracellular stability and binding affinity. A number of such modifications have been described in the literature, which alter the chemistry of the backbone, sugars or heterocyclic bases.

Oligonucleotides may additionally comprise a targeting moiety that enhances uptake of the molecule by cells. The targeting moiety is a specific binding molecules, e.g. an antibody or fragment thereof that recognizes molecules present on the surface of lung epithelial cells, particularly epithelial cells containing EGF-R.

Bispecific antibodies, chimeric antibodies and single chain antibodies are known in the art. Suitably prepared non-human antibodies can be humanized in various ways. Linkage between the oligonucleotide and targeting moiety may use any conventional method, for example by disulfide, amide or thioether bonds, depending on the chemistry of the oligonucleotide backbone. Preferably, the linkage will be cleaved inside the cell to liberate the oligonucleotide.

Oligonucleotides can be conjugated to hydrophobic residues, e.g. cholesterol, to protect from nucleases and to improve transport across cell membranes. Alternatively, conjugation to poly-L-lysine or other polyamines may also enhance delivery to the cell. A further modification that can be made is the addition of an intercalating component, such as acridine, capable of intercalating into the target mRNA and stabilizing the resultant hybrid. Antisense oligonucleotides may be transfected in combination with an enzyme(s) that will degrade antisense-mRNA complexes in the cell, e.g. RNase-H. Any protein or enzyme that can preferentially degrade or sequester the antisense-mRNA duplex may be similarly useful.

As an alternative to anti-sense inhibitors, catalytic nucleic acid compounds, e.g. ribozymes, anti-sense conjugates, etc. may be used to inhibit gene expression. Ribozymes may be synthesized in vitro and administered to the patient, or may be encoded on an expression vector, from which the ribozyme is synthesized in the targeted cell (for example, see International patent application WO 9523225, and Beigelman et al. (1995) *Nucl. Acids Res* 23:4434-42). Examples of oligonucleotides with catalytic activity are described in WO 9506764. Conjugates of anti-sense oligonucleotides with a metal complex, e.g. terpyridylCu(II), capable of mediating mRNA hydrolysis are described in Bashkin et al. (1995) *Appl Biochem Biotechnol* 54:43-56.

Pharmaceutical Formulations

EGF-R antagonists may be provided in solution or in any other pharmacologically suitable form for administration, such as a liposome suspension. The appropriate antibodies or other form of anti-EGF are formulated for administration in a manner customary for administration of such materials. Typical formulations are those provided in *Remington's Pharmaceutical Sciences*, latest edition, Mack Publishing Company, Easton, Pa. The route of administration will be selected based on the compound being administered, the status of the patient and disease that is being treated. Where there is hypersecretion of mucus, a compound may be administered through different routes depending on the severity of the disease, e.g. emergency situations may require i.v. administration, acute but not life threatening situation may be treated orally, while chronic treatment can be administered by aerosol.

For therapeutic use in nasal and airway diseases, local delivery is preferred. Delivery by inhalation or insufflating aerosols provide high level concentrations of drug compared to the concentration absorbed systemically. Alternatively, the EGF antagonist maybe administered by injection, including intramuscular, intravenous (IV), subcutaneous or peritoneal injection, most preferably IV and local injections. However, other modes of administration may also be used provided means are available to permit the EGF-R antagonist to enter the systemic circulation, such as transmucosal or transdermal formulations, which can be applied as suppositories, skin patches, or intranasally. Any suitable formulation that effects the transfer of the EGF-R antagonist to the bloodstream or locally to the lungs may properly be used.

For injection, suitable formulations generally comprise aqueous solutions or suspensions using physiological saline, Hank's solution, or other buffers optionally including stabilizing agents or other minor components. Liposomal preparations and other forms of microemulsions can also be used. The EGF-R antagonist may also be supplied in lyophilized form and reconstituted for administration. Transmucosal and transdermal administrations generally include agents that facilitate passage through the mucosal or dermal barrier, such as bile, salts, fusidic acid and its analogs, various detergents and the like. Oral administration is also possible, provided suitable enteric coatings are formulated to permit the EGF-R antagonist to survive the digestive tract.

The nature of the formulation will depend to some extent on the nature of the EGF-R antagonist chosen. A suitable formulation is prepared using known techniques and principles of formulation well known to those skilled in the art. The percentage of EGF-R antagonists contained in a particular pharmaceutical composition will also depend on the nature of the formulation; the percentage of an EGF-R antagonist that is an antibody will typically vary over a wide range from about 1% by weight to about 85% by weight.

There are many delivery methods known in the art for enhancing the uptake of nucleic acids by cells. Useful delivery systems include Sendai virus-liposome delivery systems (Rapaport and Shai (1994) *J. Biol. Chem.* 269:15124-15131), cationic liposomes, polymeric delivery gels or matrices, porous balloon catheters (as disclosed by Shi et al. (1994) *Circulation* 90:955-951; and Shi et al. (1994) *Gene Therapy* 1:408-414), retrovirus expression vectors, and the like.

The use of liposomes as a delivery vehicle is one method of interest for use with EGF-R antagonists. The liposomes fuse with the cells of the target site and deliver the contents of the lumen intracellularly. The liposomes are maintained in contact with the cells for sufficient time for fusion, using various means to maintain contact, such as isolation, binding agents, and the like. Liposomes may be prepared with purified proteins or peptides that mediate fusion of membranes, such as Sendai virus or influenza virus, etc. The lipids may be any useful combination of known liposome forming lipids, including cationic lipids, such as phosphatidylcholine. The remaining lipid will normally be neutral lipids, such as cholesterol, phosphatidyl serine, phosphatidyl glycerol, and the like. For preparing the liposomes, the procedure described by Kato et al. (1991) *J. Biol. Chem.* 266:3361 may be used.

In a preferred embodiment, the EGF-R antagonist is encapsulated in a sterically stabilized "stealth" liposomes, e.g. pegylated liposomes. When such liposomes are injected i.v., they remain in the circulation for long periods. Postcapillary venular gap junctions open during airway inflammation and allow fluid accumulation and permit molecules, e.g. complement, kininogen, to enter tissues, initiating inflammatory cascades. Such inflammation allows liposomes and their contents to be deposited selectively in the inflamed tissue (Zhang et al. (1998) *Pharm Res* 15:455-460).

EGF-R antagonists may be administered to the afflicted patient by means of a pharmaceutical delivery system for the inhalation route. The compounds may be formulated in a form suitable for administration by inhalation. The pharmaceutical delivery system is one that is suitable for respiratory therapy by topical administration of EGF-R antagonists thereof to mucosal linings of the bronchi. This invention can utilize a system that depends on the power of a compressed gas to expel the EGF-R antagonists from a container. An aerosol or pressurized package can be employed for this purpose.

As used herein, the term "aerosol" is used in its conventional sense as referring to very fine liquid or solid particles carries by a propellant gas under pressure to a site of therapeutic application. When a pharmaceutical aerosol is employed in this invention, the aerosol contains the therapeutically active compound, which can be dissolved, suspended, or emulsified in a mixture of a fluid carrier and a propellant. The aerosol can be in the form of a solution, suspension, emulsion, powder, or semi-solid preparation. Aerosols employed in the present invention are intended for administration as fine, solid particles or as liquid mists via the respiratory tract of a patient. Various types of propellants known to one of skill in the art can be utilized. Examples of suitable propellants include, but is not limited to, hydrocarbons or other suitable gas. In the case of the pressurized aerosol, the dosage unit may be determined by providing a value to deliver a metered amount.

The present invention can also be carried out with a nebulizer, which is an instrument that generates very fine liquid particles of substantially uniform size in a gas. Preferably, a liquid containing the EGF-R antagonists is dispersed as droplets. The small droplets can be carried by a current of air through an outlet tube of the nebulizer. The resulting mist penetrates into the respiratory tract of the patient.

A powder composition containing EGF-R antagonists or analogs thereof, with or without a lubricant, carrier, or propellant, can be administered to a mammal in need of therapy. This embodiment of the invention can be carried out with a conventional device for administering a powder pharmaceutical composition by inhalation. For example, a powder mixture of the compound and a suitable powder base such as lactose or starch may be presented in unit dosage form in for example capsular or cartridges, e.g. gelatin, or blister packs, from which the powder may be administered with the aid of an inhaler.

Combination therapies may be used to treat hypersecretory pulmonary disease. In particular, EGF-R antagonists may be combined with conventional treatment for alleviation of hypersecretion, such as bronchiodilators, corticosteroids, expectorants, mucolytica agents and the like to facilitate mucociliary clearance.

Depending on the condition of the patient, it may be preferable to delivery a formulation of the present invention by injection (e.g., intravenous) or by inhalation. Patients which have large amounts of mucus in the lungs cannot, in general, be treated initially by inhalation. This is due to the fact that the patient's lungs are sufficiently obstructed that inhaling aerosolized formulation into the lungs may not be particularly effective. However, after treating by injection or, alternatively, for long term maintenance or in situations where the patient's lungs are not severely obstructed, administration by inhalation is preferred. Administration by inhalation is preferred because smaller doses can be delivered locally to the specific cells which are most in need of treatment. By delivering smaller doses, any adverse side effects are eliminated or substantially reduced. By delivering directly to the cells which are most in need of treatment, the effect of the treatment will be realized more quickly.

There are several different types of inhalation methodologies which can be employed in connection with the present invention. Antagonists of the present invention can be formulated in basically three different types of formulations for inhalation. First, antagonists of the invention can be formulated with low boiling point propellants. Such formulations are generally administered by conventional meter dose inhalers (MDI's). However, conventional MDI's can be modified so as to increase the ability to obtain repeatable dosing by utilizing technology which measures the inspiratory volume and flow rate of the patient as discussed within U.S. Pat. Nos. 5,404,871 and 5,542,410.

Alternatively, the agonists of the present invention can be formulated in aqueous or ethanolic solutions and delivered by conventional nebulizers. However, more preferably, such solution formulations are aerosolized using devices and systems such as disclosed within U.S. Pat. Nos. 5,497,763; 5,544,646; 5,718,222; and 5,660,166.

Lastly, agonist compounds of the present invention can be formulated into dry powder formulations. Such formulations can be administered by simply inhaling the dry powder formulation after creating an aerosol mist of the powder. Technology for carrying such out is described within U.S. Pat. No. 5,775,320 issued Jul. 7, 1998 and U.S. Pat. No. 5,740,794 issued Apr. 21, 1998.

With respect to each of the patents recited above, applicants point out that these patents cite other publications in intrapulmonary drug delivery and such publications can be referred to for specific methodology, devices and formulations which could be used in connection with the delivery of agonists of the present invention. Further, each of the patents are incorporated herein by reference in their entirety for purposes of disclosing formulations, devices, packaging and methodology for the delivery of agonist formulations of the present invention.

Screening Assays

Candidate Drugs

Screening assays may be used to identify bioactive candidate agents that are EGF antagonists. Of particular interest are screening assays for agents that have a low toxicity for human cells. A wide variety of assays may be used for this purpose, including labeled in vitro protein-protein binding assays, electrophoretic mobility shift assays, enzyme activity assays, immunoassays for protein binding, and the like. The purified EGF or EGF-R protein may also be used for determination of three-dimensional crystal structure, which can be used for modeling intermolecular interactions, transporter function, etc.

The term "agent" as used herein describes any molecule, e.g. protein or pharmaceutical, with the capability of altering or inhibiting, directly or indirectly, the physiological function of EGF or EGF-R, including, but not limited to, directly altering or inhibiting EGF or EGFR receptor function; altering or inhibiting any factor in the EGFR cascade; altering or inhibiting any factor involved in activation of EGFR; and altering or inhibiting any factor involved in release of membrane-bound EGFR ligand. Generally, a plurality of assay mixtures is run in parallel with different agent concentrations to obtain a differential response to the various concentrations. Typically, one of these concentrations serves as a negative control, i.e. at zero concentration or below the level of detection.

Candidate agents encompass numerous chemical classes, though typically they are organic molecules, preferably small organic or inorganic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and anti-digoxin, etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

The compounds having the desired pharmacological activity may be administered in a physiologically acceptable carrier to a host for treatment of hypersecretory disease in formulations described herein. Depending upon the manner of introduction, the compounds may be formulated in a variety of ways described herein. The concentration of therapeutically active compound in the formulation may vary from about 0.1-100% by weight.

Dosage Regime

The appropriate dosage level will also vary depending on a number of factors including the nature of the subject to be treated, the particular nature of the hypersecretory condition to be treated and its severity, the nature of the EFGR antagonist used as active ingredient, the mode of administration, the formulation, and the judgement of the practitioner. For example, when antibodies are administered by themselves such as anti-EGF or EGF-R in an injectable formulation, the dosages will be in the range of 20 mg/kg to about 40 mg/kg at a single dosage. Repeated administration over a period of days may be required or administration by intravenous means may be continuous. For chronic conditions, administration may be continued for longer periods as necessary.

Efficacy of the dosing regime will be determined by assessing for improved lung function in the patient. This assessment may include viscoelasticity measurements of sputum, improvements in pulmonary function, including improvements in forced exploratory volume of sputum and maximal midexpiratory flow rate. The aforementioned therapeutic regime can be given in conjunction with adjunct therapies such as antibiotics, DNAse I or other current therapies for the treatment of hypersecretory pulmonary disease. If antibiotics are co-administered as part of the patient s therapy, bacterial quantitation following therapy can be included to assess the efficacy of the treatment by decreased bacterial growth, indicating decreased viscosity of mucus or sputum and increase of the mucus or sputum lung clearance.

Pulmonary function tests, as well as diagnostic tests for the clinical progression of pulmonary hypersecretory disease, are known to those individuals with skill in this art. Standard pulmonary function tests include airway resistance (AR); forced vital capacity (FVC); forced expiratory volume in 1 second (FEV(1)); forced midexpiratory flow; and peak expiratory flow rate (PEFR). Other pulmonary function tests include blood gas analysis; responses to medication; challenge and exercise testing; measurements of respiratory muscle strength; fibro-optic airway examination; and the like. Some basic procedures for studying the properties of mucus include rheology, e.g. with the use of a magnetic microrheometer; adhesivity to characterize the forces of attraction between an adherent surface and an adhesive system by measuring the contact angle between a mucus drop and a surface. Mucus transport by cilia can be studied using conventional techniques, as well as direct measurement, i.e. in situ mucus clearance. Transepithelial potential difference, the net result of the activity of the ion-transport system of the pulmonary epithelium, can be measured using appropriate microelectrodes. Quantitative morphology methods may be used to characterize the epithelial surface condition.

The patient to be treated can be a primate, such as a human, or any other animal exhibiting the described symptoms. While the method of the invention is especially adapted for the treatment of a human patient, it will be understood that the invention is also applicable to veterinary practice.

In Vitro Screening Assay

In another embodiment of this invention, in vitro assays are used to assess the therapeutic potential of candidate agents to inhibit goblet cell proliferation, i.e. whether such agents are active as an EGF antagonist. Generally, such assays will comprise the following steps: (i) contacting an in vitro model of goblet cell proliferation with EGF or the functional equivalent thereof; (ii) subsequently contacting the in vitro model with a candidate agent; and (iii) assessing goblet cell proliferation, wherein an inhibition of goblet cell proliferation is indicative of the candidate agent's therapeutic potential.

The assay is preferably carried out with two controls where a second cell group is not contacted with any compound and a third is contacted with EGF but not the candidate agent. Comparisons are then made to determine the degree of effect of EGF and the candidate agent on the cells.

Any in vitro model of goblet cell proliferation may be used. By way of example, rat tracheal cells can be isolated and maintained in culture as described in Guzman et al. (1995) 217:412-419. Briefly, the rat tracheal cells are plated onto collagen gel coated semipermeable membranes, initially cultured submerged in media, and subsequently maintained with an air/liquid interface. Examples of in vitro cells include primary human bronchial cells (available from Clonetics, San Diego); NCI-H292 cells (ATCC CRL-1848); and A431 cells (ATCC CRL-1555).

The in vitro culture is contacted with EGF and with a candidate agent. The candidate agent may be contacted with the culture prior to, concurrently with, or subsequently to the addition of EGF depending on the endpoint to be assessed and the nature of the candidate agent. The cultured cells are assessed for inhibition of goblet cell proliferation relative to controls.

A variety of molecular or biochemical markers may be used to assess goblet cell proliferation. Examples of molecular or biochemical markers that may be used include, but are not limited to, gene expression or protein expression characteristic of goblet cells. Certain mucin genes, e.g. MUC5B (Desseyn et al. (1997) J. Biol. Chem. 272:3168-3178) are expressed in the airway, and have a gene product highly represented in mucus. Expression of mucin genes provides a suitable marker for determining production of mucus.

Mucin gene expression may be assessed by conventional technology such as northern blot analysis, polymerase chain reaction (PCR), examination of the mucin gene promoter, or in situ analysis. Alternatively mucin proteins are assessed by conventional methodology, such as western blot analysis, ELISA, immunochemistry and the like, using detectably labeled antibodies. Morphological criteria may also be used to determine the presence or absence of goblet cells in the culture; such as staining for mucins using Alcian blue/PAS staining (Lou et al. (1998) Am. J. Respir. Crit. Care Med. 157:1927-1934). Antibodies to mucins can be examined using ELISA assays. Because stimulation of EGF-R by a ligand, e.g. EGF, TGF-α, induces phosphorylation of a specific EGF receptor kinase and results in goblet cell production, EGF-R phosphorylation can be measured as a reflection of goblet cell induction (Donato et al. (1984) J. Biol. Chem. 264:20474-20481).

A decrease in the molecular on biochemical markers associated with goblet cell proliferation is indicative of the therapeutic potential of the antagonist.

In Vivo Models

In yet another embodiment of the invention, in vivo animal models are used to assess the therapeutic potential of candidate agents to inhibit goblet cell proliferation. Generally the assay comprises the steps of: (i) creating an animal model of hypersecretory pulmonary disease by inducing EGF-R expression; (ii) stimulating the induced EGF-R to produce mucin producing goblet cells; (iii) treating with a candidate agent; and (iv) assessing goblet cell proliferation or mucus secretion, wherein an inhibition of goblet cell proliferation or mucus secretion is indicative of the candidate agent's therapeutic potential.

Any in vivo model of hypersecretory pulmonary disease may be used. By way of example an asthmatic mouse model, as described in Temann et al. (1997) Am. J. Respir. Cell. Biol. 16:471-478, and as shown in the examples provided herein. Alternatively, a rat model can be used, as described by Takeyama et al. (1998) Am. J. Physiol. Examples of other animal models that may be used include, but are not limited to Guinea pigs (a species that expresses goblet cells constitutively) and rats.

The lung tissue or tracheal tissue of the animal models may be assessed by the same molecular and biochemical markers described for the in vitro model. A decrease in goblet cell proliferation is indicative of the therapeutic potential of the EGF-R antagonist.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXPERIMENTAL

Example 1

The EGF System Regulates Mucin Production in Airways

Goblet cell hyperplasia occurs in various hypersecretory diseases of airways, but because the underlying mechanisms are unknown, no effective therapy exists. In healthy airways, goblet cells are few, but in hypersecretory airway diseases, goblet cell hyperplasia occurs. A human bronchial (NCI-H292) cell line was studied. These cells express EGF-R constitutively; EGF-R gene expression was further stimulated by tumor necrosis factor alpha (TNFα). EGF-R ligands increased the synthesis of mucins, and this effect was increased by co-incubation with TNFα.

Airway epithelial cells of pathogen-free rats expressed little EGF-R protein, but intratracheal instillation of TNFα (200 ng) induced EGF-R in basal, pre-goblet, and goblet cells, but not in ciliated cells; TNFα, EGF, or TGFα alone did not induce goblet cell production. However, instillation of TNFα, followed by EGF-R ligands resulted in an increased number of goblet and pre-goblet cells and a striking increase in Alcian blue/PAS-positive staining (reflecting mucous glycoconjugates) and mucin MUC5 gene expression. In sensitized rats, ovalbumin resulted in goblet cell production and EGF-R expression in airway epithelium. In NCI-H292 cells, in rats stimulated by TNFα followed by EGF-R ligands, and in the asthma model in rats, pretreatment with EGF-R tyrosine kinase inhibitor (BIBX1522) prevented goblet cell production in airways. These findings demonstrate a role for inhibitors of the EGF-R cascade in hypersecretory diseases of airways.

Methods

In Vitro Studies.

Cell culture. A human pulmonary mucoepidermoid carcinoma cell line, NCI-H292 cells, were grown in RPMI 1640 medium containing 10% fetal bovine serum, penicillin (100 U/ml), streptomycin (100 μg/ml) at 37° C. in a humidified 5% $CO_2$ water-jacketed incubator. When confluent, cells were incubated with EGF (recombinant human EGF, 25 ng/ml, Genzyme, Cambridge, Mass.), TGFα (recombinant human TGFα, 25 ng/ml, Genzyme), TNFα (recombinant human TNFα, 20 ng/ml, Genzyme), EGF (25 ng/ml) plus TNFα (20 ng/ml) or TGFα (25 ng/ml) plus TNFα (20 ng/ml) for 12 h, 24 h or 48 h. In inhibition studies with an EGF-R tyrosine kinase inhibitor, BIBX1522 (10 μg/ml, generously provided by Boehringer Ingelheim Inc., Ingelheim, Germany), cells were pretreated with BIBX1522 30 min before adding growth factors. After incubation, cells grown in a T-75 flask were used for total RNA extraction or protein extraction, and 8-chamber slides were used for Alcian blue/PAS-staining to visualize mucins.

Western blotting. Cells grown in T-75 flasks were lysed and scraped with PBS containing 1% Triton X, 1% sodium dioxycolate and PMSF (10 mg/ml). Total amount of protein was estimated by BCA protein assay reagent (Pierce, Rockford, Ill.). Cell lysates were boiled with Tricine sample buffer and 2% βME at 95° C. Proteins were separated by SDS-PAGE in 8% acrylamide gels. The resulting gels were equilibrated in the transfer buffer: 25 mM Tris-HCl, 192 mM glycine, 20% (vol/vol) methanol, pH 8.3. The proteins were then transferred electrophoretically to nitrocellulose membranes. The membranes were then incubated for 1 h in 5% fat-free skim milk in PBS containing 0.05% Tween 20. Then the membranes were incubated with monoclonal mouse anti-EGF-R antibody (1:100) at 4° C. overnight. Bound antibody was visualized according to standard protocols for avidin-biotin-alkaline phosphatase complex method (ABC kit, Vector Laboratories). As a positive control for EGF-R, cell lysates from A431 cells were used (20).

Immunocytochemical localization of EGF-R in NCI-H292 cells. Cells grown on 8-chamber slides were fixed with 4% paraformaldehyde for 1 h. To stain for EGF-R, PBS containing 0.05% Tween 20, 2% normal goat serum and 2 mM levamisole was used as diluent for the antibody. Sections were incubated with mouse monoclonal antibody to EGF-R (1:250) overnight at 4° C., and then washed 3 times with PBS to remove excess primary antibody. Cells were then incubated with biotinylated horse anti-mouse immunoglobulin (Vector Laboratories, Burlingame, Calif.) at 1:200 dilution for 1 h at room temperature. Bound antibody was visualized according to standard protocols for avidin-biotin-alkaline phosphatase complex method (ABC kit, Vector Laboratories, Burlingame, Calif.).

Probes. EGF-R mRNA expression was determined using the linearized pTRI-EGF-R-human probe template (Ambion, Austin, Tex.). This probe contains a 360 bp cDNA fragment of the human EGF-R gene, which spans exons 12-14. MUC5 gene expression was determined using human MUC5AC probe, which contains a 298 bp cDNA fragment of human MUC5AC gene (generously provided by Dr. Carol Basbaum).

Northern blotting. Total RNA was extracted from NCI-H292 cells grown in a T-75 tissue culture flask using Tri-Reagent (Molecular Research Ctr, Cincinnati, Ohio) in each condition. Total RNA (10 μg) was electrophoresed on 1% agarose/formaldehyde gel and transferred to a nylon membrane (Amersham, Arlington Heights, Ill.) by capillary blotting. The probes were labeled with $^{32}$P using the Random Primed DNA labeling kit (Boehringer Mannheim Corp., Indianapolis, Ind.). Blots were prehybridized at 42° C. for 4 h and then hybridized at 42° C. for 16 h with $^{32}$P-labeled specific cDNA probe. Hybridization solution contained 250 mM Tris-HCl (pH7.5), 5% SDS, 1% BSA, 1% polyvinyl-pyrrolidone, 1% Ficoll, and 0.5% sodium pyrophosphate. After hybridization, the membranes were washed twice with 2×SSC with 0.1% SDS for 30 min at room temperature, followed by two washes in 2×SSC with 0.1% SDS for 30 min at 50° C. and a rinse in 0.1×SSC with 0.1% SDS. Membranes were exposed to X-ray film.

In Vivo Studies.

The experimental animal protocol was approved by the Committee on Animal Research, University of California San Francisco. Specific pathogen-free male F344 Fisher rats, weighing 230-250 g (Simonsen Laboratories, Gilroy, Calif.), were maintained in a temperature-controlled (21° C.) room with standard laboratory food and water freely available.

Healthy rats. Rats were anesthetized with methohexital sodium (Brevital sodium, 50 mg/kg, i.p.; Eli Lilly & Co., Indianapolis, Ind.) and allowed to breathe spontaneously. To determine whether TNFα up-regulates EGF-R in airways, TNFα (200 ng, 100 μl) was instilled into the trachea and the animals were euthanized 24 h later. To examine whether EGF or TGFα induces goblet cells in airway epithelium, EGF (600 ng, 100 μl) or TGFα (rat synthetic TGFα, 250 ng, 100 μl; Sigma, St Louis, Mich.) was instilled into the trachea either alone or 24 h after the instillation of TNFα (200 ng, 100 μl), and the animals were euthanized 48 h later. In each study, sterile PBS (100 μl) was instilled into the trachea as control. To confirm whether mucin production occurred via activation of EGF-R, we examined the effect of an EGF-R tyrosine kinase inhibitor, BIBX1522 (dose estimated from studies using the inhibitor to prevent cancer growth). Rats were pretreated with BIBX1522 (3, 10 or 30 mg/kg, i.p.), 1 h before and 24 h after instillation of TGFα. The trachea and lungs were removed for examination 48 h after the instillation of TGFα.

Sensitized Rats

Sensitization. Rats were sensitized on days 0 and 10 with intraperitoneal injections of ovalbumin (10 mg, grade V; Sigma, St. Louis, Mo.), complexed with 100 mg of aluminum hydroxide in 0.5 ml of sterile saline. Rats then rested for 10 days. On day 20, ovalbumin was delivered directly into the trachea; animals were challenged with 100 μl of 0.1% ovalbumin in saline by intratracheal instillation three times (days 20, 22 and 24). Rats were euthanized either without challenge (day 20), or 48 h after the third challenge (day 26). This procedure induced goblet cell metaplasia. To block the goblet cell hyperplasia, sensitized rats were pretreated with an EGF-R tyrosine kinase inhibitor, BIBX1522. On days of ovalbumin challenge (days 20, 22 and 24), sensitized rats were pretreated with BIBX1522 (10 mg/kg, i.p., 1 h before the challenge) and then BIBX1522 was also instilled into the trachea together with ovalbumin (BIBX1522, $10^{-5}$ M, 100 μl). BIBX1522 was also injected i.p. every 24 h until the day before the rats were euthanized. After the animals were euthanized, the trachea was removed 48 h after the third challenge.

Tissue preparation. At preselected times during anesthesia, the systemic circulation was perfused with 1% paraformaldehyde in DEPC-treated PBS at a pressure of 120 mmHg. The trachea was then removed and placed in 4% paraformaldehyde for 24 h. After fixation, trachea and lungs were embedded in either JB-4 plus monomer solution A for cell analysis or O.C.T. compound (Sakura Finetek U.S.A., Inc., Torrance, Calif.) for immunohistochemistry and in situ hybridization. The embedded tissues were cut as cross sections (4 mm thick) and placed on slides.

Cell analysis. We counted the total number of epithelial cells by counting epithelial cell nuclei over 2 mm of the basal lamina with an oil immersion objective lens (×1000 magnification). The linear length of the basal lamina under each analyzed region of epithelium was determined by tracing the contour of the digitized image of the basal lamina. After instillation of stimuli, "developing" goblet cells form. These cells have Alcian blue/PAS-positive granules, but the size of granules is small, and the number of cytoplasmic granules is few. We call these "developing" goblet cells "pre-goblet cells", a stage before cells become mature goblet cells. Goblet cells are tall, cuboidal, goblet to low columnar in shape, with abundant Alcian blue/PAS-stained granules filling most of the cytoplasm between the nucleus and the luminal surface. Pre-goblet cells are defined as cells with smaller mucus-stained areas (<1/3 height in epithelium from basement membrane to luminal surface) or with sparsely and lightly Alcian blue/PAS-stained, small granules. Ciliated cells are recognized by their ciliated borders, lightly stained cytoplasm, and large round nuclei. Non-granulated secretory cells are columnar in shape and extend from the lumen to the basal lamina. The cytoplasm stains light pink color, and a few tiny PAS-positive and Alcian blue-negative granules are observed in the cytoplasm. Basal cells are small flattened cells with a large nucleus, located just above the basal lamina but not reaching the airway lumen.

Quantification of goblet cell production. Goblet cell production, was determined by the volume density of Alcian blue/PAS-stained mucosubstances on the mucosal surface epithelium using a semi-automatic imaging system described elsewhere (Weber et al. (1984) *Science* 224:294-297). We measured the Alcian blue/PAS-positive stained area and the total epithelial area and expressed the data as the percentage of the total area stained by Alcian blue-PAS. The analysis was performed with the public domain NIH Image program (developed at the U.S. National Institute of Health and available from the Internet by anonymous FTP from zippy.nimh.gov or on floppy disk from the National Technical Information Service, Springfield, Va., part number PB95-500195GEI).

Immunohistochemical localization of EGF-R in rat epithelium. The localization of EGF-R was examined using immunohistochemical staining with an antibody to EGF-R (Calbiochem, San Diego, Calif.) in frozen sections of rat trachea. After perfusion with 1% paraformaldehyde in PBS, tissues were placed in 4% paraformaldehyde in PBS for 1 h and then removed in 30% sucrose for cryoprotection overnight. Tracheas were embedded in O.C.T. compound (Sakura Finetek U.S.A., Inc., Torrance, Calif.) and frozen. Frozen sections (5 µm) were cut and placed on glass slides (Superfrost Plus, Fisher Scientific, Pittsburgh, Pa.). Immunostaining was performed similarly to the in vitro studies.

Probe Preparation. The cDNA for rat MUC5 was generously provided by Dr. Carol Basbaum. A 320 bp cDNA fragment of rat MUC5 was subcloned into the Xba/hindIII site of the transcription vector, pBluescript-SK(−) (Stratagene, La Jolla, Calif.). To prepare RNA probes for in situ hybridization, this recombinant plasmid containing the rat MUC5 cDNA fragment was linearized and transcribed in vitro with the T7 or T3 polymerase to obtain antisense or sense probe, respectively. The probes for in situ hybridization were generated in the presence of [$^{35}$S]UTP. After transcription, the cDNA template was digested with DNase, and radiolabeled RNA was purified via a Sephadex G-25 Quick Spin™ Column (Boehringer Mannheim, Indianapolis, Ind.) and precipitated in an ethanol/ammonium acetate solution. Before use, RNA probes were washed with 70% ethanol and diluted in 10 mM DTT.

In Situ Hybridization. Frozen sections (5 µm) were cut and placed on positively charged glass slides (Superfrost Plus, Fisher Scientific, Pittsburgh, Pa.,). Sections cut in close proximity were used for hybridization with sense and antisense probes. Alternate sections were used for Alcian blue/PAS staining. Specimens were refixed in 4% paraformaldehyde, rehydrated in 0.5×SSC, and then acetylated in triethanolamine with acetic anhydride. Hybridization was carried out with 2500-3000 cpm/µl of antisense or sense probe in 50% deionized formamide, 0.3 M NaCl, 20 mM Tris, 5 mM EDTA, 1×Denhardt's solution, 20 mM dithiothreitol, 10% dextran sulfate, 0.5 mg/ml yeast tRNA, and 0.5 mg/ml sonicated salmon sperm DNA at 55 oC overnight. Posthybridization treatment consisted of washes with 2×SSC, 1 mM EDTA, 10 mM β-mercaptoethanol at room temperature, incubation with RNase solution (20 mg/ml) for 30 min at room temperature, and further washes in 0.1×SSC, 1 mM EDTA, 10 mM β-mercaptoethanol at 55° C. for 2 h and then in 0.5×SSC at room temperature. Specimens were dehydrated, air-dried, and covered with Kodak NBT nuclear track emulsion (Eastman Kodak, Rochester, N.Y.) for autoradiography. After exposure for 7 to 21 d at 4° C., the slides were developed, fixed, and counterstained with hematoxylin (21).

Statistics. All data are expressed as mean ±SEM. One-way analysis of variance was used to determine statistically significant differences between groups. Scheffe's F test was used to correct for multiple comparisons when statistical significances were identified in the analysis of variance. A probability of less than 0.05 for the null hypothesis was accepted as indicating a statistically significant difference.

Results

Figure 1B:
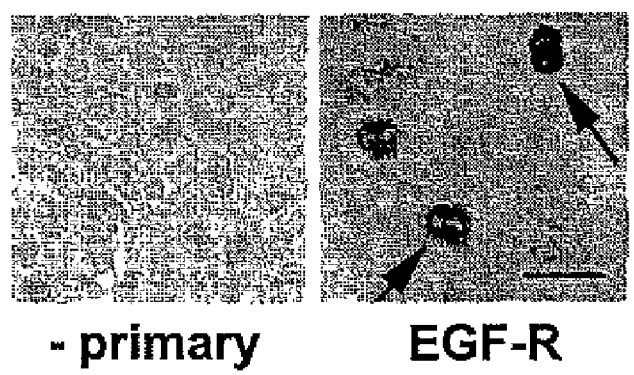
FIG. 1B, immunocytochemical analysis with anti-EGF-R antibody in cultures of NCI-H292 cells.
Figure 1C:
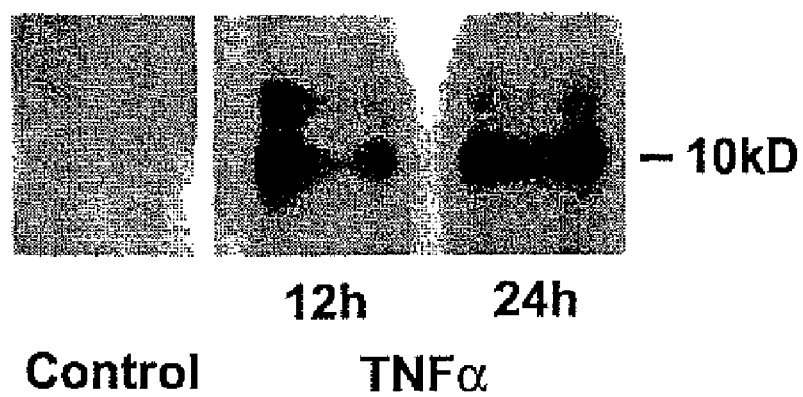
FIG. 1C, Northern analysis of EGF-R in NCI-H292 cells.

TNFα Stimulates Production of EGF-R in NCI-H292 Cells. First we determined whether NCI-H292 cells express EGF-R constitutively. Western analysis of immunoblots identified the presence of EGF-R protein in confluent cultures of NCI-H292 cells (FIG. 1A, right). Cells were examined after becoming confluent. Lysates were electrophoresed in 8% acrylamide gels and blotted with anti-EGF-R antibody. Molecular weights of marker proteins are reported on the right. A positive control for EGF-R was protein from A431 cells (FIG. 1A, left), which express EGF-R constitutively (Weber et al., supra.). Immunocytochemical studies with an anti-EGF-R antibody revealed positive staining, most striking in dividing cells (FIG. 1B, Immunocytochemical analysis with anti-EGF-R antibody in cultures of NCI-H292 cells). At confluence, positive staining was seen, most strongly in dividing cells (arrows, right side). In the absence of the primary antibody, staining was absent (left side). Northern blotting showed that TNFα (20 ng/ml) up-regulated EGF-R gene expression, an effect that was present at 12 h and increased at 24 h (FIG. 1C, Northern analysis of EGF-R in NCI-H292 cells). Analysis was performed on total RNA extracted from confluent cultures incubated with TNFα (20 ng/µl) for 12 or 24 h. The RNA was electrophoresed on a formaldehyde-agarose gel, transferred to a nylon membrane, and hybridized with the $^{32}$P-labeled EGF-R cDNA probe. After hybridization, the membrane was washed and autoradiographed.

EGF-R Ligands Stimulate Expression of Mucous Glycoconjugates and MUC5 Gene Expression in NCI-H292 Cells. EGF-R are expressed constitutively in NCI-H292 cells, so we assessed the ability of EGF-R ligands (EGF, TGFα) to induce the production of mucous glycoconjugates (FIG. 2, upper column, Alcian blue/PAS staining of NCI-H292 cells for identification of mucin glycoproteins). Upper column=incubation of cells without inhibitor; lower column=incubation in the presence of the EGF-R tyrosine kinase inhibitor BIBX1522 (10 µg/ml). When cells were incubated alone (control), some PAS-positive staining was seen (arrows, upper column); incubation with TNFα (20 ng/ml) alone did not affect the staining; incubation with EGF; (25 ng/ml) or with TGFα (25 ng/ml) increased the PAS-positive staining (arrows); incubation with TNFα plus TGFα increased markedly staining (arrow, upper column).

Some control cells showed staining; incubation with TNFα (20 ng/ml) alone did not affect staining; incubation with either EGF or with TGFα (each at 25 ng/ml) increased PAS-positive staining (arrows); incubation with TNFα plus TGFα increased the staining much more than either ligand alone. Thus, EGF-R ligands induce mucous glycoconjugates in NCI-H292 cells.

To examine MUC5 gene expression, Northern blotting was performed (FIG. 3). Total RNA (10 μg) was extracted from the cells, electrophoresed on a formaldehyde-agarose gel, transferred to a nylon membrane, and hybridized with the $^{32}$P-labeled MUC5 cDNA probe. After hybridization, the membrane was washed and autoradiographed. Cultures were obtained with medium alone (C), EGF or TGFα (25 ng/ml), TNFα (20 ng/ml), or the combination of TNFα plus either EGF or TGFα for 12 (upper column) or 24 h (lower column) on MUC5 gene expression. Cultures were also obtained with TNFα plus either EGF- or TGFa after preincubation with EGF-R tyrosine kinase inhibitor (BIBX1522; 10 μg/ml; lower column); the inhibitor prevented MUC5 gene expression.

NCI-H292 cells showed some expression in the control state (FIG. 3, lower left column); when the cells were incubated with EGF or TGFα, MUC5 gene expression was barely recognized at 12 h but was clearly expressed at 24 h. TNFα alone did not affect MUC5 gene expression, but when TNFα was added to the cells incubated with EGF-R ligands, MUC5 gene expression increased markedly above the level caused the EGF-R ligand alone (FIG. 3).

EGF-R Tyrosine Kinase Inhibitor (BIBX1522) Prevents Expression of Mucous Glycoconjungates and of MUC5 Gene Expression in NCI-H292 Cells. To test the hypothesis that activation of EGF-R receptors induces MUC5 gene expression, cells were incubated with an EGF-R tyrosine kinase inhibitor BIBX1522. When NCI-H292 cells were pretreated with BIBX1522 (10 μg/ml), PAS-positive staining was inhibited in the control state, and the increased staining that occurred with the EGF-R ligands was markedly inhibited (FIG. 2, lower column). On Northern analysis, MUC5 gene expression that was markedly increased by the combination of TNFα plus EGF or plus TGFα was completely inhibited by pre-incubation with BIBX1522 (FIG. 3, lower column). These results implicate activation of EGF-R in the induction of mucin gene and mucous glycoproteins in NCI-H292 cells.

TNFα Stimulates Production of EGF-R in Rats. Pathogen-free rats (which have few airway epithelial goblet cells constitutively) were studied, starting with the role of TNFα. In the control state, tracheal epithelium contained few EGF-R-positive cells (FIG. 4A, left). However, intratracheal instillation of TNFα (200 ng) induced EGF-R protein in various cell types in the tracheal epithelium (FIG. 4A, right). EGF-R-positive staining was present in goblet cells (G), pre-goblet cells (P-G), non-granulated secretory cells (S), and basal cells (Ba), but not in ciliated cells. Thus, TNFα induces EGF-R protein production.

Role of EGF-R Ligands in Production of Mucous Glycoconjugates and MUC5 Gene Expression in Rats. In the control state, tracheal epithelium contained few goblet and pre-goblet cells. Intratracheal instillation of EGF-R ligands, EGF (600 ng; not shown) or TGFα (250 ng; Table 1) alone had no effect on epithelial production of mucous glycoconjugates. However, when TNFα (200 ng) was given first, followed in 24 h by EGF or TGFα (Table 1), and the animals were euthanized 48 h later, Alcian blue/PAS staining was increased markedly, and the numbers of goblet and pre-goblet cells were markedly increased, without a change in the total number of cells or in the number of ciliated cells (Table 1). In situ hybridization for MUC5 gene showed no expression in control animals. When TNFα, followed by EGF or TGFα, was instilled intratracheally, expression of MUC5 was visible in the epithelium. Thus, induction of EGF-R alone or stimulation by EGF-R ligands alone was insufficient to induce goblet cell metaplasia or the production of mucous glycoconjugates. However, after the induction of EGF-R by TNFα, instillation of EGF-R ligands stimulated goblet cell metaplasia markedly.

TABLE 1

Cell Analysis in tracheal epithelium

| Cell type | control | TGFα | TNFα/TGFα | Ova sensitization i.p. only | Ova sensitization i.p. + i.t. |
|---|---|---|---|---|---|
| Goblet | 2.8 ± 0.7 | 5.8 ± 1.2 | 28.8 ± 3.4* | 5.4 ± 1.5 | 38.2 ± 6.3* |
| Pre-goblet | 7.8 ± 1.3 | 12.8 ± 1.6 | 44.8 ± 3.6* | 13.8 ± 1.4 | 36.0 ± 6.3* |
| Secretory | 82.0 ± 2.0 | 72.2 ± 4.0 | 40.8 ± 2.4* | 67.6 ± 7.0 | 49.8 ± 4.2 |
| Ciliated | 49.6 ± 2.0 | 54.6 ± 2.3 | 53.2 ± 1.8 | 56.4 ± 3.8 | 52.4 ± 7.1 |
| Basal | 57.8 ± 2.6 | 56.8 ± 2.3 | 43.0 ± 3.5 | 60.2 ± 3.4 | 59.8 ± 2.9 |
| Indeterminate | 1.4 ± 0.5 | 2.0 ± 0.4 | 0.8 ± 0.4 | 1.4 ± 0.2 | 2.6 ± 0.5 |
| Total | 201.4 ± 2.2 | 204.2 ± 3.3 | 211.4 ± 4.8 | 204.8 ± 6.6 | 238.8 ± 4.4* |
| % of AB/PAS-stained area | 2.4 ± 0.8 | 6.8 ± 1.9 | 35.8 ± 4.2* | 7.8 ± 2.9 | 38.7 ± 6.2* |

Table 1. Effect of mediators and of ovalbumin sensitization on tracheal epithelial cells in rats. Cells were analyzed as described in Methods; five rats per group. Characterization was aided by Alcian blue(AB)/PAS staining (which stains mucous glycoconjugates). In addition to counting of cells, percent of the total epithelial area occupied by AB/PAS-staining was calculated. Control airways and airways stimulated by TGFα (250 ng) alone contained few goblet and pre-goblet cells; there was little staining with AB/PAS. TNFα (200 ng), followed by TGFα, resulted in increased numbers of goblet and pre-goblet cells and an increase in the area occupied by AB/PAS-stained cells. Sensitization of rats with ovalbumin (OVA) intraperitoneally (ip) had no effect on cell distribution or on AB/PAS staining, but when OVA was given ip followed by intratracheal (it) instillation of OVA, a striking increase in goblet and pre-goblet cells and the percent area occupied by AB/PAS stain was found.

Ovalbumin Sensitization in Rats Induces EGF-R and Goblet Cell Production. Because death from acute asthma is reported to be due to mucous obstruction of airways, a model of asthma was produced in pathogen-free rats. Injections of ovalbumin (10 mg, ip) on days 0 and 10 did not stimulate goblet cell hyperplasia (Table 1). However, when this was followed by three intratracheal (i.t.) instillations of ovalbumin (0.1% in 100 μl) on days 20, 22, and 24, and the animals were euthanized on day 26, the numbers of goblet and pre-goblet cells were increased markedly; the numbers of ciliated and basal cells were unchanged (Table 1, right side). Immunohistochemical studies with an anti-EGF-R antibody showed no staining in control tracheas. Animals sensitized both i.p. and i.t. showed EGF-R staining (FIG. 4B, left) selectively in cells that stained positively with AB/PAS (FIG. 4B, right). After 3 intracheal instillations of ovalbumin (0.1%, 100 ml), EGF-R immunoreactivity was strongly expressed in goblet and pre-goblet cells (lower left), the same cells that stained positively with Alcian blue/PAS (lower right). Thus, an ovalbumin model of asthma showed goblet cell proliferation in cells that produced EGF-R.

EGF-R Tyrosine Kinase Inhibitor (BIBX1522) Prevents Goblet Cell Production Induced by Instillation of TNFα Plus EGF-R Ligands and by Ovalbumin Sensitization in Rats. Because BIBX1522 prevented mucin production in cultured cells, the effect of this inhibitor was examined in pathogen-free rats. Alcian-blue/PAS staining that was increased by tracheal instillation of TNFα followed by the EGF-R ligand TGFα, was inhibited in a dose-dependent fashion by pretreatment with BIBX1522 (3-30 mg/kg, ip; FIG. 5A). Tracheal instillation of TNFα (to induce EGF-R), followed by the EGF-R ligand TGFα, resulted in striking goblet cell metaplasia.

In rats sensitized with ovalbumin, pretreatment with BIBX1522 (10 mg/kg, ip) inhibited the production of goblet cells completely (evaluated by Alcian blue/PAS staining; FIG. 5B). Animals given ovalbumin i.p. only showed little AB/PAS-positive staining in bronchial epithelium. Animals first sensitized with OVA i.p., followed by three intratracheal (i.t.) instillations of OVA, showed a marked increase in AB/PAS-positive staining.

These studies indicate that EGF-R, when stimulated by EGF-R ligands, induce goblet cell production in vitro and in vivo, effects due to activation of EGF-R and which were blocked by an EGF-R tyrosine kinase inhibitor. In an ovalbumin model of asthma, the inhibitor was also effective in preventing goblet cell production.

In addition to describing a mechanism for inducing goblet cells, present results suggest a possible sequence for the evolution of goblet cell production based on the expression of EGF-R: Stimulation with TNFα induced intense staining of non-granulated secretory cells; their subsequent activation by EGF-R ligands caused progressive staining for mucous glycoconjugates in the cytoplasm, and the cells became "pre-goblet" and then "goblet" cells. Instillation of TNFα followed by EGF-R ligands induced goblet cell production without altering the total number of epithelial cells, suggesting that EGF-R activation promoted selective cell differentiation (not proliferation). The findings suggest that goblet cells are derived from non-granulated secretory cells that express EGF-R and are stimulated by EGF-R ligands to produce mucins.

In patients who die of acute asthma, goblet cell hyperplasia and mucous plugging are important findings. In a murine model of asthma, sensitization of airways occurs after repeated instillation of ovalbumin, resulting in marked airway goblet cell hyperplasia. We show that EGF-R, which is not expressed in control airway epithelium, is expressed in sensitized animals. Cells that stained were pre-goblet and goblet cells, suggesting that EGF-R was involved in goblet cell production. Pretreatment with an EGF-R receptor tyrosine kinase inhibitor (BIBX1522) prevented airway goblet cell production, confirming the role of EGF-R activation in goblet cell production in experimental asthma.

Present results implicate the EGF-R pathway in goblet cell hyperplasia. Previous studies have shown that various stimuli such as ozone, sulfur dioxide, viruses, lipopolysaccharide, platelet activating factor, and interleukin-4 up-regulate mucin expression and secretion. The present invention provides a mechanism to evaluate the relationship of these inflammatory stimuli and the EGF-R system.

Asthma serves as an example of the therapeutic strategy of the invention: Normal human airway epithelium has a ratio of 3-10 ciliated cells to each goblet cell. In asthma, the number of goblet cells can be equal or exceed ciliated cells; in patients who die in status asthmaticus, there is a 30-fold increase in the percentage area occupied by goblet cells compared with the number in patients dying of non-asthma respiratory diseases. Inhibition of production of goblet cells should eliminate this source of hypersecretion. Because the life cycle of goblet cells is unknown, the time course of resolution of goblet cell hyperplasia with treatment can not be predicted with precision. In the absence of further exposure to allergen, goblet cell hyperplasia in previously sensitized mice resolved within fifty days, along with other manifestations of allergic inflammation. Inhibition of EGF-R activation may inhibit goblet cell hyperplasia much more rapidly, depending on the life span of goblet cells. Recently, highly selective ATP-competitive tyrosine kinase inhibitors have been reported. EGF-R tyrosine kinase inhibitors are being evaluated for the treatment of malignancies associated with the expression of EGF-R.

Hypersecretion is a major manifestation in many chronic inflammatory diseases of airways. Presently, there is no effective therapy to relieve the symptoms and to halt the progression of these diseases. Present findings provide a mechanism and a strategy for therapy: by inhibiting EGF-R activation, goblet cell production is prevented. Inhibitors of EGF-R activation are proposed as therapy in hypersecretory airway diseases.

Example 2

Role of Oxidative Stress in Production of Goblet Cells

In humans, prolonged cigarette smoking has been suggested to be associated with progressive pathologic changes in peripheral airways including goblet cell hyperplasia. Likewise, experimental models of cigarette smoking in animals have been shown to cause goblet cell hyperplasia in airways. However, the mechanism by which cigarette smoke may induce mucin synthesis is unknown. The following data demonstrate that proinflammatory cytokine-activated neutrophils and cigarette smoke cause mucin MUC5AC synthesis in human bronchial epithelial cells via ligand-independent activation of EGF-R. These results implicate recruited neutrophils and cigarette smoke as regulators of epithelial cell differentiation that may result in abnormal induction of mucin-producing cells in airways.

Methods

Isolation of Neutrophils. Human neutrophils were purified from peripheral blood obtained from healthy human donors. Neutrophil isolation was performed by standard techniques of Ficoll-Hypaque gradient separation, dextran sedimentation, and hypotonic lysis of erythrocytes. Cells were routinely >95% viable by trypan blue dye exclusion. To prevent endotoxin contamination, all solutions were passed through a 0.1 μm filter.

Cell Culture. NCI-H292 cells, a human pulmonary mucoepidermoid carcinoma cell line, were grown in RPMI 1640 medium containing 10% fetal bovine serum, penicillin (100 U/ml), streptomycin (100 μg/ml) and Hepes (25 mM) at 37° C. in a humidified 5% $CO_2$ waterjacketed incubator. Either 6-well culture plates or 8-chamber slides were used to culture the cells. When confluent, cells were incubated for 1 h with neutrophils ($10^6$ cells/ml) alone, TNFα alone (recombinant human TNFα, 20 ng/ml, Genzyme, Cambridge, Mass.), IL-8 (recombinant human IL-8, $10^{-8}$ M, Genzyme) alone, fMLP ($10^{-8}$ M, Sigma, St. Louis, Mo.) alone, TNFα plus neutrophils, IL-8 plus neutrophils, fMLP plus neutrophils, hydrogen peroxide ($H_2O_2$, 200 μM), cigarette smoke solution or TGFα (recombinant human TGFα, 0.1-25 ng/ml, Calbiochem, San Diego, Calif.). The cells were then washed and incubated with fresh medium alone. Experiments were terminated at preselected times (for mRNA, 6 h and 12 h; for protein, 24 h). As controls, cells were incubated with medium alone for same time periods. In other studies with neutrophils, TNFα was chosen as a stimulus because it had the most potent effect on MUC5AC synthesis. NCI-H292 cells were incubated for 1 h with either neutrophils that had been incubated with TNFα (20 ng/ml) for 1 h and then washed with sterile PBS to avoid contamination with the supernatant (e.g., molecules released from neutrophils), or the NCI-H292 cells were incubated with supernatant only. In inhibition studies with EGF-R tyrosine kinase inhibitors, NCI-H292 cells were pretreated with BIBX1522 (10 μg/ml, generously provided by Boehringer Ingelheim Inc., Ingelheim, Germany) or tyrphostin AG1478 (10 μM, Calbiochem) 30 min before adding a stimulus. The effects of a selective inhibitor of platelet-derived growth factor receptor tyrosine kinase (tyrphostin AG1295, 100 μM, Calbiochem), and a negative control for tyrphostins (tyrphostin A1, 100 μM, Calbiochem) were also examined. In inhibition studies with blocking antibodies to EGF-R ligands, the supernatants were pretreated with anti-TGFα antibody (Calbiochem) or anti-EGF antibody for 30 min and then added to NCI-H292 cells. The role of oxygen free radicals was examined using scavengers of oxygen free radical DMSO (1%, Sigma), 1,3-dimethyl-2-thiourea (DMTU, 50 mM, Sigma), or superoxide dismutase (SOD, 300 U/ml, Sigma).

Preparation of Cigarette Smoke Solution. Research cigarettes (code2R1, produced for the University of Kentucky Tobacco and Health Research Foundation) were used in the study. Cigarette smoke solution was prepared as previously described (Dusser et al. (1989) *J. Clin. Invest* 84:900-906). In brief, cigarette smoke was withdrawn into a polypropylene syringe (35 ml) at a rate of one puff/min (10 times) and bubbled slowly into 20 ml of RPMI1640 containing 50 mM Hepes buffer. The smoke solution was then titrated to pH 7.4 and used immediately after preparation.

Visualization of Mucous Glycoconjugates and MUC5AC Protein in NCI-H292 Cells. At the end of experiments, the cells grown on 8-chamber slides were fixed with 4% paraformaldehyde for 1 h and then either stained with Alcian blue/periodic acid-Schiff (PAS) to visualize mucous glycoconjugates, or used for immunocytochemistry of MUC5AC. For immunocytochemistry of MUC5AC, PBS containing 0.05% Tween 20, 2% normal goat serum and Levamisol (2 mM) was used as diluent for the antibody. Cells were incubated with mouse mAb to MUC5AC (clone 45 M1, 1:200, Neo Markers, Fremont, Calif.) for 1 h at room temperature, and then washed 3 times with PBS to remove excess primary antibody. Cells were then incubated with biotinylated horse anti-mouse IgG (Vector Laboratories Inc., Burlingame, Calif.) at 1:200 dilution for 1 h at room temperature. Bound antibody was visualized according to a standard protocol for the avidin-biotin-alkaline phosphatase complex method.

In Situ Hybridization for human MUC5AC gene. A 298 bp cDNA fragment of human MUC5AC was inserted into TA cloning vector (Invitrogen, San Diego, Calif.). The preparation of RNA probes and in situ hybridization were performed as described above.

Immunoassay of MUC5AC Protein. MUC5AC protein was measured as described above. In brief, cell lysates were prepared with PBS at multiple dilutions, and 50 μl of each sample was incubated with bicarbonate-carbonate buffer (50 μl) at 40° C. in a 96-well plate (Maxisorp Nunc, Fisher Scientific, Santa Clara, Calif.), until dry. Plates were washed three times with PBS and blocked with 2% BSA (fraction V, Sigma) for 1 h at room temperature. Plates were again washed three times with PBS and then incubated with 50 μl of mouse monoclonal MUC5AC antibody (1:100) that was diluted with PBS containing 0.05% Tween 20. After 1 h, the wells were washed three times with PBS, and 100 μl horseradish peroxidase-goat anti-mouse IgG conjugate (1:10,000, Sigma) was dispensed into each well. After 1 h, plates were washed three times with PBS. Color reaction was developed with TMB peroxidase solution (Kirkegaard & Perry Laboratories, Gaithersburg, Md.) and stopped with 2N $H_2SO_4$. Absorbance was read at 450 nm.

Quantitative Analysis of TGFα Protein. TGFα protein was measured using a commercially available kit for ELISA (Sigma), following the manufacturer's instructions. Supernatant taken after incubation of neutrophils plus TNFα (20 ng/ml) for 1 h was mixed with the lysis buffer PBS containing 1% Triton X-100, 1% sodium deoxycholate and several protease inhibitors, (Complete Mini, Boehringer Mannheim, Germany), and then used to measure TGFα.

Immunoprecipitation for EGF-R Protein and Immunoblotting for Tyrosine Phosphorylation. Cells were serum-starved for 24 h and then stimulated with TGFα, $H_2O_2$, or the supernatant of activated neutrophils for 15 min. After stimulation, cells were lysed and incubated for 30 min in an orbital shaker at 4° C. To remove insoluble material, cell lysates were centrifuged at 14,000 rpm for 5 min at 4° C. Aliquots of supernatants containing equal amounts of protein were immunoprecipitated with anti-EGF receptor antibody (polyclonal, Ab4, Calbiochem) and 20 μl of protein A-agarose (Santa Cruz) for 2 h at 4° C. Precipitates were washed three times with 0.5 ml of lysis buffer, suspended in SDS sample buffer, and boiled for 5 min. Proteins were separated by SDS-PAGE in 8.0% acrylamide gel. The resulting gel was equilibrated in the transfer buffer: 25 mM Tris-HCl, 192 mM glycine, 20% (vol/vol) methanol, pH 8.3. The proteins were then transferred electrophoretically to nitrocellulose membranes (0.22 μm), blocked with 5% fat-free skimmed milk in PBS containing 0.05% Tween 20 overnight and then incubated with monoclonal anti-phosphotyrosine antibody (1:100, Santa Cruz) for 1 h. Bound antibody was visualized according to a standard protocol for the avidin-biotin-alkaline phosphatase complex method (ABC kit, Vector Laboratories).

Statistics. All data are expressed as mean ±SEM. One-way analysis of variance was used to determine statistically significant differences between groups. Scheffe's F test was used to correct for multiple comparisons when statistical significances were identified in the analysis of variance. A probability of less than 0.05 for the null hypothesis was accepted as indicating a statistically significant difference.

Results

Activated Neutrophils Cause Mucin MUC5AC Synthesis. When neutrophils plus stimuli that activate neutrophils (IL-8, fMLP, TNFα) were incubated with NCI-H292 cells for 1 h, MUC5AC protein synthesis increased significantly within 24 h, whereas non-stimulated neutrophils ($10^6$/ml), IL-8 alone or fMLP alone showed no effect on MUC5AC synthesis; incubation with TNFα alone caused a small, insignificant increase in MUC5AC synthesis. When neutrophils were preincubated for 1 h with TNFα, and then the neutrophils and their supernatant were separated, subsequent incubation of the supernatant for 1 h with NCI-H292 cells up-regulated MUC5AC gene expression within 12 h, and stimulated staining with both Alcian blue/PAS and with an antibody to MUC5AC protein within 24 h; resting NCI-H292 cells showed little expression of MUC5AC gene and small, patchy staining of both Alcian blue/PAS and MUC5AC protein. MUC5AC protein synthesis induced by the supernatant increased significantly from control; neutrophils separated from the supernatant after incubation were without effect. It was concluded that activated neutrophils rapidly secrete an active product, which causes MUC5AC synthesis.

EGF-R Tyrosine Kinase Inhibitors Prevent MUC5AC Synthesis Induced by Supernatant of Activated Neutrophils. Because EGF-R ligands are known to cause MUC5AC synthesis in NCI-H292 cells via activation of EGF-R tyrosine kinase, the role of EGF-R activation in MUC5AC synthesis induced by the supernatant of activated neutrophils was examined. Pretreatment of NCI-H292 cells with selective EGF-R tyrosine kinase inhibitors (BIBX1522, AG1478), prevented the MUC5AC protein synthesis that was usually induced by the supernatant of activated neutrophils. A selective platelet-derived growth factor receptor kinase inhibitor (AG1295) and a negative control for tyrphostins (A1) were without effect. These results implicate activation of EGF-R tyrosine kinase in MUC5AC synthesis induced by the supernatant of activated neutrophils.

Role of EGF-R Ligands Secreted in the Supernatant of Activated Neutrophils in MUC5AC Synthesis. To determine whether activation of EGF-R tyrosine kinase is dependent on the EGF-R ligands (EGF and TGFα), we preincubated the supernatant of activated neutrophils with neutralizing antibodies to EGF-R ligands. Pretreatment of the supernatant with either anti-TGFα antibody or anti-EGF antibody did not inhibit MUC5AC synthesis induced by the supernatant of activated neutrophils. Furthermore, TGFα was not detected in the supernatant. Thus, EGF-R tyrosine phosphorylation caused by the supernatant of activated neutrophils was induced by a mechanism independent of the EGF-R ligands, EGF and TGFα.

Cigarette Smoke and Oxygen Free Radicals Cause MUC5AC Synthesis. Cigarette smoke and the oxygen free radical, $H_2O_2$, up-regulated MUC5AC gene expression within 12 h, as did TGFα. Likewise, all stimuli increased MUC5AC protein synthesis and mucous glycoconjugate production within 24 h, effects that occurred in a dose-dependent fashion. The maximum MUC5AC synthesis in response to $H_2O_2$ was significantly less than the response to TGFα. Pretreatment with AG1478 prevented the increase in MUC5AC protein synthesis induced by all stimuli, indicating that the stimuli cause mucin synthesis by the activation of EGF-R tyrosine kinase. MUC5AC synthesis by supernatant of activated neutrophils, cigarette smoke and $H_2O_2$ were significantly inhibited by pretreatment with free radical scavengers (DMSO and DMTU) and SOD, but MUC5AC protein synthesis by TGFα was unaffected by DMSO or SOD.

Induction of Tyrosine Phosphorylation of EGF-R by Supernatant of Activated Neutrophils and by $H_2O_2$. The distribution of EGF-R protein was similar in serum-starved control and in all stimulated conditions (supernatant of activated neutrophils, cigarette smoke, $H_2O_2$ or TGFα). Total protein tyrosine phosphorylation occurred within 15 min after adding supernatant of activated neutrophils, cigarette smoke, $H_2O_2$ or TGFα; the serum-starved control showed no effect. TGFα-induced total protein tyrosine phosphorylation was greater than the effect of supernatant of activated neutrophils, cigarette smoke or $H_2O_2$. To determine whether the EGF-R was phosphorylated, immunoprecipitation with anti-EGF-R antibody was performed: The supernatant of activated neutrophils, the soluble products of cigarette smoke, and $H_2O_2$ all induced EGF-R-specific tyrosine phosphorylation within 15 min, an effect that was similar to that caused by TGFα. Pretreatment of NCI-H292 cells with AG1478 inhibited EGF-R tyrosine phosphorylation by all stimuli. DMSO inhibited supernatant-, cigarette smoke-, and $H_2O_2$-induced EGF-R tyrosine phosphorylation, but DMSO had no effect on TGFα-induced EGF-R tyrosine phosphorylation.

The above results show that neutrophils cause mucin MUC5AC synthesis in NCI-H292 cells when they are activated with IL-8, fMLP, or TNFα. Moreover, the supernatant that was collected 1 h after the incubation of neutrophils with TNFα caused MUC5AC synthesis, an effect that was inhibited by selective EGF-R tyrosine kinase inhibitors. Inhibition of EGF-R tyrosine kinase completely blocked MUC5AC synthesis caused by the supernatant of activated neutrophils; a non-EGF-R tyrosine kinase inhibitor, a selective platelet-derived growth factor receptor kinase inhibitor (AG1295) and a negative control for tyrphostins (A1) were without effect, implicating EGF-R tyrosine phosphorylation as the signaling pathway of MUC5AC synthesis induced by the supernatant of activated neutrophils.

To further analyze the mechanism by which supernatants of activated neutrophils induce EGF-R tyrosine phosphorylation, both ligand-dependent and ligand-independent EGF-R pathways were examined. First, we measured TGFα in the supernatant of activated neutrophils and found that the supernatant did not contain measurable amounts of TGFα. Previous reports showed that neutrophils only contained low concentrations (2.5 pg/$10^6$ cells) of TGFα. The effect of supernatant from activated neutrophils on MUC5AC synthesis was as potent as the effect of 1 ng of TGFα, which was 400-fold higher than the amount of TGFα found in neutrophils. Second, we performed blocking studies with neutralizing antibodies of EGF-R ligands: Pretreatment with neutralizing antibodies to EGF and TGFα failed to inhibit MUC5AC synthesis caused by the supernatant of activated neutrophils. These results suggest that neutrophil supernatant-induced MUC5AC synthesis was not due to the secretion of EGF-R ligands (TGFα and EGF) by neutrophils. Next, we examined the ligand-independent pathway: Because oxygen free radicals are known to be released by neutrophils during activation, and they are known to cause transactivation of EGF-R tyrosine kinase in various cells, we hypothesized that the release of oxygen free radicals by activated neutrophils caused EGF-R tyrosine phosphorylation and resulting MUC5AC synthesis in NCI-H292 cells. Scavengers of free radicals (DMSO and DMTU) and SOD inhibited MUC5AC synthesis by the supernatant of activated neutrophils. TNFα is reported to cause an oxidative burst in neutrophils in suspension, with a maximum response within 1 h; the present results show a similar time course.

In the present study, exogenous $H_2O_2$, a major product released from neutrophils during oxidative burst, caused MUC5AC synthesis in NCI-H292 cells. However, the maximum response to $H_2O_2$ in MUC5AC synthesis was only half of the response to TGFα. A significant finding in the present study is the fact that cigarette smoke alone caused MUC5AC synthesis. This suggests that cigarette smoke could cause MUC5AC synthesis in vivo both through direct stimulation and through indirect stimulation caused by recruitment of neutrophils. The exact molecules in cigarette smoke causing MUC5AC synthesis are still unclear. Cigarette smoke has been shown to contain multiple products (eg., nicotine, tar, acrolein and oxidants). In our experiments, DMSO and SOD partially inhibited MUC5AC synthesis induced by cigarette smoke. Thus, oxidant stress might be one mechanism producing this response. The fact that cigarette smoke-induced MUC5AC synthesis was completely blocked by EGF-R tyrosine kinase inhibitors indicates that EGF-R activation plays a principal role in cigarette smoke-induced MUC5AC synthesis.

In airway diseases, neutrophilic airway inflammation is a common feature, and neutrophils are recruited and activated by cytokines and by cigarette smoke. The present studies show that recruited neutrophils and cigarette smoke also act as regulators of epithelial cell differentiation that result in induction of mucin-producing cells in airways. Most importantly, inhibition of EGF-R activation will be useful as therapy in hypersecretory airway diseases.

Example 3

Wounding of Airway Epithelium Causes Goblet Cell Metaplasia

It was hypothesized that agarose plugs instilled into airways would lodge chronically in bronchi without obstructing them, and that resident plugs would cause inflammation, resulting in goblet cell metaplasia. It is shown that agarose plugs induce marked local production of goblet cells, as shown by Alcian blue/PAS-positive staining and mucin MUC5AC gene expression, associated with local recruitment of inflammatory cells. The results implicate EGF-R activation in plug-induced goblet cell metaplasia.

Methods

Animals. The experimental animal protocol was approved by the Committee on Animal Research of the University of California San Francisco. Specific pathogen-free, male F344 rats (230 to 250 g body weight; Simonsen Lab., Gilroy, Calif.) were used. The rats were housed in pathogen-free BioClean cages with environmentally controlled laminar flow hoods; animals had free access to sterile food and water.

Drugs. Drugs from the following sources were used: cyclophosphamide (Sigma, St. Louis, Mo.), methohexital sodium (Brevital, Jones Medical Industries, Inc., St. Louis, Mo.), pentobarbital sodium (Nembutal, Abbott Lab., North Chicago, Ill.); BIBX1522, a selective inhibitor of EGF-R tyrosine kinase (generously provided by Boehringer Ingelheim, Inc., Ingelheim, Germany), was dissolved in the following solution: 2 ml polyethylene glycol 400 (Sigma, St. Louis, Mo.), 1 ml 0.1 N HCl, and 3 ml 2% mannitol solution in water (pH 7.0). NPC 15669 (an inhibitor of leukocyte motility), was kindly provided by Scios Nova, Inc., Mountain View, Calif.

Agarose plugs. Agarose plugs (0.7-0.8 mm diameter) were made with 4% agarose type II medium EEO (Sigma, St. Louis, Mo.) in sterile phosphate-buffered saline (PBS). To visualize the agarose plugs in tissue, 3% suspension Monastral blue B (Sigma, St. Louis, Mo.) was added after melting the agarose at 50° C.

Protocol of experiments. We studied pathogen-free rats, because they normally have few goblet cells in airways. The animals were anesthetized with methohexital sodium (Brevital, 25 mg/kg, i.p.). The trachea was exposed aseptically with a midline cervical incision, and agarose plugs were instilled into a bronchus via a 20 gauge Angiocath (Becton Dikinson, Sandy, Utah) connected to polyethylene tubing (PE 90, internal diameter 0.86 mm and outer diameter 1.27 mm, Clay Adams, Parsippany, N.Y.) threaded into the incised trachea. The polyethylene tube was bent at a 30° angle to allow selective instillation into the right bronchus. After instillation, the incision was closed with a suture.

To evaluate the role of EGF-R on agarose plug-induced goblet cell metaplasia, animals were treated with BIBX1522 (80 mg/kg, i.p.) 1 h before instillation of the agarose plugs and repeated daily (40 mg/kg, i.p., bid). Animals were euthanized 24, 48 or 72 h after instillation of the agarose plugs.

To evaluate the role of TNFα in agarose plug-induced goblet cell metaplasia, animals were treated with a TNFα neutralizing antibody (Genzyme, Boston, Mass.). The first treatment (100 µl in 0.2 ml saline, i.p.) was given 1 h before the instillation of agarose plugs, and i.p. injections were repeated daily. In addition, TNFα neutralizing antibody was infused (10 µl/h) via an osmotic minipump (Alzet 2ML1, Alza Corp., Palo Alto, Calif.) implanted subcutaneously.

To study the effect of neutrophils on agarose plug-induced goblet cell metaplasia, rats were pretreated with cyclophosphamide (an inhibitor of bone marrow leukocytes) or with a combination of cyclophosphamide plus NPC 15669. Cyclophosphamide (100 mg/kg, i.p.) was given 5 d before instillation of agarose plugs, and a second injection of cyclophosphamide (50 mg/kg, i.p.) was given 1 d before instillation of plugs. In studies with NPC 15669, the drug (10 mg/kg, i.p.) was injected 1 h before instillation of agarose plugs, and then daily for 3 d thereafter.

All drugs (BIBX1522, TNFα neutralizing antibody, cyclophosphamide, and NPC 15669) were given i.p. 1 h before instillation of agarose plugs, and doses were repeated daily for 3 d.

Tissue preparation. At various times after agarose plug instillation, rats were anesthetized with sodium pentobarbital (65 mg/kg, i.p.), the systemic circulation was perfused with 1% paraformaldehyde in diethyl pyrocarbonate-treated PBS at a pressure of 120 mmHg. The right lung was removed, and the right caudal lobe was used for histology. For frozen sections, tissues were removed and placed in 4% paraformaldehyde for 1 h and then replaced in 30% sucrose for cryoprotection overnight. The tissues were embedded in O.C.T. compound (Sakura Finetek U.S.A., Inc., Torrance, Calif.). For methacrylate sections, the tissues were placed in 4% paraformaldehyde for 24 h and then dehydrated with graded concentrations of ethanol and embedded in methacrylate JB-4 (Polysciences, Inc., Warrington, Pa.). Tissue sections (4 µm thick) were stained with Alcian blue/PAS and counterstained with hematoxylin.

Morphometric analysis of bronchial epithelium. The percentage of Alcian blue/PAS-stained area of mucous glycoconjugates in the epithelium was determined using a semi-automatic image analysis system according to previously published methods. The area of epithelium and Alcian blue/PAS-stained mucous conjugates within the epithelium was manually circumscribed and analyzed using the NIH Image program (developed at the U.S. National Institutes of health and available from the internet by anonymous FTP or from a floppy disk from the National Technical Information Service, Springfield, Va.; part number PB95-500195GEI). The data are expressed as the percentage of the total epithelial area occupied by Alcian blue/PAS stain. To evaluate mucus secretion semi-quantitatively, the percentage of the length of epithelial surface occupied by Alcian blue/PAS-positive staining was determined by calculating the length that stained positively as a ratio to the total length. The percentage of denuded epithelium was determined by calculating the ratio of the length of denuded epithelium to the total epithelial length.

Identification of cell types in methacrylate sections and cell analysis. The total number of epithelial cells was determined by counting epithelial cell nuclei over 2 mm of the basal lamina with an oil immersion objective lens (×1000 magnification). The linear length of the basal lamina under each analyzed region of epithelium was determined by tracing the contour of the digitalized image of the basal lamina. The epithelial cells were identified as described previously. In brief, basal cells were identified as small flattened cells with a large nucleus, located just above the basal lamina but not reaching the airway lumen. The cytoplasm stained darkly, and Alcian blue or PAS-positive granules were not present. Ciliated cells were recognized by their ciliated borders, lightly stained cytoplasm, and large, round nucleus. Non-granulated secretory cells were columnar in shape and extended from the bronchial lumen to the basal lamina. After intrabronchial instillation of agarose plugs, "developing" goblet cells (pre-goblet cells) were formed. These cells showed Alcian blue/PAS-positive staining, the granules were small, and the cells were not packed with granules; they contained smaller mucous-stained areas (<⅓ height in epithelium from basement membrane to luminal surface) or sparsely and lightly Alcian blue/PAS-stained, small granules. Cells of indeterminate type are defined as cell profiles lacking sufficient cytoplasmic characteristics for proper categorization.

Immunohistochemical localization of EGF-R. The presence of EGF-R was determined by immunohistochemical localization, using a monoclonal mouse antibody to the EGF-R (Calbiochem, San Diego, Calif.). Previously prepared 4 μm frozen sections were post-fixed with 4% paraformaldehyde, treated with 0.3% $H_2O_2$/methanol. The tissues were incubated with EGF-R antibody (1:250 dilution). Biotinylated horse anti-mouse IgG (1:200; Vector Lab., Burlingame, Calif.), followed by streptavidin-peroxidase complex (ABC kit, Vector Lab., Burlingame, Calif.) was used to visualize antigen-antibody complexes stained with 3,3'-diaminobenzidine tetrahydrochloride (Sigma, St. Louis, Mo.). Negative control slides were incubated with either the primary or secondary antibody omitted and replaced with PBS.

In situ hybridization. [$^{35}$S]-labeled riboprobes were generated from a plasmid containing a 320 bp cDNA fragment of rat MUC5AC kindly provided by Dr. Carol Basbaum. Sections were hybridized with [$^{35}$S]-labeled RNA probes (2,500-3,000 cpm/μl hybridization buffer) and washed under stringent conditions, including treatment with RNase A. After autoradiography for 7-21 d, the photographic emulsion was developed, and the slides were stained with hematoxylin.

Counting of neutrophils in airway epithelium. Evaluation of neutrophil influx into bronchi was performed by staining neutrophils with 3-3'-diaminobenzidine tetrahydrochloride, and the number of neutrophils were counted in the airway lumen and in the epithelium; results were expressed as the number of stained cells per mm of basal lamina length.

Bronchoalveolar lavage (BAL). To assess differential cell counts in each group of animals, lungs were lavaged five times with 3 ml aliquots of sterile PBS, lavages were pooled, and the volume was measured. Cells in BAL were collected by spinning the lavage fluid at 1,000 rpm for 10 min. Ten microliters of a cell suspension was then counted with a hematocytometer to determine cell numbers in BAL fluid. Differential cell counts were performed on cytospun preparations stained with Diff-Quik (American Scientific Products, McGaw Park, Ill.). Differential cell counts were obtained by sampling at least 200 cells on each cytospun slide.

Statistical analysis. Data are expressed as means ±SE. For statistical analysis, the two-way or one-way analysis of variance (ANOVA) followed by Student t test was used as appropriate. A probability of less than 0.05 was considered a statistically significant difference.

Results

Effect on airway epithelial structure: Goblet cell metaplasia. To determine whether agarose plugs affect the structure of airway epithelium, agarose plugs were instilled into the right bronchus in 5 pathogen-free rats. In control animals, the bronchial epithelium contained few goblet cells. However, after local instillation of agarose plugs, Alcian blue/PAS staining showed a time-dependent increase in goblet cell area, which was detectable as early as 24 h and was greatest 72 h after instillation. At 24 h, agarose plugs produced significant increases in number of pre-goblet and goblet cells, and at 48 h more mature goblet cells were found (Table 1). At 72 h, agarose plugs increased the number of goblet cells (P<0.01); the numbers of basal and ciliated cells were not changed (P>0.05). The total number of epithelial cells per mm basal lamina 72 h after instillation was slightly but not significantly increased (P>0.05, Table 1); the height of the epithelium (measured from basement membrane to luminal surface of epithelium) was increased from 16.0±1.2 μm in control airways to 38.1±9.1 μm at 72 h after instillation of plugs (n=5, P <0.01).

In the airway lumen of control animals, there was no Alcian blue/PAS staining. However, adjacent to agarose plugs, positive staining was seen in the lumen, indicating that secretion of mucous glycoconjugates had occurred. In airways with agarose plugs, staining increased time-dependently. The percentage of the total length of epithelium occupied by Alcian blue/PAS-positive staining in airways adjacent to plugs increased from 0.1±0.1% in control animals to 4.7±1.4%, 13.3±0.7%, and to 19.1±0.7% at 24 h, 48 h, and 72 h (n=5). Furthermore, the agarose plugs denuded the epithelium of the plugged bronchus by 13.5±2.3%, 6.9±2.4%, and 5.1±1.5% of the total area at 24, 48, and 72 h, respectively (n=5).

Effect of agarose plugs on mucin gene expression. In control rats, there was no detectable signal with the antisense probe of MUC5AC in bronchi (n=4 per group). In bronchi where agarose plugs were instilled, there was a signal for MUC5AC that increased time-dependently from 24 to 72 h (n=4). MUC5AC gene expression was found preferentially in cells that stained positively with Alcian blue/PAS. No signals were detected in other cell types (e.g., smooth muscle, connective tissue). Sections examined with the MUC5AC sense probe showed no expression.

Effect of agarose plugs on EGF-R expression in airway epithelium. In control animals, immunostaining with an antibody to EGF-R showed sparse staining in epithelium. However, after instillation of agarose plugs, epithelium adjacent to agarose plugs showed EGF-R-positive staining in cells that stained positively with Alcian blue/PAS. The staining pattern for EGF-R paralleled the staining for MUC5AC and AB/PAS. Pre-goblet, goblet, and non-granulated secretory cells were immunopositive for EGF-R. Ciliated cells showed no immunoreactivity. In airways not obstructed by agarose plugs, the epithelium showed little staining for EGF-R and appeared similar to staining in control animals.

Effect of EGF-R tyrosine kinase inhibitor on goblet cell metaplasia and on mucin gene expression. In the present studies, instillation of agarose plugs resulted in the expression of EGF-R in the cells that produce mucins. EGF-R is a member of the class of tyrosine kinase receptors. Thus, when the EGF-R ligands (EGF or TGFα) bind to EGF-R, a specific EGF-R tyrosine kinase is activated. Therefore, to test the hypothesis that EGF-R activation induces expression of MUC5AC gene and of mucous glycoconjugates after instillation of agarose plugs, an EGF-R tyrosine kinase inhibitor (BIBX1522) was injected intraperitoneally in rats. BIBX1522 markedly inhibited agarose plug-induced Alcian blue/PAS-stained area of epithelium at 24, 48 and 72 h. It also completely inhibited the expression of MUC5AC gene at 72 h after plug instillation.

Effect of TNFα neutralizing antibody on goblet cell metaplasia and on EGF-R protein expression. We hypothesized that TNFα is released during the inflammation caused by agarose plugs. Therefore, we examined the effect of pretreatment of rats with a TNFα neutralizing antibody on agarose plug-induced goblet cell metaplasia: In animals pretreated with the TNFα neutralizing antibody (n=5), agarose plugs no longer stimulated EGF-R protein expression or the production of Alcian blue/PAS-positively stained (goblet) cells.

Inflammatory cell recruitment by agarose plugs. It was noted that agarose plugs cause epithelial damage and inflammatory cell infiltration. Various inflammatory cells can produce both TNFα and EGF-R ligands. Both EGF-R and its ligands are involved in the EGF-R cascade that leads to goblet cell metaplasia. We evaluated the roles of leukocytes and macrophages in agarose plug-induced effects in two ways. First, we examined cells in bronchoalveolar lavage: In control rats, macrophages were the predominant cells recovered (n=5; FIG. 4, Control). After instillation of agarose plugs, the number of macrophages increased ($P<0.05$), and significant numbers of neutrophils ($P<0.01$) appeared in the lavage fluid. The number of lymphocytes was unchanged.

Infiltrating cells were also evaluated in tissue sections: airways without agarose plugs contained few neutrophils, but airways containing plugs showed presence of neutrophils, both in the epithelium and in the lumen. The number of neutrophils in the airway lumen was 0.2±0.2, 42.4±7.1, 40.7±7.7, and 20.1±7.2/mm of basal lamina in control airways and at 24, 48, and 72 h after instillation of plugs, respectively ($P<0.05$, n=5). In addition, the number of neutrophils in airway epithelium was 1.3±0.4, 15.6±2.6, 14.9±1.4, and 14.8±2.6/mm of basal lamina in control and at 24, 48, and 72 h after instillation of plugs, respectively ($P<0.01$, n=5).

Effect of cyclophosphamide on neutrophil recruitment, goblet cell metaplasia, and EGF-R protein expression. In cyclophosphamide-treated rats, blood neutrophils were depleted (neutrophil count in venous blood after cyclophosphamide, 1.8±0.5%, n=5), and plug-induced neutrophil recruitment in BAL was inhibited. The number of neutrophils in the airway lumen (2.6±0.3/mm of basal lamina) and in the epithelium (0.8±0.2/mm) also decreased significantly at 24 h. Cyclophosphamide also inhibited agarose plug-induced goblet cell metaplasia and the expression of EGF-R protein. When the leumedin, NPC 15669 was added to cyclophosphamide, the inhibition of agarose plug-induced goblet cell metaplasia was similar to the effect of cyclophosphamide alone. These results implicate neutrophils in plug-induced goblet cell metaplasia.

Discussion

In the present study, we examined the effect of instillation of agarose plugs on goblet cell metaplasia in airways of pathogen-free rats, which have very few goblet cells in the control state. Epithelial cells in bronchi in control animals and bronchi without agarose plugs (control lungs) stained uniformly negatively with Alcian blue/PAS. Instillation of agarose plugs resulted in a profound, time-dependent increase in goblet cell area of bronchial epithelium adjacent to the instilled plugs, which was detectable within 24 h and was greatest approximately 72 h after instillation. Airways adjacent to plugged airways also stained positively with Alcian blue/PAS. The total cell number and the number of basal and ciliated cells did not change, but the number of goblet cells increased, and the number of non-granulated secretory cells decreased time-dependently after agarose plug instillation (Table 2). These results suggest that the goblet cell metaplasia was the result of conversion of non-granulated secretory cells to goblet cells.

TABLE 2

Effect of agarose plugs on the distribution of bronchial epithelial cells in pathogen-free rats*.

| Cell Type | Control | 24 h | 48 h | 72 h |
|---|---|---|---|---|
| Goblet | 0.0 ± 0.0 | 13.1 ± 5.6 | 25.7 ± 15.0 | 51.5 ± 9.0 |
| Pre-Goblet | 0.0 ± 0.0 | 32.8 ± 2.9 | 25.7 ± 15.0 | 51.5 ± 9.0 |
| Secretory | 43.5 ± 3.0 | 24.4 ± 3.3 | 18.4 ± 3.7 | 8.9 ± 2.3 |
| Ciliated | 98.5 ± 4.0 | 83.8 ± 7.9 | 81.6 ± 5.0 | 84.0 ± 3.9 |
| Basal | 18.4 ± 5.7 | 10.6 ± 0.8 | 11.6 ± 1.7 | 11.0 ± 2.3 |
| Indeterminate† | 1.3 ± 0.5 | 1.4 ± 0.8 | 1.1 ± 0.1 | 0.6 ± 0.4 |
| Total | 161 ± 7.2 | 166.1 ± 6.1 | 175.5 ± 6.2 | 180.9 ± 7.5 |

Cells were analyzed as described in Methods; n = 5 in each group. Characterization was aided by Alcian blue/PAS staining (which stains mucous glycoconjugates). Control airways contained few pre-goblet and goblet cells. After instillation of agarose plugs, there was a time-dependent (24, 48, 72 h) increase in the number of pre-goblet and goblet cells, and a decrease in the number of non-granulated secretory cells compared to control animals.
*Data are means ± SE, number of cells/mm basal lamina.
‡$P < 0.05$ compared to control.
§$P < 0.01$ compared to control.
Cells lack sufficient cytoplasmic characteristics for categorization.

Rat airway goblet cells are reported to express the MUC5AC gene. In the present studies, control bronchi did not express MUC5AC gene, but airways obstructed by plugs or adjacent to the plugs, which stained positively with Alcian blue/PAS, expressed the MUC5AC gene, suggesting that MUC5AC gene is involved in agarose plug-induced mucus production. These results indicate that agarose plugs induce the expression of mucin genes and the production of mucous glycoconjugates in selected cells in rat airways.

The mechanism of goblet cell metaplasia induced by agarose plugs was examined. EGF-R are not normally expressed in airway epithelium of pathogen-free rats but is induced by TNFα. In the presence of EGF-R in epithelium, instillation of EGF-R ligands (EGF or TGFα) results in an increase in mucin gene and protein expression. A selective inhibitor of EGF-R tyrosine kinase (BIBX1522) completely inhibits these responses, implicating EGF-R signaling in goblet cell metaplasia. The effect of BIBX1522 on agarose plug-induced goblet cell metaplasia was determined: BIBX1522 inhibited agarose plug-induced production of mucous glycoconjugates and MUC5AC gene expression. These results implicate an EGF-R cascade in agarose plug-induced goblet cell metaplasia.

The mechanisms by which the EGF-R cascade causes goblet cell metaplasia with agarose plugs were studied. First, we studied the expression of EGF-R protein in the bronchial epithelium. Control airways stained uniformly negatively for EGF-R, but airways containing agarose plugs showed selective, time-dependent positive staining for EGF-R. Positively stained cells included non-granulated secretory, pre-goblet, and goblet cells. Thus, agarose plugs induced EGF-R protein expression. Rats that were pre-treated with a neutralizing antibody to TNFα did not develop agarose plug-induced goblet cell metaplasia, implicating TNFα in agarose plug-induced EGF-R expression.

Cyclophosphamide, a drug that selectively depresses leukocyte production, prevented neutrophil recruitment into airway lavage fluid and into the airway epithelium following the instillation of agarose plugs and also prevented agarose plug-induced goblet cell metaplasia. Macrophages were also increased after the introduction of agarose plugs, but cyclophosphamide did not inhibit macrophage recruitment. These results implicate neutrophils in agarose plug-induced goblet cell metaplasia. The fact that cyclophosphamide also decreased EGF-R protein expression after agarose plugs suggests that neutrophils contribute, at least in part, to the EGF-R expression in this inflammatory condition.

Neutrophils are also capable of producing the EGF-R ligands, EGF and TGFα. In addition, epithelial cells are sources of EGF-R ligands, and there was striking denudation of epithelium adjacent to the agarose plugs. Thus, the epithelium could be an important potential source of both TNFα and EGF-R ligands.

It is reasonably assumed that the effective stimulus of the agarose plug is related to movement of the plugs during breathing, with subsequent epithelial abrasion. Mechanical injury to airway epithelium has been reported to cause hypersecretion. These prior studies lend credence to the hypothesis that mechanical trauma to the airway epithelium leads to hypersecretion. Orotracheal intubation is reported to result in abundant mucus secretion in horses. Chronic intubation in patients could cause mucous hypersecretion and could be responsible for mucous plugging. Inhibitors of EGF-R tyrosine kinase could serve to prevent mucous hypersecretion after tracheal intubation.

Epithelial damage is a common finding in studies of patients even with mild asthma, and the damage is increasingly related to worsening of clinical symptoms. Epithelial damage produced by the allergic response may induce EGF-R activation, which results in abnormal goblet cell production. The data presented above implicate EGF-R activation in a different response, specifically involving goblet cell metaplasia. Mechanical epithelial damage and epithelial injury in asthma may involve a similar (EGF-R) cascade, resulting in abnormal growth of epithelial secretory cells. This provides a mechanism for the hypersecretion that occurs in fatal cases of acute asthma.

Example 4

Regranulation of Goblet Cell by EGF-Receptors

Degranulation of goblet cells in rat nasal respiratory epithelium was induced by intranasal inhalation of fMLP. Significant degranulation was induced in the nasal septal epithelium 4 h after intranasal inhalation of fMLP ($10^{-7}$M). Goblet cell regranulation occurred by 48 h after inhalation. In the control state, MUC5AC protein was expressed in the goblet cells, but EGF-R protein was not expressed. Both EGF-R and MUC5AC mucin gene and protein were absent in control epithelium but were expressed significantly 48 h after inhalation. Pretreatment with an EGF-R tyrosine kinase inhibitor, BIBX1522, inhibited mucin MUC5AC gene and protein expression following fMLP-induced goblet cell degranulation. These results indicate that EGF-R expression and activation are involved in regranulation of goblet cell in rat nasal epithelium.

Methods

Animals. The experimental animal protocol was approved by the Committee on Animal Research of the University of California San Francisco. Specific pathogen-free male F344 rats (200 to 230 g body weight; Simonsen Lab, Gilroy, Calif.) were used. The animals were housed in pathogen-free Bio-Clean cages with environmentally controlled laminar flow hoods; animals had free access to sterile food and water.

Nasal Tissue Preparation. At various times after inhalation, rats were anesthetized with pentobarbital sodium (65 mg/kg, i.p.). The heart of the animal was exposed, a blunt-ended needle was inserted from the apex of the left ventricle into the ascending aorta, and the systemic circulation was perfused with 1% paraformaldehyde. An incision in the right atrium provided an outlet for the fixative. The eyes, lower jaws, skin, and musculature were removed, and the head was immersed in a large volume of the same fixative for 24 h. After fixation, the head was decalcified with Surgipath (Decalcifier II, Surgical Medical Industries, Inc., Richmond, Ill.) for 4-5 days and rinsed in phosphate-buffered saline. The nasal cavity was sectioned transversely at the level of the incisive papilla of the nasal palate. The frontal tissue block was embedded in glycol methacrylate (JB 4 Plus, Polysciences, Inc., Warrington, Pa.), or in OCT compound (Sakura Finetek, U.S.A., Inc., Torrance, Calif.) for frozen sections. Five µm-thick sections were cut from the anterior surface of glycol methacrylate-embedded blocks and stained with either Alcian blue (pH 2.5)/periodic acid-Schiff (AB/PAS) to demonstrate acid and neutral glycoconjugates, or 3,3'-diaminobenzidine (Sigma chemical, St. Louis, Mo.) to visualize leukocytes that had migrated into the epithelium. Five µm-thick sections were cut from the anterior surfaces of frozen-embedded blocks and stained with AB/PAS or used for immunostaining of EGF-R and MUC5AC.

Counting of Neutrophils in Nasal Epithelium. Neutrophils were counted in high powerfields of the epithelial layer stained with 3,3'-diaminobenzidine at magnification ×400. The number of neutrophils within the nasal sepal epithelium (from the basement membrane to cell apices) was determined by counting the number of nuclear profiles per unit of basal lamina length.

Quantification of Goblet Cell Degranulation and Regranulation. To assess goblet cell degranulation and regranulation, we measured the volume density of Alcian blue/PAS-stained mucosubstances on the mucosal surface epithelium using a semiautomatic imaging system according to a previously published method. We examined the stained slides with an Axioplan microscope (Zeiss, Inc.), which was connected to a video camera control unit (DXC7550MD; Sony Corp. of America, Park Ridge, N.J.). Images of the nasal epithelium were recorded in high power fields with a phase contrast lens at ×400, using an IMAXX Video System (PDI, Redmond, Wash.). The intracellular mucin in superficial epithelial secretory cells appears as oval-shaped, purple granules of varying sizes. We measured Alcian blue/PAS-positive-stained area and total epithelial area, and we expressed the data as the percentage of Alcian blue/PAS area to total area. The analysis was performed on a Macintosh 95001120 computer (Apple Computer, Inc., Cupertino, Calif.), using the public domain NIH Image program.

Immunolocalization of EGF-R and MUC5AC protein. Frozen sections from the paraformaldehyde-fixed nasal tissues were treated with 3% $H_2O_2$/methanol to block endogenous peroxide and were incubated with a mouse monoclonal antibody to EGF-R (Calbiochem, San Diego, Calif.), or MUC5AC (NeoMarkers Inc., Fremont, Calif.) for 1 h at a dilution of 1:100. Immunoreactive EGF-R or MUC5AC was visualized with the Vectastain Elite ABC kit (Vector Lab., Inc., Burlingame, Calif.) using 3,3-diaminobenzidine tetrahydrochloride as a chromogen. Controls included the substitution of primary or secondary antibody with PBS.

Methods. We studied pathogen-free rats, which normally have many goblet cells in the nasal septal epithelium. To determine the effect of aerosolized fMLP on goblet cell degranulation and on neutrophil migration into nasal mucosa epithelium, the animals were anesthetized with sodium pentobarbital (65 mg/kg, i.p.), and they received N-formyl-methionyl-leucyl-phenylalanine (fMLP; $10^{-5}$ M, Sigma, St. Louis, Mo.) in pyrogen-free saline intranasally by aerosol for 5 min. Aerosol exposure was accomplished by ventilating the animals with an ultrasonic nebulizer (PulmoSonic, DeVilbiss Co., Somerset, Pa.) that generated an aerosol mist at rate of 0.3 ml/min. Similarly, control animals were given saline aerosol alone intranasally.

To study regranulation of nasal goblet cells after inhalation of fMLP aerosol, the rats were euthanized 48 h after intranasal delivery of fMLP.

To evaluate the effect of EGF-R tyrosine kinase activation on goblet cell re-granulation, animals were pretreated intraperitoneally with an EGF-R tyrosine kinase inhibitor (BIBX1522,15 mg/kg, generously provided by Boehringer Ingelheim Inc., Ingelheim, Germany) 30 min before the inhalation of fMLP and repeated twice a day.

Statistics. All data are expressed as mean ±SEM. The one-way ANOVA or student t test was used for each experimental group. A probability of less than 0.05 was considered a statistically significant difference.

Results

Effect of goblet cell degranulation by fMLP on nasal epithelial structure. In the control state, the nasal septal epithelium contained a significant area of AB/PAS-stained goblet cells, but the luminal surface was unstained. Immunostaining for mucin MUC5AC protein corresponded to the area of AB/PAS staining, but in situ hybridization showed little or no MUC5AC gene expression. Immunohistochemical staining for EGF-R protein was negative. These results indicate that control rat nasal epithelium contains intact goblet cells containing MUC5AC protein in the absence of expression of the mucin gene. The absence of luminal staining suggests that degranulation (secretion) of mucins was not present.

It was hypothesized that non-stimulated rat nasal epithelium contains "stable", non-degranulating goblet cells containing mucin proteins. Neutrophil chemoattractants (e.g., fMLP) have been shown to recruit neutrophils into the airway epithelium, where they cause GC degranulation via an elastase-dependent process. To examine the effect of GC degranulation, an aerosol of the neutrophil chemoattract, fMLP ($10^{-7}$M) was delivered intranasally for 5 min. In rats euthanized 4 h after fMLP, the AB/PAS-stained area and the area of MUC5AC-positive immunostaining were markedly decreased and neutrophil recruitment into the nasal epithelium occurred. AB/PAS staining was prominent on the nasal airway luminal surface, confirming that GC degranulation had taken place. At 4 h after fMLP, however, MUC5AC gene expression was unchanged.

In rats euthanized 48 h after fMLP, immunohistochemical staining with an EGF-R antibody stained positively for EGF-R in pre-goblet and goblet cells the area of AB/PAS- and MUC5AC-immunopositive staining returned to the level present in the control state, indicating that regranulation of the nasal GC had occurred. At this time, neutrophil recruitment was no longer present; MUC5AC gene expression was visible in the area occupied by the GC, indicating that the GC regranulation was associated with increased mucin gene expression.

Role of EGF-R tyrosine kinase phosphorylation in goblet cell regranulation. Previous studies in rats reported that activation of EGF-receptors (EGF-R) leads to mucin gene and protein expression. To test the hypothesis that EGF-R activation plays a role in rat nasal GC regranulation after fMLP, rats were pretreated (n=5) with the selective EGF-R tyrosine kinase inhibitor, BIBX1522; aerosolization of fMLP caused neutrophil recruitment into the nasal epithelium and GC degranulation, but 48 h later the areas of AB/PAS staining and MUC5AC-immunopositive staining remained decreased. These results implicate EGF-R activation in nasal GC mucin synthesis following degranulation by fMLP.

In the present study, we examined the regulation of mucin production in rat nasal epithelium. Control epithelium contained a significant number of goblet cells, and MUC5AC protein was present in these cells. However, MUC5AC gene expression was absent. MUC5AC mucin expression is reported to occur in other airway epithelial cells via the expression of EGF-R and their activation. In control rat nasal epithelial cells, we found no EGF-R gene or protein expression. There was no luminal staining for AB/PAS or MUC5AC protein, suggesting that significant goblet cell degranulation (secretion) was not taking place. EGF-R might be down-regulated in "stable" goblet cells, preventing further mucin synthesis. Therefore, we "challenged" the nasal goblet cells by inducing goblet cell degranulation, and we examined the subsequent changes in airway epithelial structure.

Neutrophil chemoattractants cause neutrophil-dependent goblet cell degranulation in guinea pig and human airways mediated by neutrophil elastase, involving close contact between neutrophils and goblet cells. To induce the degranulation of normally present goblet cells in the nasal septum, the chemoattractant, fMLP was inhaled intranasally. fMLP recruited neutrophils in the nasal epithelium, followed by degranulation of the goblet cells; Alcian blue/PAS-stained area decreased markedly.

Next, we examined the subsequent events in the nasal epithelium after fMLP-induced GC degranulation. At 4h after fMLP, when maximum degranulation of nasal GC occurred, EGF-R and MUC5AC expression remained absent. However, 48 h after fMLP, EGF-R was strongly expressed in pregoblet and goblet cells. MUC5AC gene expression was now strongly expressed in the epithelium, and these events were associated with regranulation of the goblet cells (increased AB/PAS and MUC5AC staining). In fact, 48 h after fMLP, regranulation had occurred to the point that the goblet cell area was similar to the control state. These findings suggest that GC degranulation leads to expression and activation of EGF-R, thus inducing mucin MUC5AC expression.

To examine the role of EGF-R tyrosine kinase activation in GC regranulation, we pretreated animals with a selective EGF-R tyrosine kinase inhibitor, BIBX1522. In animals pretreated with BIBX1522, fMLP still caused GC degranulation. However, pretreatment with BIBX1522 prevented the regranulation of the GC and their expression of MUC5AC protein. These results implicate EGF-R activation in the regrowth of mucins after GC degranulation. In pathogen-free rats goblet cells are "inactive" (ie, not degranulating) and EGF-R are down-regulated. When inflammation (eg, stimulation of neutrophil infiltration) causes GC degranulation and mucin secretion, up-regulation and activation of EGF-R resupplies the airway epithelium with mucins. The present findings suggest that selective EGF-R tyrosine kinase inhibitors may be useful in preventing hypersecretion in nasal disease.

Example 5

Relationship of EGF-R to Goblet Cell Production in Human Bronchi

EGF-R expression was assessed in normal human airways and in asthmatic airways. In situ hybridization and immunohistochemical analysis for both EGF-R and MUC5AC (as a marker of goblet cell mucin) was performed.

Methods

Subjects

Samples from eleven healthy and twelve asthmatic subjects were analyzed. The subjects were characterized by spirometry, airway reactivity to inhaled methacholine, and skin test reactivity, as summarized in Table 3, below. FEV1: forced expired volume in one second; FEV1 $PC_{20}$: provocative concentration of methacholine required to cause a 20% decrease in baseline FEV1.

TABLE 3

| Characteristics | Healthy subjects (n = 11) | Asthmatic subjects (n = 12) |
| --- | --- | --- |
| Mean age (years) | 28 | 33 |
| Age range (years) | 24-44 | 26-37 |
| Gender (male/female) | 2/9 | 8/4 |
| FEV1 (% predicted) ± SE | 104 ± 7.1 | 84.2 ± 5.0 |
| FEV1 $PC_{20}$ (mg/ml) ± SE | >15 | >0.72 ± 0.2 |

Healthy subjects had no clinical history of airway obstruction or perennial rhinitis, and had normal pulmonary function test results. They also had no skin allergies. Asthmatic subjects met clinical diagnostic criteria for asthma (American Thoracic Society (1987) *Am. Rev. Respir. Dis.* 136:225-244), and showed hyperreactivity to inhaled methacholine. None of the subjects had taken inhaled or oral corticosteroids in the six weeks prior to enrollment in the study. The asthmatic subjects used β-agonists intermittently for symptom control. Among the subjects, there were no current or previous smokers, no history of endotracheal intubation within the past 5 years, respiratory tract infection within the past 6 weeks, or significant cardiac or neurologic disease.

A bronchoscope was introduced via the mouth and advanced to the right main stem bronchus. Biopsies were obtained from the bifurcations of the upper lobe, middle lobe, and superior segment of the lower lobe, using a spiked, fenestrated biopsy forceps. Biopsy specimens were fixed with 4% paraformaldehyde for 1 hour and then place in 30% sucrose overnight for cryoprotection. The specimens were embedded with in O.C.T. compound or glycolmethacrylate (GMA) resin (Park Scientifice, Northampton, UK) and cut as 3 μm-thick sections. All sections were stained with Alcian blue/PAS (to visualize goblet cells) and counterstained with hematoxylin (to count the total number of cells). The Alcian blue (1%) was diluted with acetic acid (3%), with a final pH of 2.5.

In Situ Hybridization of EGFR and MUC5AC

In situ hybridization was performed, using a human EGFR probe, which contains a 350-bp cDNA fragment of the human EGFR gene (pTRI-EGF-R-human probe template, Ambion, Austin, Tex.) and a human MUC5AC probe, which contains a 298-bp cDNA fragment of the human MUC5AC gene. A pBludscript II SK⁻ vector (Stratagene, LaJolla, Calif.) was used for the subcloning of the EGFR fragment. Hybridization was performed as described. Lou et al. (1998) *Am. J. Respir. Crit. Care Med.* 157:1927-1934. In brief, frozen sections (4 μm) were cut and placed on positively charged glass slides (Superfrost Plus, Fisher Sci, Pittsburgh, Pa.). Sections cut in close proximity were used for hybridization with sense and antisense probes. The specimens were refixed in 4% paraformaldehyde, rehydrated in 0.5×SSC, and then acetylated in triethanolamine and acetic anhydride. Hybridization was carried out with 2500-3000 cpm/μl of antisense or sense probe in 50% deionized formamide, 0.3 M NaCl, 20 mM Tris, 5 mM EDTA, 1×Denhardt's solution, 20 mM dithiothreitol, 10% dextran sulfate, 0.5 mg/ml yeast tRNA, and 0.5 mg/ml sonicated salmon sperm DNA at 58° C. overnight. Posthybridization treatment consisted of washes with 2×SSC, 1 mM EDTA, 10 mM β-mercaptoethanol at room temperature, incubation with RNase solution (20 μg/ml) for 30 minutes at room temperature, and further washes in 0.1×SSC, 1 mM EDTA, 10 mM β-mercaptoethanol at 55° C. for 2 hours and then in 0.5×SSC at room temperature for 20 minutes. Specimens were dehydrated, air-dried, and covered with Kodak NBT nuclear track emulsion (Eastman Kodak, Rochester, N.Y.) for autoradiography. After exposure for 7 to 21 days at 4° C., the slides were developed, fixed, and counterstained with hematoxylin.

Immunohistochemical Analysis of EGFR and MUC5AC

Immunohistochemistry was performed using GMA-embedded sections. Sections were re-fixed with 4% paraformaldehyde for 5 minutes. PBS containing 0.05% Tween 20, 2% normal goat serum and Levamisol (2 mM) was used as diluent for the antibodies. The sections were incubated with mouse monoclonal antibody to EGFR (1:40, Calbiochem, San Diego, Calif.) or mouse monoclonal antibody to MUC5AC (clone 45 M1, 1:100, NeoMarkers, Fremont, Calif.) overnight at room temperature, and then washed 3 times with PBS to remove excess primary antibody. The sections were then incubated with biotinylated horse anti-mouse IgG (Vector Laboratories) at 1:200 dilution for 2 hours at room temperature. Bound antibody was visualized according to standard protocols for the avidin-biotin-alkaline phosphatase complex method. All immunohistochemical staining included control sections unexposed to primary antibody, with substitution of an unrelated antibody of the same isotype or preincubation of the antibody with a 10-fold excess of immunizing peptide. For immunostaining of EGFR, a rabbit polyclonal antibody to EGFR (1:100, Calbiochem) was also used to confirm the staining pattern and to perform quenching using EGFR peptide antigen, which corresponds to amino acid residues 1005-1016 of the human EGFR (Calbiochem). For anti-EGFR antibody, control experiments were carried out by preincubating the antibody with cell lysates prepared from the EGFR-over-expressing A431 cell line.

Morphometric Analysis

Six images of the airway epithelium were captured randomly from the biopsy sections that stained with anti-EGFR Ab or with anti-MUC5AC Ab at ×400 magnification. Goblet cell area was assessed by the volume density of MUC5AC immunoreactivity on the epithelial mucosal surface, using a semiautomatic imaging system described elsewhere. Takeyama et al. (1998) *Am. J. Physiol.* 275:L294-L302. We measured the positively-stained area and the total epithelial area and expressed the data as the percentage of the positively-stained area. The analysis was performed with the public domain NIH IMAGE program (developed at the U.S. National Institutes of Health and available by anonymous FTP from zippy.nimh.gov or on floppy disk from the National Technical Information Service, Springfield, Va., part number PB95-500195GEI). EGFR immunoreactivity was analyzed by Stereology Toolbox (version 1.1, Morphometrix, Davis, Calif.). The number of EGFR-positive cells in the airway epithelium was determined by point counting, using a cycloid consisting of points and line. The point counting was performed by an investigator blind to the identity and disease category of the subjects.

Statistical Analysis

Statistics were performed using StatView 4.01 (Abacus concepts, Berkeley, Calif.). All data are expressed as mean ±SEM. The Mann-Whitney U test was used to determine statistically significant differences between groups; the Pearson's linear regression analysis and one-way analysis of variance were used to determine a correlation between variables. A probability of less than 0.05 for the null hypothesis was accepted as indicating a statistically significant difference.

Results

EGFR mRNA

In all asthmatic subjects, in situ hybridization showed expression of EGFR mRNA in airway epithelium, whereas healthy subjects showed little EGFR mRNA expression. The EGFR sense probe was uniformly negative.

EGFR Protein

Figure 6:
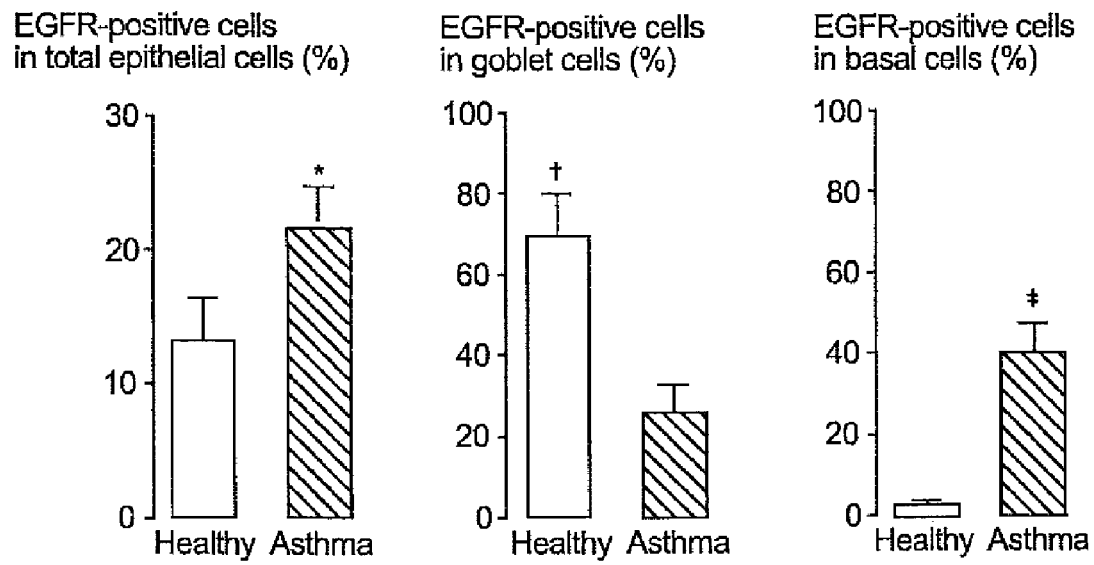
FIG. 6 is a bar graph depicting tissue distribution of EGFR immunoreactivity in healthy and in asthmatic airway epithelial cells.

The percent of total epithelial cells that were EGFR-positive was greater in asthmatics than in healthy subjects ($P<0.05$, FIG. 6, left columns). In healthy subjects, EGFR immunoreactivity was rare and was almost entirely limited to goblet cells. In asthmatic subjects, EGFR immunoreactivity varied: In some subjects, EGFR immunoreactivity was observed only in goblet cells, and was also observed in the airway lumen. In others, EGFR immunoreactivity was localized mainly in basal cells. Percent EGFR immunoreactivity in basal cells was greater in asthmatics than in healthy subjects; in goblet cells, percent EGFR immunoreactivity was greater in healthy subjects than in asthmatics (FIG. 6). Occasionally, mucus glands were observed in the biopsies. Mucus, but not serous, cells in glands showed EGFR immunoreactivity. Ciliated cells showed no EGFR immunoreactivity either in asthmatic or in healthy subjects. Sections unexposed to primary antibody or with substitution of an unrelated antibody of the same isotype were negative, and EGFR immunoreactivity was diminished by preadsorption of the antibody with excess EGFR protein.

The results of EGFR immunoreactivity in goblet and basal cells are summarized in Table 4.

TABLE 4

| Case | | Goblet cells | Basal cells |
|---|---|---|---|
| Healthy | 1 | − | − |
|  | 2 | ++ | − |
|  | 3 | +++ | ± |
|  | 4 | − | − |
|  | 5 | +++ | − |
|  | 6 | +++ | − |
|  | 7 | +++ | − |
|  | 8 | +++ | + |
|  | 9 | +++ | − |
|  | 10 | +++ | − |
|  | 11 | +++ | − |
| Asthmatics | 1 | − | +++ |
|  | 2 | − | + |
|  | 3 | + | +++ |
|  | 4 | ± | + |
|  | 5 | + | ++ |
|  | 6 | +++ | ± |
|  | 7 | + | ++ |
|  | 8 | ++ | + |
|  | 9 | ++ | ++ |
|  | 10 | ++ | ± |
|  | 11 | − | +++ |
|  | 12 | + | ++ |

MUC5AC mRNA. In asthmatic subjects, MUC5AC mRNA was expressed in airway epithelium in a patchy pattern similar to the distribution of goblet cells. Epithelium from healthy subjects showed only weak expression of MUC5AC mRNA, which was located in the distribution of goblet cells. The MUC5AC sense probe was uniformly negative.

Co-localization of MUC5AC and EGFR. The immunoreactivity of MUC5AC and EGFR were co-localized in goblet cells that were stained with Alcian blue/PAS, when the EGFR immunoreactivity was observed in goblet cells.

Figure 7:
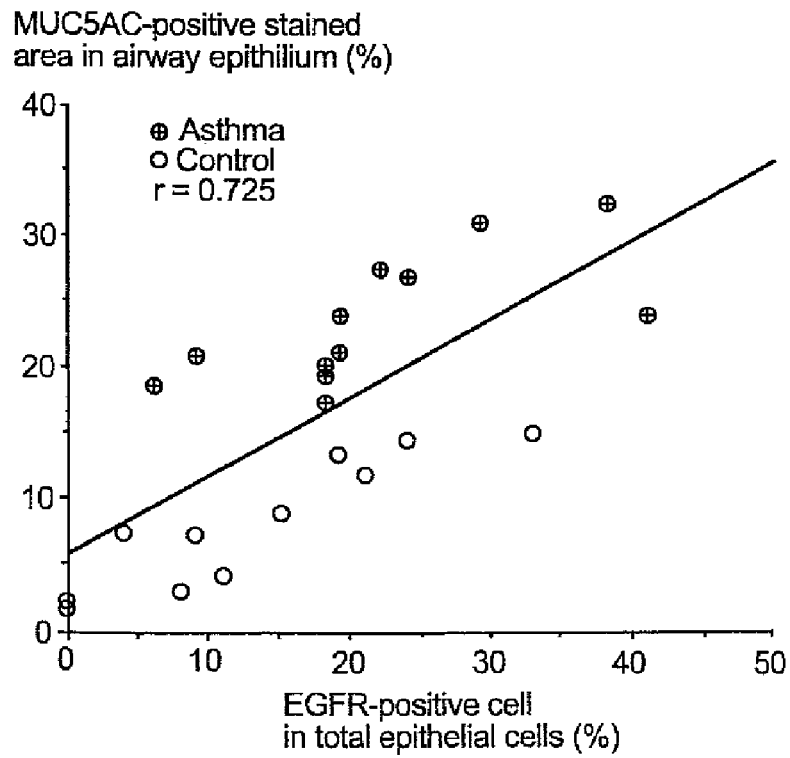
FIG. 7 is a graph depicting correlation between EGFR immunoreactivity and MUC5AC production in airway epithelium.

Correlation of EGFR immunoreactivity with MUC5AC. The EGFR immunoreactivity of airway epithelial cells showed a significant positive correlation with the area of MUC5AC-positive staining in airway epithelium among all subjects ($n=23$, $r=0.725$, $P<0.0001$) (FIG. 7).

Example 6

IL-13 Induces Mucus Production by Stimulating EGFRs and Activating Neutrophils

The role of EGFR activation on IL-13-induced mucus production was examined by instilling IL-13 in pathogen-free rats, and the effect of EGFR tyrosine kinase inhibitors on IL-13-induced goblet cell (GC) growth was examined.

Methods

Animals

Specific pathogen-free, male, F344 Fisher rats weighing 220 to 240 g were purchased from Simonsen Laboratories (Gilroy, Calif.). The animals were housed in pathogen-free rooms and maintained on laboratory chow with free access to food and water. The Committee on Animal Research, University of California San Francisco, approved all procedures. Five animals were studied in each group.

Effect of Selective Inhibitor of EGFR Activation on IL-13-Induced GC Metaplasia

Studies were first performed in rats in vivo and showed that IL-13 induces GC metaplasia in rat tracheal epithelium. Animals were anesthetized with pentobarbital [Nembutal sodium, 50 mg/kg, intraperitoneally (ip), Abbott Laboratories, North Chicago, Ill.] and allowed to breathe spontaneously. Vehicle (phosphate buffer solution; PBS) or IL-13 was instilled intratracheally via a 20-gauge Angiocath catheter (Beckton Dickinson, Sandy, Utah) through the mouth, while the laryngeal area was visualized using a high-intensity illuminator (FiberLite; Dolan Jenner Industries, Inc., Lawrence, Mass.). The carinal tissues were examined 48 hours after instillation of IL-13. Various concentrations of IL-13 (recombinant murine IL-13; 5, 50, 100, and 500 ng/rat, R&D systems, Minneapolis, Minn.) were instilled into the trachea in 200 µl PBS. Sterile PBS (200 µl) was instilled into the trachea as controls.

For examination of the relationship between IL-13-induced GC metaplasia and activation of EGFR, animals were pretreated 1 d before instillation of IL-13 and daily thereafter with a selective EGFR tyrosine kinase inhibitor (BIBX 1522; 1-30 mg/kg/day, ip; Boehringer Ingelheim, Ingelheim, Germany). Animals were euthanized 48 hours after instillation of IL-13.

Role of leukocyte recruitment in IL-13-induced goblet cell metaplasia

In preliminary studies, we noted that IL-13 causes leukocyte recruitment into the airways. We hypothesized that leukocyte recruitment results from IL-13-induced chemoattractant release from epithelium, and that this recruitment is involved in the IL-13-induced EGFR cascade leading to GC metaplasia. Groups of animals were euthanized 4, 8, 16, 24, and 48 hours after instillation of IL-13 (500 ng), and leukocytes were counted in airway tissue.

For evaluation of the role of leukocytes in IL-13-induced GC metaplasia, rats were pretreated with an inhibitor of leukocytes in the bone marrow [cyclophosphamide (17); Sigma chemical Co., St Louis, Mo.] or with a blocking antibody to interleukin-8 (IL-8Ab; rabbit anti-human IL-8 antibody; Biosource, Camarillo, Calif.). Cyclophosphamide (100 mg/kg, ip) was given 5 days before instillation of a single dose with IL-13 of (500 ng), and a second injection of cyclophosphamide (50 mg/kg, ip) was given 1 d before instillation of IL-13. In another series of studies, we instilled IL-8 Ab (10 μg/rat) intratracheally, along with IL-13; we repeated the instillation of anti-human IL-8 blocking antibody at 12 hour intervals until the animals were euthanized.

Tissue Preparation.

Animals were euthanized with a lethal dose of pentobarbital (Nembutal sodium, 200 mg/kg, ip, Abbott Laboratories, North Chicago, Ill.), and the systemic circulation was perfused with 1% paraformaldehyde in Diethylpyrocarbonate (DEPC, Sigma chemical Co., St Louis, Mo.)-treated PBS via the left ventricle. For frozen sections, carinal tissues were removed, placed in 4% paraformaldehyde overnight, and then placed in 30% sucrose for cryoprotection. The tissues were embedded in optimal cutting temperature (OCT, Sakura Finetek U.S.A., Inc., Torrance, Calif.) compound. For plastic or paraffin sections, tissues were placed in 4% paraformaldehyde overnight, dehydrated with ethanol, and embedded in JB-4 plus monomer solution A (Polysciences, Inc., Warrington, Pa.) or in paraffin. The embedded tissues were cut as cross sections 4 μm thick and placed on glass slides.

Quantification of GC Metaplasia

In all studies, the carina was examined to obtain consistent sampling. We measured AB/PAS-positive areas and total epithelial area, and we expressed the results as the percentage of AB/PAS area to total epithelial area. The analysis was performed with the public domain NIH IMAGE program (developed at the U.S. National Institutes of Health and available by anonymous FTP from zippy.nimh.gov. or floppy disk from the National Technical Information Service, Springfield, Va., part number PB95-500195GEI).

Immunohistochemical Staining for MUC5AC, EGFR Protein, TNF☐ and IL-8 in Rat Carinal Epithelium Phosphate buffer solution containing 0.05% Tween 20 and 2% normal goat serum was used as diluent for the antibodies after blocking endogenous peroxidase with 0.3% $H_2O_2$ in methanol. Sections were incubated with mouse mAb to EGFR (1:250, Calbiochem, San Diego, Calif.), to MUC5AC (clone 45 M1, 1:500, New Markers, Fremont, Calif.), or a rabbit antibody to TNFα (1:1000, Genzyme, Cambridge, Mass.) overnight at 4° C. and washed with PBS to remove excess primary antibody. For immunohistochemical localization of IL-8-like substance, we used mouse anti-human IL-8 antibody (1:20; Biosource, Camarillo, Calif.). The sections were then incubated with biotinylated horse anti-mouse IgG (Vector Laboratories, Burlingame, Calif.) at 1:200 dilution for 1 hour at room temperature. Bound antibody was visualized according to standard protocols for avidin-biotin-peroxidase complex method. The measurement of MUC5AC protein also utilized the same method used for quantitative measurement of GC metaplasia in the epithelium.

Evaluation of Leukocytes in Airway Tissue

Animals were euthanized 4, 8, 16, 24, and 48 hours after instillation of IL-13 (500 ng), and leukocytes were counted in airway tissue. To evaluate the recruitment of neutrophils, we stained the sections with 3,3'-diaminobenzidine for neutrophils and then counterstained them with toluidine blue. Neutrophils seen as peroxidase-positive blue cytoplasmic cells were counted in six consecutive high-power fields of the epithelium (from the basement membrane to cell apices) in the carina. To evaluate the recruitment of eosinophils, we stained the sections with Luna's reagent.

Isolation and Chemotaxis of Human Neutrophils

Human neutrophils were purified from peripheral blood obtained from healthy donors. Neutrophil isolation was performed by standard techniques of Ficoll-Hypaque gradient separation, dextran sedimentation, and hypotonic lysis of erythrocytes. Cells were routinely >95% viable by trypan blue dye exclusion. To prevent endotoxin contamination, all solutions were passed through a 0.1 μm filter. Chemotactic activity was assessed in 48-well microchemotaxis chamber (Neuroprobe, Cabin John, Md.), utilizing the leading front technique. Migration was measured as net movement of neutrophils (μm) through a nitrocellulose filter (pore size, 3 μm) after 25 min at 37° C. The effect of IL-13 ($10^{-10}$, $10^{-9}$, and $5 \times 10^{-9}$ M; recombinant human IL-13; R&D systems, Minneapolis, Minn.) is expressed as the distance traveled, compared to the random migration of neutrophils incubated with RPMI 1640.

Data Analysis

All data are expressed as mean ±SEM. Statistical analysis performed with one-way ANOVA was used to determine statistically significant differences between groups. Scheffe's F test was used to correct for multiple comparisons when statistical significances were identified in ANOVA. A probability of less than 0.05 was accepted as indicating a statistically significant difference.

Results

Effect of Interleukin-13 on Goblet Cell Metaplasia

To confirm that IL-13 induces mucin production, IL-13 (5, 50, 100, and 500 ng/rat) was instilled into the trachea, and tissues were examined 48 hours later. In control rats, the airway epithelium contained only sparse AB/PAS and MUC5AC staining (FIG. 8). IL-13 increased AB/PAS and MUC5AC staining dose-dependently (FIG. 8). These results implicate IL-13 induces GC metaplasia and MUC5AC mucin production in rat airway epithelium.

Figure 9:
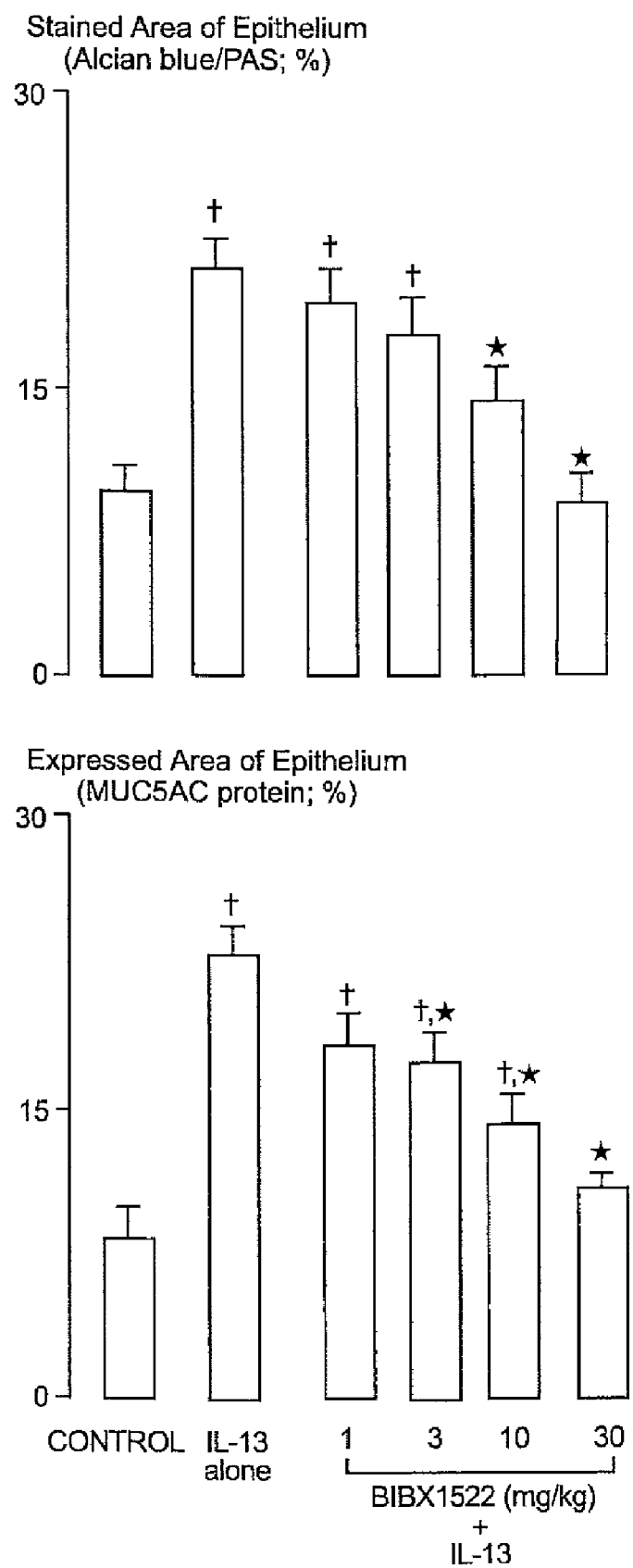
FIG. 9 is a graph depicting dose-dependent inhibition of Il-13-induced staining of mucous glycoconjugates with Alcian blue/PAS (FIG. 9A) and MUC5AC (FIG. 9B) by a selective EGFR tyrosine kinase inhibitor, BIBX 1522, in rats.

Effect of a Selective Inhibitor of EGFR Activation on IL-13-Induced Goblet-Cell Metaplasia To examine the relationship between IL-13-induced GC metaplasia and activation of EGFR, animals were pretreated with a selective EGFR tyrosine kinase inhibitor (BIBX 1522, 1-30 mg/kg/day). Control rats showed little EGFR expression in airway epithelium, but instillation of IL-13 increased EGFR expression. Pretreatment with a selective EGFR tyrosine kinase inhibitor, BIBX 1522, prevented IL-13-induced AB/PAS and MUC5AC staining dose-dependently and completely (FIG. 9). These findings implicate EGFR activation in IL-13-induced mucin production.

Expression of TNFα in Rat Airway Tissue.

We examined the effect of instillation of IL-13 on TNFα expression: In control rats, staining with TNFα antibody was minimal. Instillation of IL-13 induced TNFα expression, mainly in infiltrating neutrophils. Pretreatment with cyclophosphamide prevented IL-13-induced TNFα expression.

The Effect of IL-13 on Leukocyte Recruitment and Mucin Production

The airway epithelium of control rats contained few leukocytes, but instillation of IL-13 into the airway caused time-dependent leukocyte recruitment (FIG. 10A), which started after approximately 8 hours and which was maximal within 24 hours. Pretreatment with cyclophosphamide, a drug that suppresses leukocytes in the bone marrow, inhibited leukocyte recruitment into airways (FIG. 10A) and prevented IL-13-induced mucin production (FIG. 10B).

To examine the effect of IL-13 on neutrophil chemotaxis in vitro, we studied with human neutrophils. IL-13 decreased neutrophil movement dose-dependently; at a concentration of $5 \times 10^{-9}$ M, IL-13 caused a decrease to 50.6±3.4% of control values.

Because IL-13 did not cause neutrophil chemotaxis, we hypothesized that IL-13 stimulates the production of a neutrophil chemoattractant in the epithelium. In control animals, the airway epithelium did not stain for IL-8-like chemoattractant, but instillation of IL-13 resulted in positive staining with an anti-human IL-8 antibody. Pretreatment with an IL-8 blocking antibody inhibited IL-13-induced leukocyte recruitment and mucin production (FIG. 10). These findings indicate that IL-13 induces an airway epithelial IL-8-like chemoattractant, which causes neutrophil recruitment.

Example 7

Activation of EGFR Promotes Mucin Synthesis Induced by Cigarette Smoke

As described in Example 2, pro-inflammatory cytokine-activated neutrophils and cigarette smoke cause mucin MUC5AC synthesis in human bronchial epithelial cells in vitro via ligand-dependent activation of EGFR. This phenomenon was further examined by in vivo studies carried out on rats and humans.

Methods
In Vitro Studies
Preparation of Cigarette Smoke Solution
Cigarette smoke solution was prepared as described in Example 2.
Cell Culture
NCI-H292 cells, a human pulmonary mucoepidermoid carcinoma cell line, were grown in RPMI 1640 medium containing 10% fetal bovine serum, penicillin (100 U/ml), streptomycin (100 µg/ml) and Hepes (25 mM) at 37° C. in a humidified 5% $CO_2$ water-jacketed incubator. Either 6-well culture plates or 8-chamber slides were used to culture the cells. When confluent, cells were incubated for 1 hour with cigarette smoke solution. The cells were then washed and incubated with fresh medium alone. Experiments were terminated at preselected times (for mRNA, 6 hours and 12 hours; for protein, 24 hours). As controls, cells were incubated with medium alone for same time periods. In inhibition studies with EGFR tyrosine kinase inhibitors, NCI-H292 cells were pretreated with BIBX1522 (10 µg/ml, generously provided by Boehringer Ingelheim Pharma KG, Ingelheim, Germany) or tyrphostin AG1478 (10 µM, Calbiochem) 30 min before delivering the cigarette smoke solution. The effects of a selective inhibitor of platelet-derived growth factor receptor tyrosine kinase (tyrphostin AG1295, 100 µM, Calbiochem), and a negative control for tyrphostins (tyrphostin A1, 100 µM, Calbiochem) were also examined. The role of reactive oxygen species was examined using a scavenger of oxygen free radicals DMSO (1%, Sigma), or superoxide dismutase (SOD, 300 U/ml, Sigma).

Immunoblotting for Activated EGFR.
Cells were serum-starved for 24 hours and then stimulated with cigarette smoke solution or with TGFα for 15 minutes. After stimulation, cells were lysed with lysis buffer (20 mM sodium phosphate, pH 7.8, 150 mM NaCl, 5 mM EDTA, 50 mM HEPES, 1% Triton-X100, 50 mM NaF, 1 mM sodium orthovanadate, 5 mM PMSF, and 10 µg/ml each of leupeptin and aprotinin) and incubated for 30 minutes at 4° C. To remove insoluble materials, cell lysates were centrifuged at 14,000 rpm for 5 minutes at 4° C. Aliquots of supernatants containing equal amounts of protein were suspended in SDS sample buffer and boiled for 5 minutes. Proteins were separated by SDS-PAGE in 4-15% acrylamide gel. The resulting gel was equilibrated in the transfer buffer: 25 mM Tris-HCl, 192 mM glycine, 20% (vol/vol) methanol, pH 8.3. The proteins were then transferred electrophoretically to nitrocellulose membranes, which were incubated with 5% fat-free skimmed milk in PBS containing 0.05% Tween 20 for 1 hour and then incubated with anti-phospho-specific EGFR mAb (2 µg/ml, Calbiochem) overnight. Bound Ab was visualized according to a standard protocol for the avidin-biotin-alkaline phosphatase complex method (ABC kit, Vector Laboratories, Burlingame, Calif.).

In Situ Hybridization of EGFR mRNA and MUC5AC mRNA.

In situ hybridization was performed using a human EGFR probe, which contains a 350-bp cDNA fragment of the human EGFR gene (pTRI-EGFR-human probe template, Ambion, Austin, Tex.) and a human MUC5AC probe, which contains a 298-bp cDNA fragment of the human MUC5AC gene. The 350-bp cDNA human EGFR was subcloned into pBluescript II SK$^-$ vector at Kpn I and EcoR I sites. This pBluescript was used to generate human EGFR antisense and sense probes. Hybridization was performed as described previously. Lou et al. (1998) *Am. J. Respir. Crit. Care Med.* 157:1927-1934. In brief, the cells grown on the 8-chamber slides were fixed in 4% paraformaldehyde, rehydrated in 0.5×SSC, and then acetylated in triethanolamine and acetic anhydride. Hybridization was carried out with 2500-4000 cpm/µl of antisense or sense probe in 50% deionized formamide, 0.3 M NaCl, 20 mM Tris, 5 mM EDTA, 1×Denhardt's solution, 20 mM dithiothreitol, 10% dextran sulfate, 0.5 mg/ml yeast tRNA, and 0.5 mg/ml sonicated salmon sperm DNA at 58° C. overnight. Posthybridization treatment consisted of washes with 2×SSC, 1 mM EDTA, 10 mM β-mercaptoethanol at room temperature, incubation with RNase solution (20 µg/ml) for 30 min at room temperature, and further washes in 0.1×SSC, 1 mM EDTA, 10 mM β-mercaptoethanol at 55° C. for 2 hours and then in 0.5×SSC at room temperature for 20 minutes. Specimens were dehydrated, air-dried, and covered with Kodak NBT nuclear track emulsion (Eastman Kodak, Rochester, N.Y.) for autoradiography. After exposure for 7 to 21 days at 4° C., the slides were developed, fixed, and counterstained with hematoxylin.

Immunoassay of MUC5AC Protein.

MUC5AC protein was measured as described previously. Takeyama et al. (1999) *Proc. Natl. Acad. Sci. USA* 96:3081-3086. In brief, cell lysates were prepared with PBS at multiple dilutions, and 50 µl of each sample was incubated with bicarbonate-carbonate buffer (50 µl) at 40° C. in a 96-well plate (Maxisorp Nunc, Fisher Scientific, Santa Clara, Calif.), until dry. Plates were washed three times with PBS and blocked with 2% bovine serum albumin, fraction V (Sigma) for 1 hour at room temperature. Plates were again washed three times with PBS and then incubated with 50 µl of MUC5AC mAb (1:100) that was diluted with PBS containing 0.05% Tween 20. After 1 hour, the wells were washed three times with PBS, and 100 µl horseradish peroxidase-goat anti-mouse IgG conjugate (1:10,000) was dispensed into each well. After 1 hour, plates were washed three times with PBS. Color reaction was developed with 3,3',5,5'-tetramethylbenzidine (TMB) peroxidase solution (Kirkegaard & Perry Laboratories, Gaithersburg, Md.) and stopped with $2NH_2SO_4$. Absorbance was read at 450 nm.

In Vivo Studies.

Drugs

BIBX1522 (3 or 9 mg) was dissolved in 0.6 ml chloroform containing 25% (w/v) solutol. This solution was evaporated to dryness. The residue was redissolved in 0.3 ml methanol and once again evaporated to dryness. This stock preparation was stored at 4° C. for 5 days. The solution for intratracheal instillation was made up freshly each day by dissolving the stock preparation in 3 ml of prewarmed saline (40° C.) to achieve a final concentration of 0.1 and 0.3%, respectively.

Induction of Goblet Cell Metaplasia by Cigarette Smoke Exposure

Male Sprague Dawley rats weighing 250-300 g were used for the study. The animals were housed in a temperature- and humidity-controlled room and had free access to water and standard laboratory food. Animals were assigned at random to the non-smoking control group or to the smoke-exposed control and treatment groups. Rats in the smoking groups were exposed to 8 regular, non-filter cigarettes (1.2 mg. nicotine, 12 mg. condensate) a day for 5 days, using a smoking apparatus with chambers adapted for rats. Inhibition of Cigarette Smoke-Induced Goblet Cell Metaplasia by the EGFR Kinase Inhibitor BIBX 1522

To evaluate the effect of EGFR kinase inhibitor on goblet cell metaplasia and mucus production, the animals were treated once daily with vehicle or with BIBX 1522 at doses of 1 or 3 mg/kg intratracheally 1 hour before the exposure to cigarette smoke. Treatment of the animals with vehicle or BIBX 1522 started on day 1 and was continued for 5 days during exposure to cigarette smoke. The intratracheal instillation in a volume of 1 ml/kg was performed under isoflurane anesthesia.

RNA Isolation and Quantification

Eight hours after the last exposure to cigarette smoke, the animals were euthanized with sodium pentobarbital. Trachea and right mainstem bronchus were removed and processed for total RNA isolation, using a Qiagen RNeasy kit, according to the manufacturer's instructions. For RNA quantification, the real-time PCR technology (TaqMan-PCR, ABI Prism 7700 Sequence Detection System, Perkin Elmer Applied Biosystems, Foster City, Calif.) was employed. This technology has been described in detail elsewhere. Fink et al. (1998) *Nature Med.* 4:1329-1333. Briefly, during PCR cycles, the 5' fluorescent labeled nucleotide is released from the probe by exonuclease activity of the TaqPolymerase; the emission of fluorescence is detected via laser, and during proceeding PCR cycles an increasing fluorescence above background is measured and documented. The signal is normalized in relation to an internal reference signal, and the software sets the threshold cycle (Ct) when the difference to the reference signal is more than 10-fold of standard deviation. The Ct-value is used for quantification of the input target number.

Primers and probes for rat MUC5AC were designed using the PrimerExpres™1.0 program provided by Perkin Elmer. The following sequences were used for the quantification of the rat MUC5AC: forward primer 5'-TGG GAA CCA TCA TCT ACA ACC A-3', reverse primer 5'-TCC TGA CTA ACC CCT TTG ACC A-3' and the FAM reporter dye-labeled hybridization probe:5'-CCT TGA CGG CCA CTG TTA CTA TGC GAT GT-3'.

Primers and probe for ribosomal RNA were purchased from Biosystems Deutschland GmbH [TaqMan$^R$ Ribosomal RNA Control Reagents (VIC™ Probe), U.S. Pat. No. 4,308,329]. RT-PCR and TaqMan PCR were performed in a one-step RT-PCR using the TaqMan$^R$ EZ RT-PCR Core Reagents (Part No. $N_8O_8$-0236); forward primer 50 nM, reverse primer 300 nM, probe 100 nM, manganese acetate 2.5 mM; total RNA approximately 5-10 ng; enzymes, reaction buffer and nucleotides according to the manufacturer's protocol (TaqMan$^R$ EZ RT-PCR Kit, The Perkin-Elmer Corporation, P/N 402877 Rev. A, 1996). Cycles: 10' 50° C.; 30' 60° C.; 5' 95° C.; 40×20" 94° C., 1' 59° C. To quantify the mRNA expression, the target gene was first normalized to the ribosomal RNA as internal standard. The data were then expressed as the relative amount of MUC5AC compared to a standard control tissue.

Tissue Preparation and Quantification of Goblet Cell Production

The lungs were dissected and fixed in 7% buffered formalin and embedded in paraffin. The left main stem bronchus was used for immunohistochemical staining. Lung sections were cut to include the full length of the main intrapulmonary airway and stained sequentially with hematoxylin and eosin, or with Alcian blue/PAS to evaluate the total epithelial area and the area stained for intracellular mucous glycoconjugates, respectively. Goblet cell production was determined by the volume density of Alcian blue/PAS-stained mucous glycoconjugates on the epithelial mucosal surface using an image analysis system (SIS, Muenster, Germany). The Alcian blue/PAS-positive stained area and the total epithelial area were measured over a length of 2 mm of the basal lamina. The data are expressed as the percentage of the total area stained by Alcian blue/PAS.

Human Studies

Subjects

The protocol for human studies was approved by the Committee for Human Research at the University of California San Francisco. Samples of human bronchial epithelium in four subjects, who met clinical diagnostic criteria for COPD (American Thoracic Society (1987) *Am. Rev. Respir. Dis.* 136:225-243) were obtained at the time of surgery. There was no history of endotracheal intubation within the past 5 years, and no history of significant cardiac or neurologic disease.

Tissue Preparation

Surgical specimens were fixed with 4% paraformaldehyde for 1 hour and then placed in 30% sucrose for cryoprotection overnight. The specimens were embedded in O.C.T. compound and cut as 4 µm-thick sections.

Immunohistochemical Analysis of EGFR.

Immunohistochemistry was performed using frozen sections. Sections were re-fixed with 4% paraformaldehyde for 5 min. PBS containing 0.05% Tween 20, 2% normal goat serum and Levamisol (2 mM) was used as diluent for the antibodies. The sections were incubated with mouse monoclonal antibody to EGFR (1:200, Calbiochem, San Diego, Calif.) for 2 hours at room temperature, and then washed 3 times with PBS to remove excess primary antibody. The sections were then incubated with biotinylated horse anti-mouse IgG (Vector Laboratories) at 1:200 dilution for 1 hour at room temperature. Bound antibody was visualized according to standard protocols for the avidin-biotin-alkaline phosphatase complex method. All immunohistochemical staining included control sections unexposed to primary antibody, with substitution of an unrelated antibody of the same isotype or preincubation of the antibody with a 10-fold excess of immunizing peptide. A rabbit polyclonal antibody to EGFR (1:100, Calbiochem) was also used to confirm the staining pattern and to perform quenching using EGFR peptide antigen, which corresponds to amino acid residues 1005-1016 of the human EGFR (Calbiochem).

Statistics

All data are expressed as means ±SEM. One-way analysis of variance was used to determine statistically significant differences between groups. Scheffe's F test was used to correct for multiple comparisons when statistical significances were identified in the analysis of variance. A probability of less than 0.05 for the null hypothesis was accepted as indicating a statistically significant difference.

Results

A. In Vitro Studies in NCI-H292 Cells.

Cigarette Smoke Up-Regulates EGFR mRNA Expression.

In the control condition, NCI-H292 cells expressed EGFR mRNA constitutively. Addition of cigarette smoke solution to the cells up-regulated EGFR mRNA expression within 6 hours, an effect that was increased at 12 hours. TNFa (used as control) also increased EGFR mRNA expression. The sense probe of EGFR showed no expression.

Cigarette Smoke Activates EGFR Tyrosine Phosphorylation.

We examined the effect of cigarette smoke solution on activation of EGFR tyrosine kinase: As a positive control, we used the EGFR ligand, TGFalpha, which increased EGFR-specific tyrosine phosphorylation in NCI-H292 cells (FIG. 11). Similarly, cigarette smoke solution increased EGFR-specific tyrosine phosphorylation, but to a lesser extent (FIG. 11). Pretreatment of NCI-H292 cells with BIBX 1522 inhibited EGFR tyrosine phosphorylation induced by cigarette smoke solution and by TGFα. (FIG. 11).

Cigarette Smoke Increases MUC5AC Expression.

Figure 12:
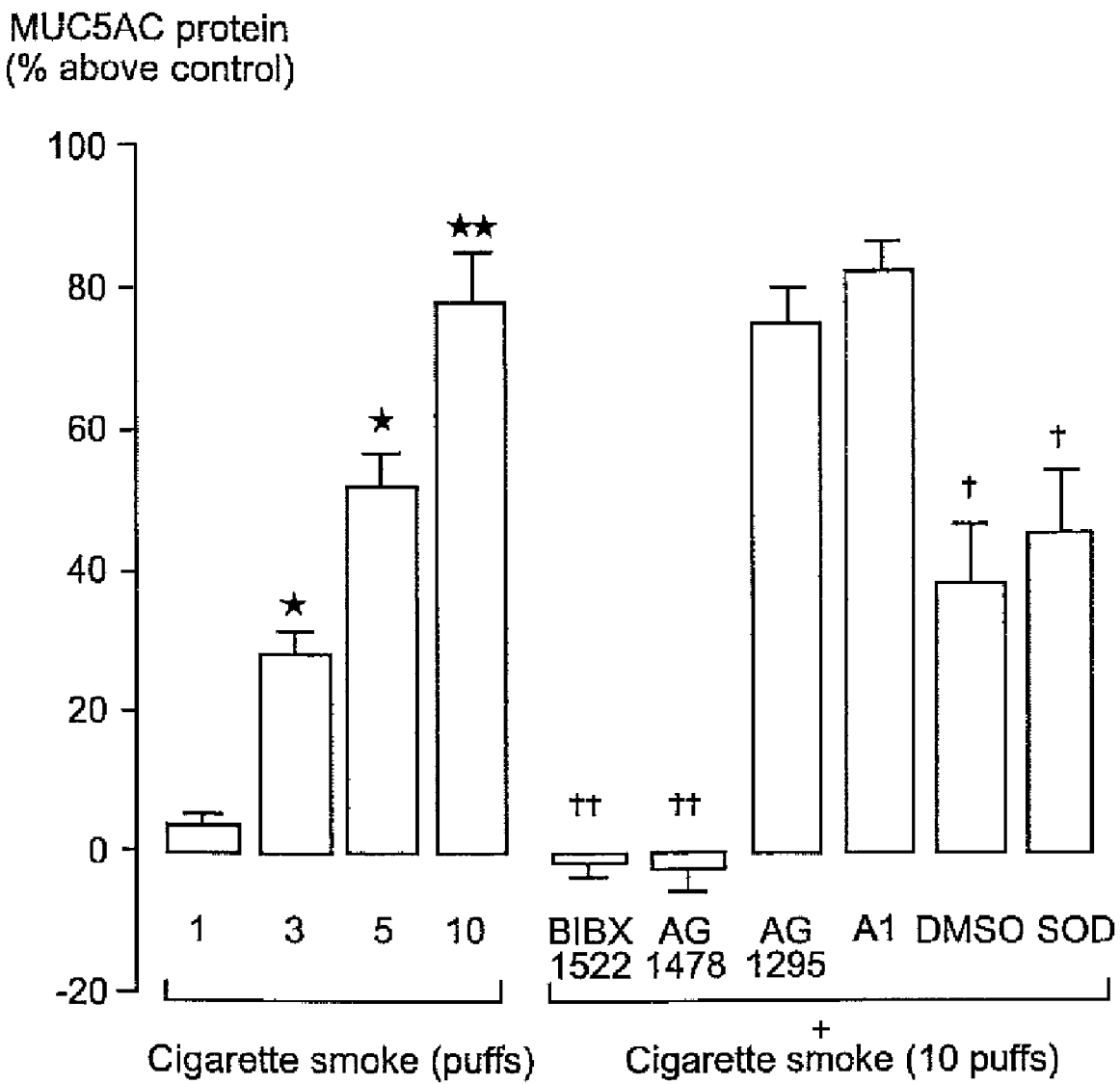
FIG. 12 is a bar graph depicting the effect of incubation of cigarette smoke solution with NCI-H292 cells, and the effects of tyrosin kinase inhibitors and of antioxidants on MUC5AC protein synthesis induced by cigarette smoke.

Resting NCI-H292 cells showed little expression of MUC5AC mRNA at 12 hours. Addition of cigarette smoke solution to the cells upregulated MUC5AC mRNA expression within 6 hours, an effect that was increased at 12 hours. TGFalpha (used as control) also increased MUC5AC mRNA expression. The sense probe of MUC5AC showed no expression. Similarly, cigarette smoke solution increased MUC5AC protein synthesis within 24 hours, an effect that occurred in a dose-dependent fashion (FIG. 12).

EGFR Tyrosine Kinase Inhibitors Prevent MUC5AC Gene and Protein Expression in NCIH292 Cells.

To test whether the cigarette smoke induced-MUC5AC gene and protein expression occurred by activation of EGFR, cells were incubated with various tyrosine kinase inhibitors. Pretreatment of the cells with selective EGFR tyrosine kinase inhibitors (BIBX 1522, AG1478) prevented MUC5AC mRNA expression and MUC5AC protein synthesis induced by cigarette smoke solution (FIG. 12). A selective tyrosine kinase inhibitor of platelet-derived growth factor (AG1295) and a negative control for tyrphostins (AI) were without effect (FIG. 12). Furthermore, cigarette smoke-induced MUC5AC synthesis was inhibited significantly by pretreatment with a free radical scavenger (DMSO), and by SOD. These results indicate that activation of EGF-R tyrosine kinase induces MUC5AC gene and protein expression in NCIH292 cells and that oxidative stress induced by cigarette smoke is involved, at least a part, in cigarette smoke-induced MUC5AC production.

B. In Vivo Studies in Rats

Cigarette Smoke Increases Goblet Cell Production in Pathogen Free Rats.

Figure 13:
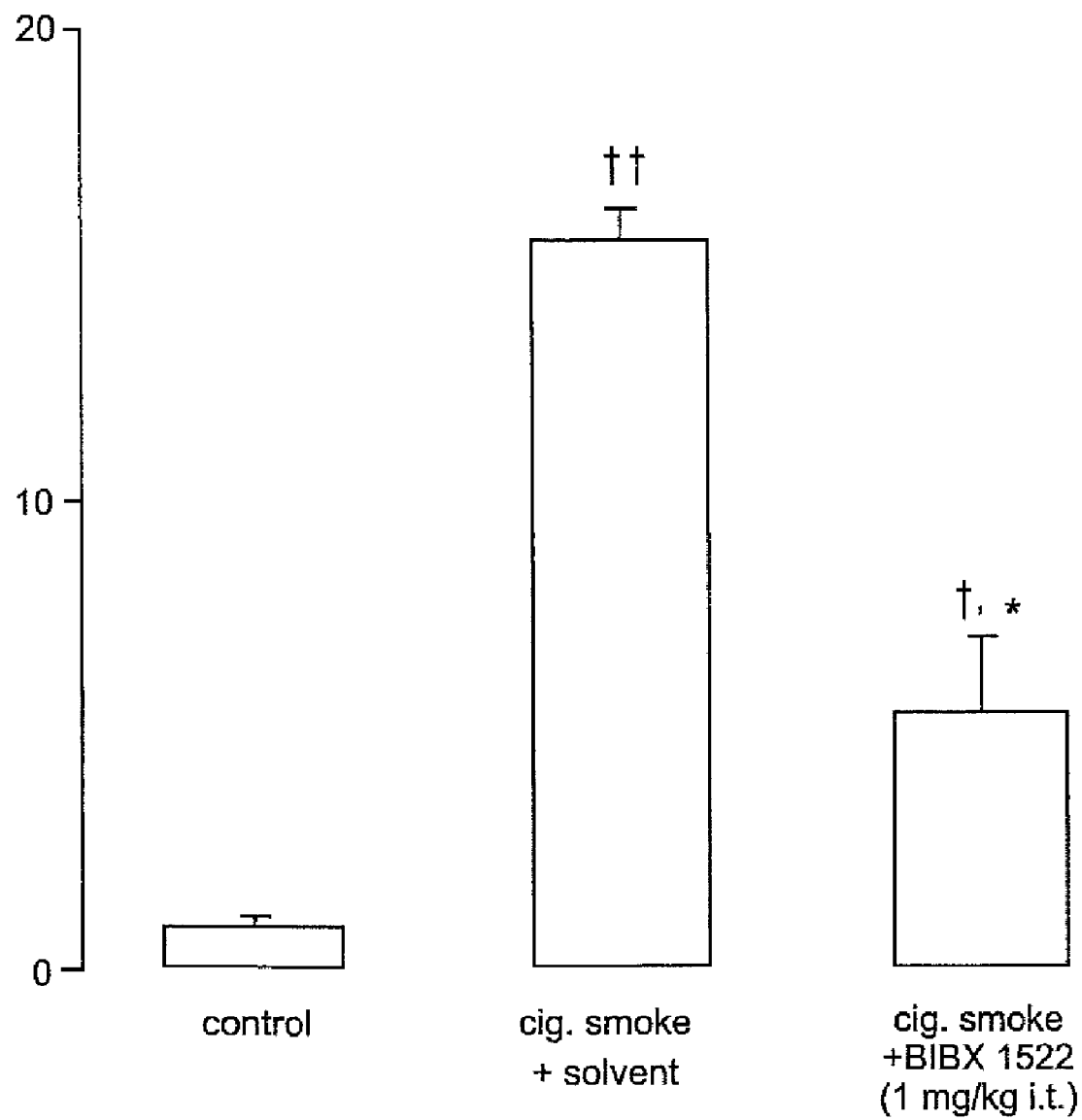
FIG. 13 is a bar graph depicting the effect of inhalation of cigarette smoke on percentage of Alcian blue/PAS-stained area of airway epithelium, and the effect of an EGFR tyrosine kinase inhibitor on cigarette smoke-induced Alcian blue/PAS response in pathogen-free rats.
Figure 14:
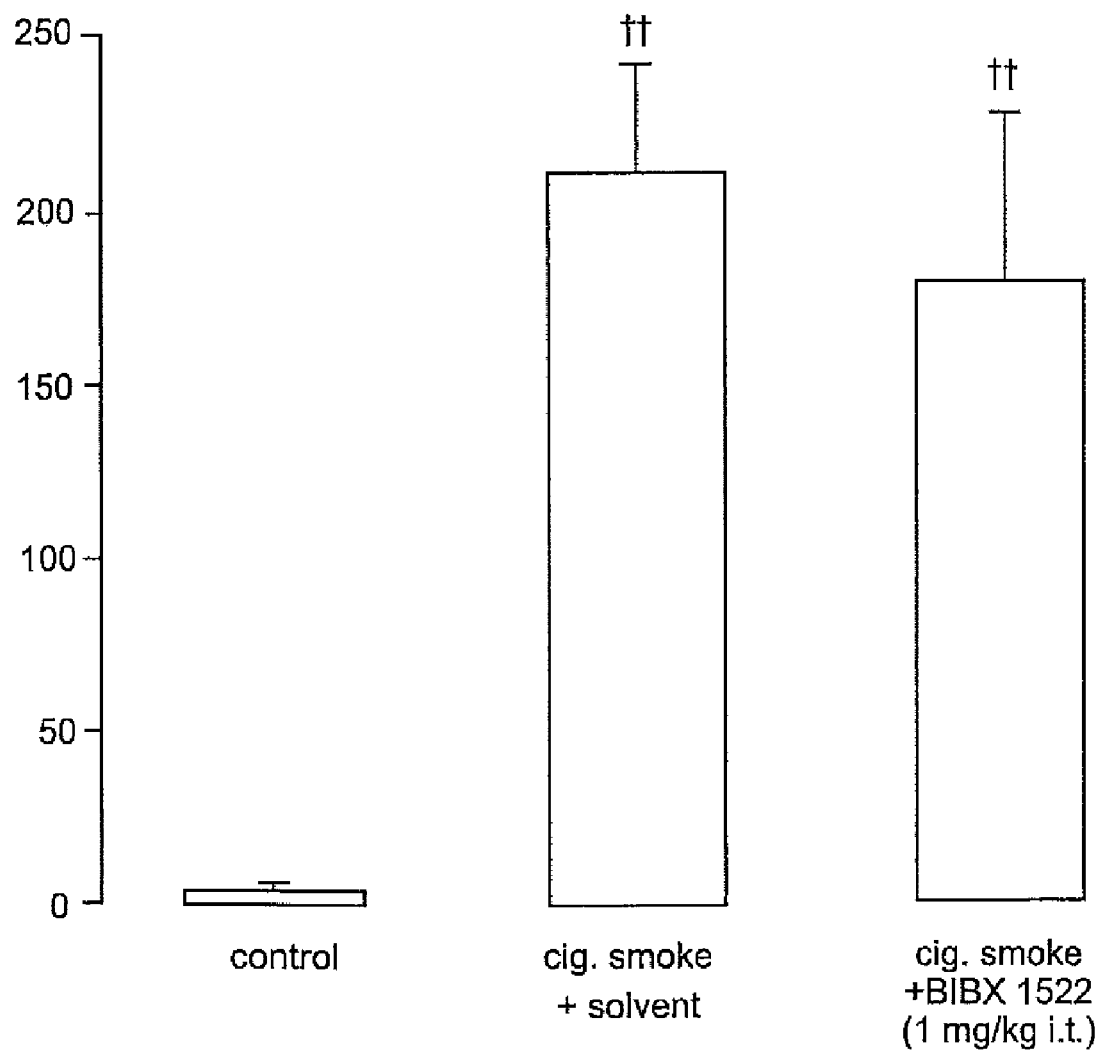
FIG. 14 is a bar graph depicting the effect of inhalation of cigarette smoke on MUC5AC mRNA expression in tracheobronchial tissue in pathogen-free rats, and the effect of an EGFR tyronsim kinase inhibitor on cigarette smoke-induced MUC5AC mRNA expression.

In control animals, the airway epithelium contained few goblet cells (FIG. 13). Inhalation of cigarette smoke (8 cigarettes per day for five days) resulted in markedly increased Alcian blue/PAS staining (FIG. 13). Inhalation of cigarette smoke also increased MUC5AC mucin gene expression (FIG. 14).

EGFR Tyrosine Kinase Inhibitor (BIBX 1552) Prevents Cigarette Smoke-Induced Goblet Cell Production in Pathogen Free Rats.

When rats were treated with BIBX1522 during cigarette smoking, the increase in Alcian blue/PAS staining was inhibited dose-dependently and completely (FIG. 13). BIBX 1522 also prevented the cigarette smoke-induced expression of MUC5AC gene expression (FIG. 14).

C. Human Studies in Patients with COPD.

EGFR immunoreactivity is Located in Airway Goblet Cells and in Submucosal Glands in Patients with COPD.

EGFR immunoreactivity was observed in goblet cells and in mucous glands where Alcian blue/PAS staining was positive, and EGFR staining was also observed in the airway lumen. Sections unexposed to primary antibody or with substitution of an unrelated antibody of the same isotype were negative, and EGFR immunoreactivity was diminished by preadsorption of the antibody with excess EGFR protein.

Example 8

Relationship of EGFR Expression to Goblet Cell Hyperplasia in Nasal Polyps

Nasal polyposis is a common chronic inflammatory disease of the upper airways, affecting the well being and quality of life of afflicted individuals. The possibility that EGFR might be involved in mucus hypersecretion and mucus cell hyperplasia in human nasal polyps was examined. MUC5AC gene and protein expression was examined in nasal polyp epithelium and in normal nasal epithelium of inferior turbinates. Using in situ hybridization and immunochemical staining, EGFR mRNA and protein expression, and their relationship to mucus cell hyperplasia, were analyzed. In addition, the presence and location of TNF-alpha in EGFR expression, as well as the presence of neutrophils, in nasal polyps was examined.

Methods

Materials

Nasal specimens were obtained from patients undergoing surgical procedures. Eight nasal polyps were sampled in patients whose polyps were removed during ethmoidectomy, and six nasal biopsies were obtained from inferior turbinates removed during turbinectomy in snorers (control group). Nasal tissue samples were fixed immediately in formaldehyde and embedded in paraffin for morphological studies. None of the patients with nasal polyposis had cystic fibrosis or primary ciliary dyskinesia. Subjects were requested to stop therapy for polyposis (i.e., glucocorticoids and antibiotics) one month prior to surgery. Informed consent was obtained from all patients, and permission was obtained from the Ethics Committee of Hôpital Henri Mondor (CCPPRB, Creteil, France).

Standard Morphological Evaluation

Five μm paraffin sections were obtained, deparaffinized and stained with Diff-Quik Stain Set (Baxter Healthcare Corporation, Miami, Fla.) for histologic studies, and with Alcian Blue (AB)/PAS for mucus glycoconjugates.

Immunohistochemical Localization of MUC5AC and EGFR in Nasal Specimens

Previously prepared 5-μm paraffin sections were deparaffinized, rehydrated, post-fixed with 4% paraformaldehyde and treated with 0.3% $H_2O_2$ in methyl alcohol. PBS containing 0.05% Tween 20, 2% normal goat serum was used as diluent for the antibodies. Tissue sections were incubated with a monoclonal antibody to EGFR (dilution, 1:200) (Calbiochem, La Jolla, Calif.) or to a monoclonal antibody to MUC5AC (dilution, 1:500) (clone 45 M1, Neomarkers, Fremont, Calif.) at room temperature for 2 hours. Sections were then incubated with biotinylated horse antimouse antibody (dilution, 1:250) (Vector laboratories, Burlingame, Calif.) at room temperature for 1 h. Bound antibody was visualized according to standard protocols for Avidin-Biotin-Peroxidase complex method (Elite ABC kit, Vector laboratories). Tissue sections were counterstained with hematoxylin. Tissue preparations for polyps and nasal mucosa from inferior turbinate were performed concomitantly. Omission of the primary antibody was used as negative control.

Quantification of AB/PAS-, MUC5AC- and EGFR-Stained Areas

Quantification of AB/PAS staining, and of MUC5AC and EGFR immunoreactivity was assessed using a semi-automatic imaging system, as described elsewhere. Lou et al. (1998) *Am. J. Respir. Crit. Care Med.* 157:1927-1934. Images of the epithelium of nasal specimens were recorded from ten high-power fields with a phase contrast lens at ×400. We measured AB/PAS-, MUC5AC- and EGFR-stained areas and the total epithelial area, and we expressed the data as the % of total area stained by AB/PAS, by an antibody to MUC5AC, or by an antibody to EGFR. Analyses were performed with public domain NIH IMAGE program (developed at the U.S. National Institute of Health and available by anonymous FTP from zippy.nimh.gov or on floppy disk from the National Technical Information Service, Springfield, Va., part number PB95-500195GEI).

First, we examined the % stained areas for AB/PAS and MUC5AC, comparing control and polyp epithelium. In control specimens, the epithelium was uniformly pseudostratified, so sampling was straightforward. However, the surface epithelium of nasal polyps presented varying morphological subtypes: (a) normal pseudostratified epithelium (composed of ciliated cells, goblet cells and a single layer of basal cells); (b) hyperplastic epithelium consisting of ciliated cells, basal and goblet cells (containing more than three cell layers, either basal cells, mucous cells or both); (c) squamous metaplasia was not observed in our specimens. Sampling had to consider this heterogeneity. First, the stained slides were examined under low magnification to determine the areas of pseudostratified and hyperplastic epithelium in each polyp. Large differences existed among the different specimens: Pseudostratified epithelium occupied a mean of 25% (range, 14-56%) and hyperplastic epithelium occupied a mean of 75% (range, 44-100%) of the intact polyp epithelium. To examine % areas stained in polyps, we obtained images of representative areas (10 high power fields) in proportion to the % of pseudostratified and hyperplastic epithelium in each polyp.

Because we found that goblet cells were more concentrated in areas of hyperplastic than pseudostratified epithelium, we compared the EGFR protein expression in the two areas. In these studies, images of ten high power fields of the two types of epithelium stained for MUC5AC protein and adjacent sections stained for EGFR protein were obtained, and the areas were compared. Because only half of the polyp specimens expressed EGFR, we determined the relationship between EGFR and MUC5AC staining in the polyps, examining ten high power fields of adjacent stained specimens.

EGFR and MUC5AC Gene Expression In Nasal Tissue

EGFR gene expression was assessed by in situ hybridization using $^{35}$S-labelled riboprobes. A 350-bp fragment was isolated from pTRI-EGFR human template (Ambion, Austin, Tex.) and subcloned into KpnI and EcoRl sites of Bluescript II SK– vector (Stratagene, La Jolla, Calif.). To prepare RNA probe for in situ hybridization, this recombinant plasmid containing the human EGFR cDNA fragment was linearized and transcribed in vitro with the T7 or T3 polymerase to obtain antisense and sense probes. The probes for in situ hybridization were generated in the presence of sulfur-35-uridine triphosphate ([$^{35}$S]UTP). For MUC5AC, riboprobes were generated from plasmids containing human. Probe isolation and in situ hybridization were performed as described previously. Lou et al. (1998) *Am. J. Respir. Crit. Care Med.* 157:1927-1934.

Immunohistochemical Localization of TNF-α in Nasal Polyps We stained the polyp specimens with a polyclonal rabbit anti-human antibody to TNF-α (dilution, 1:1000) (Genzyme Corp., Cambridge, Mass.). Quantification of TNF-α protein was performed by examining ten consecutive high power fields (×400), five in the subepithelial area and five in the stromal area, as described previously. Finotto et al. (1994) *J. Immunol.* 153:2278-2289. The values reported are expressed as positive cells per field. Under these conditions, one field represents an area of 0.25 mm$^2$.

Immunohistochemical Staining for Neutrophils

We used two antibodies to identify neutrophils in the tissue specimens: Because neutrophil elastase is a major component of human neutrophils, we used a monoclonal mouse antibody to human neutrophil elastase (HNE) (dilution, 1:5000) (DAKO Corp., Carpinteria, Calif.). In addition, because neutrophil elastase may be present in smaller amounts in cells other than neutrophils, we also used a monoclonal antibody to CD-16 (dilution, 1:500) (BioSource International, Camarillo, Calif.), which binds to the low affinity Fc receptor (FcγRIII) present on the neutrophil cell surface and which has been shown previously to distinguish neutrophils (CD-16+) from eosinophils (CD-16–)(10). For the staining technique, see paragraph describing MUC5AC and EGFR staining.

Recruited neutrophils have two effects on goblet cells: First, neutrophil elastase is a potent secretagogue of airway goblet cells. Takeyama et al. (1998) *Am. J. Physiol.* 275: L294-L302. Second, goblet cell degranulation causes EGFR expression (Lee et al. (2000) *Am. J. Respir. Crit. Care Med.* and neutrophils cause EGFR activation. Takeyama et al. (2000) *J. Immunol.* 164:1546-1552. Therefore, we counted neutrophil elastase- and CD16-stained cells in the epithelium of nasal polyps, and we compared EGFR-positive and EGFR-negative specimens. For each specimen, images of ten consecutive high power fields (×400) were obtained, and the positively-stained cells were counted. Results are expressed as the number of positively-stained cells/field. Under these conditions, one field represents an area of 0.25 mm$^2$.

Statistical Analysis

Data obtained from measurements of AB-PAS-, MUC5AC- and EGFR-stained areas and TNF-α-, HNE- and CD16-stained cells were compared using the non-parametric Mann-Whitney U test. A probability of <0.05 for the null hypothesis was accepted as indicating a statistically significant difference.

Results

Figure 15:
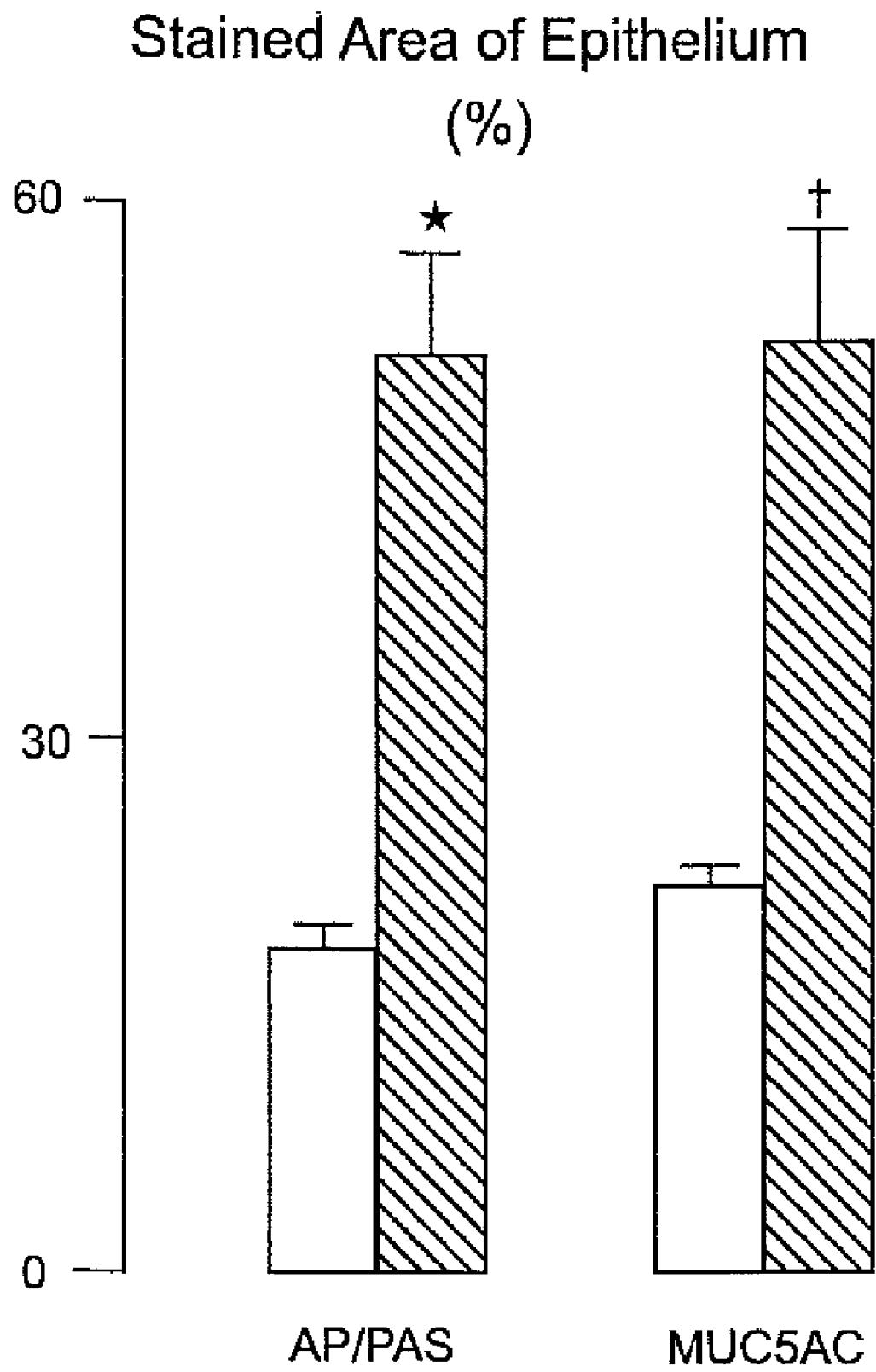
FIG. 15 is a graph depicting the percentage of AB/PAS- and MUC5AC-stained areas of epithelium in control (open columns) and nasal polyp (closed columns) epithelium. Values are expressed as mean % areas±SEM occupied by AB/PAS- and MUC5AC-stained cells.

Mucus glycoconjugates and mucin MUC5AC in normal and polyp nasal epithelium Staining with AB/PAS and immunostaining for mucin MUC5AC were positive in both normal and polyp nasal epithelium. The areas of epithelium occupied by AB/PAS and MUC5AC staining were not different from one another either in the control subjects or in the subjects with polyps (P=0.91 and P=0.10, respectively) (FIG. 15). However, the mean % stained areas were significantly larger in polyps than in control epithelium (each comparison, P<0.01).

EGFR immunoreactivity and gene expression in nasal epithelium (a) EGFR immunoreactivity.

In normal epithelium, where AB/PAS and MUC5AC staining was sparse, EGFR immunoreactivity was weak and localized to some goblet cells and non-granulated secretory cells in four subjects; in the other two subjects, the tissue did not stain with the antibody to EGFR. In these two specimens, AB/PAS and MUC5AC staining was also sparse.

In polyps, four of the eight specimens stained positively with the antibody to EGFR; the four remaining polyps were unstained with the antibody to EGFR. In the epithelium of the four EGFR-positively stained polyps, the mean % area of EGFR-positive staining was greater than in the epithelium of the four control subjects who had EGFR staining (44.07±5.95% vs 19.55±1.44%; P=0.02). In contrast to control epithelium (see above), in polyps the EGFR staining was much more intense and was concentrated in basal cells; some non-granulated secretory cells and goblet cells also stained positively. Ciliated cells were unstained in both controls and in polyps.

(b) EGFR mRNA.

Epithelium from the four control subjects that showed EGFR immunoreactivity also showed EGFR gene expression, as demonstrated by in situ hybridization. In these specimens, the signal for EGFR mRNA was weak and was located in the basal area of the epithelium. In the two control specimens where EGFR staining was absent, EGFR mRNA was also absent. In polyps, in situ hybridization for EGFR mRNA showed strong expression in the basal area of the epithelium in the four specimens that were positive for EGFR immunostaining in basal epithelium. There was little EGFR gene expression in the four polyps that did not show EGFR immunostaining; in these specimens, the signal was not localized to the basal portion of the epithelium but was mostly found in some elongated cells that appeared to be non-granulated secretory cells. Sense probe showed no signal in either polyps or in controls.

TNF-α Immunolocalization in Nasal Specimens

Because TNF-α induces EGFR expression in human epithelial cell lines in vitro and in rat tracheal epithelium in vivo, we stained the nasal specimens with a polyclonal antibody to TNF-α. In control specimens, there was no TNF-α immunoreactivity, whereas all of the polyp specimens showed immunoreactivity for TNF-α. However, the EGFR-positively stained polyps contained more TNF-α-stained cells than the EGFR-unstained polyps (1 9.55±1.13 vs 9.02±0.41 cells/field; P=0.02, n=4). The staining was concentrated in inflammatory cells in the subepithelial layer and in the deep stromal layer. Based on their morphological appearance, most of these cells were eosinophils with a characteristic bilobed nucleus. However, some mononuclear cells and neutrophils also stained positively. One specimen expressed TNF-α immunoreactivity in the epithelium, mostly in basal cells.

Relationship of EGFR Expression to Mucin MUC5AC.

(a) Comparison of Pseudostratified and Hyperplastic Epithelium in Polyps.

Figure 16:
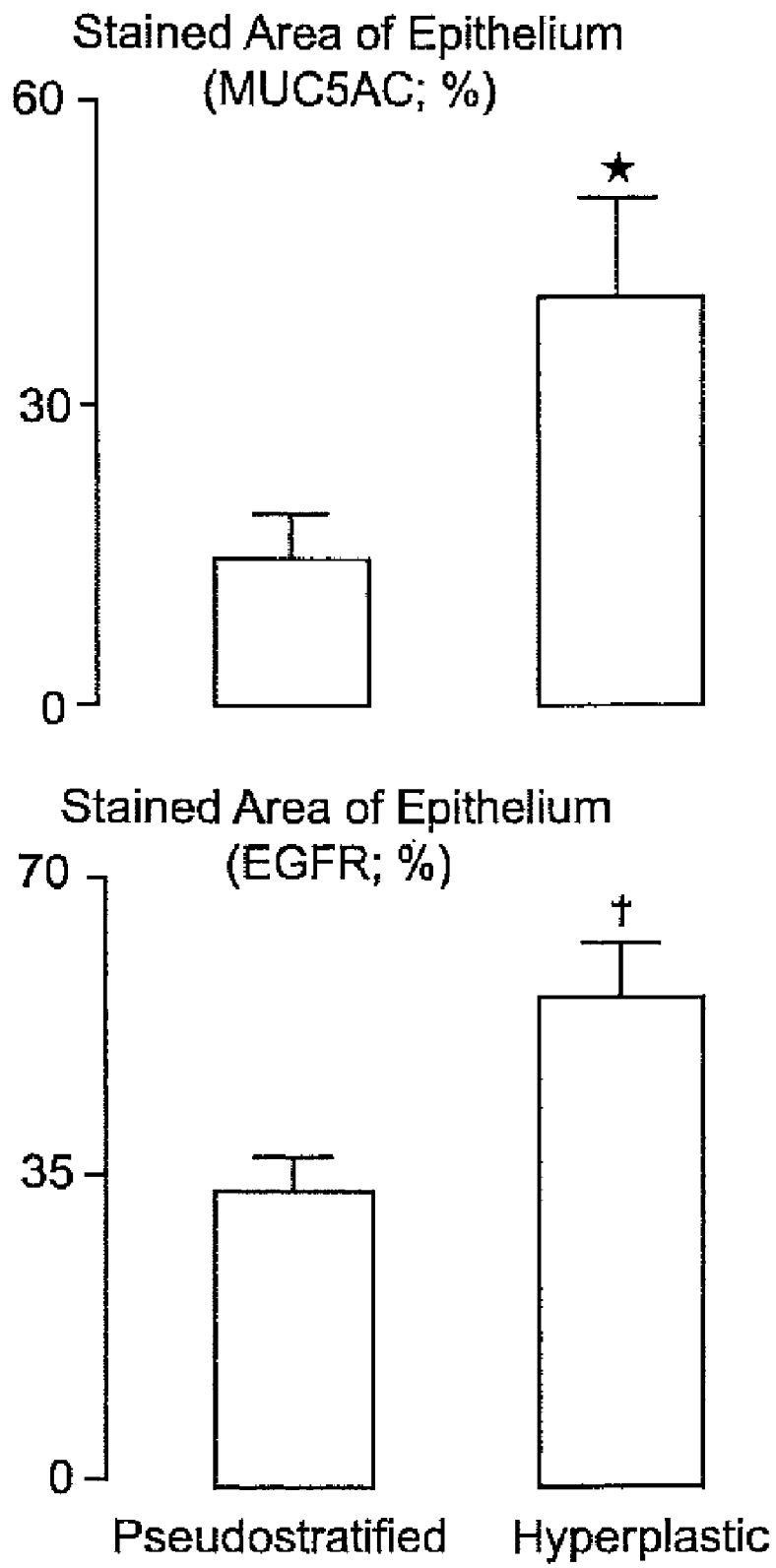
FIG. 16 is a graph depicting comparison of MUC5AC- and EGFR-stained areas in pseudostratified and hyperplastic epithelium in polyps. Results are expressed as mean % stained areas±SEM.

In control specimens, the epithelium was uniformly pseudostratified. However, in polyps, the surface epithelium was composed of pseudostratified epithelium and hyperplastic epithelium. Because we found that the areas of hyperplastic epithelium contained a significantly greater % epithelial area with AB/PAS- and MUC5AC-positive staining than the pseudostratified areas, we hypothesized that EGFR might be more strongly expressed in the areas of hyperplastic epithelium than in the areas of pseudostratified epithelium. We found that in the epithelium of EGFR-positive polyps, hyperplastic epithelium, which contained a greater area of MUC5AC staining (FIG. 16A), also contained a greater area of EGFR-positive staining than pseudostratified epithelium (FIG. 16B).

(b) Relationship Between EGFR Positivity and Mucin MUC5AC Gene and Protein Expression.

Because EGFR activation has been shown to cause mucin expression in the airway epithelium, we examined the relationship between EGFR positivity and mucin expression in the epithelium. First, these studies showed that specimens that expressed EGFR also showed mucin MUC5AC gene expression. Next, we examined the relationship between EGFR positivity in the epithelium and MUC5AC protein staining. Surprisingly, the EGFR stained group had a lower MUC5AC stained area than the group of polyps that did not have EGFR immunoreactivity (FIG. 17A). However, in the EGFR-positively stained polyps, goblet cells were smaller and there were large MUC5AC-stained areas in the lumen, suggesting active goblet cell degranulation, whereas in the polyps that showed no EGFR immunoreactivity, goblet cells appeared to be larger and showed minimal evidence of MUC5AC staining in the lumen.

Neutrophil Infiltration in Polyp Epithelium

Because neutrophil elastase has been implicated in goblet cell degranulation, to assess the hypothesis that EGFR was more strongly expressed in tissues where goblet cell degranulation occurred, we examined the localization of neutrophils in polyp specimens by staining the specimens with antibodies to elastase and to CD16. We found that the number of neutrophils in the epithelium was increased in EGFR-positive specimens compared to specimens that did not stain for EGFR (FIG. 17B).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of treating nasal polyps, the method comprising administering a therapeutically effective amount of an epidermal growth factor receptor (EGF-R) antagonist to a patient suffering from nasal polyps, wherein said EGF-R antagonist is an antibody specific for an EGF-R.

2. The method of claim 1, wherein said antibody is a monoclonal antibody.

3. The method of claim 1, wherein said antibody is a humanized antibody.

4. The method of claim 1, wherein said antibody is a chimeric antibody.

5. The method of claim 1, wherein the antagonist is administered by injection.

6. The method of claim 1, wherein the antagonist is administered with a carrier in the form of normal saline solution.

7. The method of claim 1, wherein the antagonist is administered locally to the nasal airways of the patient.

8. The method of claim 7, wherein the antagonist is administered by inhalation.

9. The method of claim 7, wherein the antagonist is administered by insufflating an aerosol.

10. The method of claim 7, wherein the antagonist is in a dry powder formulation.

11. The method of claim 7, wherein the antagonist is administered using a nebulizer.

12. The method of claim 1, wherein the antagonist is in an aqueous or ethanolic solution.

13. The method of claim 1, wherein the patient is a human.

* * * * *